United States Patent
Kato et al.

(10) Patent No.: US 11,444,246 B2
(45) Date of Patent: *Sep. 13, 2022

(54) AROMATIC AMINE DERIVATIVE, AND ORGANIC ELECTROLUMINESCENT ELEMENT USING SAME

(71) Applicant: IDEMITSU KOSAN CO., LTD., Chiyoda-ku (JP)

(72) Inventors: Tomoki Kato, Ichihara (JP); Takayasu Sado, Urayasu (JP); Takahiro Fujiyama, Kisarazu (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/903,952

(22) Filed: Jun. 17, 2020

(65) Prior Publication Data

US 2020/0321526 A1 Oct. 8, 2020

Related U.S. Application Data

(63) Continuation of application No. 15/854,404, filed on Dec. 26, 2017, which is a continuation of application
(Continued)

(30) Foreign Application Priority Data

Aug. 31, 2012 (JP) ................... 2012-191939

(51) Int. Cl.
*H01L 51/00* (2006.01)
*C07C 211/61* (2006.01)
(Continued)

(52) U.S. Cl.
CPC .......... *H01L 51/006* (2013.01); *C07C 211/61* (2013.01); *C07C 217/80* (2013.01); *C07C 217/92* (2013.01); *C07C 255/58* (2013.01); *C07D 209/86* (2013.01); *C07D 307/91* (2013.01); *C07D 333/76* (2013.01); *C07D 405/12* (2013.01); *C07D 409/12* (2013.01); *C09B 11/04* (2013.01); *C09B 57/00* (2013.01); *C09B 57/008* (2013.01); *C09K 11/06* (2013.01); *H01L 51/0061* (2013.01); *H01L 51/0073* (2013.01); *H01L 51/0074* (2013.01); *C07C 2603/18* (2017.05); *C09K 2211/1011* (2013.01); *C09K 2211/1014* (2013.01);
(Continued)

(58) Field of Classification Search
CPC ... C07C 211/55; C07C 211/61; C07C 217/80; C07C 217/92; C07C 255/58; C07C 2603/18; C07D 209/86; C07D 307/91; C07D 333/76; C07D 405/12; C07D 409/12; C09B 11/04; C09B 57/00; C09B 57/008; C09K 11/06; C09K 2211/1011; C09K 2211/1014; C09K 2211/1029; C09K 2211/1033; C09K 2211/1037; C09K 2211/1088; C09K 2211/1092; H01L 51/0052; H01L 51/0058; H01L 51/0059; H01L 51/006; H01L 51/0061; H01L 51/0073; H01L 51/0074; H01L 51/5012; H01L 51/5048; H01L 51/5052; H01L 51/5056; H01L 51/506; H01L 51/5064; H01L 51/5088; H01L 51/5096; H01L 51/5206; H01L 51/5221
See application file for complete search history.

(56) References Cited

U.S. PATENT DOCUMENTS 5,510,218 A 4/1996 Nakata et al.
6,951,694 B2 10/2005 Thompson et al.
(Continued)

FOREIGN PATENT DOCUMENTS

CN 1646660 A 7/2005
CN 1702065 A 11/2005
(Continued)

OTHER PUBLICATIONS

JP 11144875 A, 1990, machine translation (Year: 1990).*
JP-11184119-A, 1999, machine translation (Year: 1999).*
International Search Report dated Nov. 26, 2013 in PCT/JP2013/073187.
Combined Office Action and Search Report dated Jul. 4, 2016 in Taiwanese Patent Application No. 105115875 (with English translation of Categories of Cited Documents).
Combined Office Action and Search Report dated Jan. 19, 2016 in Taiwanese Patent Application No. 102131411 (with English translation of Categories of Cited Documents).
(Continued)

*Primary Examiner* — Dylan C Kershner
*Assistant Examiner* — Elizabeth M. Dahlburg
(74) *Attorney, Agent, or Firm* — Oblon, McClelland, Maier & Neustadt, L.L.P.

(57) ABSTRACT

An aromatic amine derivative represented by formula (1):

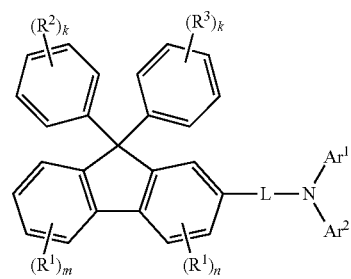

wherein $R^1$, $R^2$, $R^3$, L, $Ar^1$, $Ar^2$, k, m, and n are the same as defined in the specification, is useful as a material for an organic EL device and realizes an organic EL device with a high efficiency and a long lifetime even when driving it at a low voltage.

18 Claims, No Drawings

Related U.S. Application Data

No. 14/424,656, filed as application No. PCT/JP2013/073187 on Aug. 29, 2013, now Pat. No. 10,014,477.

(51) Int. Cl.

| | |
|---|---|
| H01L 51/50 | (2006.01) |
| C07C 217/80 | (2006.01) |
| C07C 217/92 | (2006.01) |
| C07C 255/58 | (2006.01) |
| C07D 209/86 | (2006.01) |
| C07D 307/91 | (2006.01) |
| C07D 333/76 | (2006.01) |
| C07D 405/12 | (2006.01) |
| C07D 409/12 | (2006.01) |
| C09B 11/04 | (2006.01) |
| C09B 57/00 | (2006.01) |
| C09K 11/06 | (2006.01) |
| H01L 51/52 | (2006.01) |

(52) U.S. Cl.
CPC ............... C09K 2211/1029 (2013.01); C09K 2211/1033 (2013.01); C09K 2211/1037 (2013.01); C09K 2211/1088 (2013.01); C09K 2211/1092 (2013.01); H01L 51/0052 (2013.01); H01L 51/0058 (2013.01); H01L 51/5012 (2013.01); H01L 51/5056 (2013.01); H01L 51/5088 (2013.01); H01L 51/5206 (2013.01); H01L 51/5221 (2013.01)

(56) References Cited

U.S. PATENT DOCUMENTS

| | | | |
|---|---|---|---|
| 10,854,822 B2 * | 12/2020 | Kato | C07D 405/12 |
| 2003/0225234 A1 | 12/2003 | Jaycox et al. | |
| 2005/0124732 A1 | 6/2005 | Jaycox et al. | |
| 2005/0131185 A1 | 6/2005 | Jaycox et al. | |
| 2005/0209180 A1 | 9/2005 | Jadhav et al. | |
| 2005/0221124 A1 | 10/2005 | Hwang et al. | |
| 2005/0222066 A1 | 10/2005 | Richards et al. | |
| 2005/0227935 A1 | 10/2005 | McSwiggen et al. | |
| 2005/0244670 A1 | 11/2005 | Saitoh et al. | |
| 2006/0166034 A1 | 7/2006 | Saitoh et al. | |
| 2006/0232198 A1 | 10/2006 | Kawamura et al. | |
| 2007/0018571 A1 | 1/2007 | Hwang et al. | |
| 2007/0215889 A1 | 9/2007 | Kawakami et al. | |
| 2008/0145708 A1 | 6/2008 | Heil et al. | |
| 2009/0115320 A1 | 5/2009 | Kawamura et al. | |
| 2009/0278451 A1 | 11/2009 | Hwang et al. | |
| 2009/0302758 A1 | 12/2009 | Saitoh et al. | |
| 2010/0001636 A1 | 1/2010 | Yabunouchi | |
| 2010/0025669 A1 | 2/2010 | Hwang et al. | |
| 2010/0230666 A1 | 9/2010 | Ohuchi et al. | |
| 2011/0084258 A1 | 4/2011 | Kim et al. | |
| 2011/0193476 A1 | 8/2011 | Higo et al. | |
| 2011/0215308 A1 | 9/2011 | Im et al. | |
| 2011/0248246 A1 | 10/2011 | Ogita et al. | |
| 2011/0248247 A1 | 10/2011 | Matsumoto et al. | |
| 2011/0266531 A1 | 11/2011 | Kim et al. | |
| 2011/0278551 A1 | 11/2011 | Yabunouchi et al. | |
| 2012/0007070 A1 | 1/2012 | Kai et al. | |
| 2012/0012832 A1 | 1/2012 | Yabunouchi et al. | |
| 2012/0043531 A1 | 2/2012 | Jung et al. | |
| 2012/0043533 A1 | 2/2012 | Mizuki et al. | |
| 2012/0074395 A1 | 3/2012 | Yabunouchi et al. | |
| 2012/0119197 A1 | 5/2012 | Nishimura et al. | |
| 2012/0146014 A1 | 6/2012 | Kato | |
| 2012/0181530 A1 | 7/2012 | Funyuu et al. | |
| 2012/0211742 A1 | 8/2012 | Horikiri et al. | |
| 2012/0248426 A1 | 10/2012 | Kato | |
| 2012/0326137 A1 | 12/2012 | Song et al. | |
| 2012/0326141 A1 | 12/2012 | Pflumm et al. | |
| 2013/0001528 A1 | 1/2013 | Chang et al. | |
| 2013/0105771 A1 | 5/2013 | Ryu et al. | |
| 2013/0187138 A1 | 7/2013 | Matsumoto et al. | |
| 2013/0234118 A1 | 9/2013 | Kwon et al. | |
| 2014/0374720 A1 | 12/2014 | Kato et al. | |
| 2015/0243891 A1 | 8/2015 | Kato et al. | |
| 2020/0313090 A1 * | 10/2020 | Kato | H01L 51/0074 |
| 2020/0321526 A1 | 10/2020 | Kato et al. | |

FOREIGN PATENT DOCUMENTS

| | | |
|---|---|---|
| CN | 1861740 A | 11/2006 |
| CN | 102093232 A | 6/2011 |
| CN | 102356060 A | 2/2012 |
| CN | 102372661 A | 3/2012 |
| CN | 102482215 A | 5/2012 |
| CN | 104487541 A | 4/2015 |
| EP | 2 309 565 | 4/2011 |
| JP | 7-72639 A | 3/1995 |
| JP | 10-95972 A | 4/1998 |
| JP | 11-144873 A | 5/1999 |
| JP | 11-144875 A | 5/1999 |
| JP | 11-162649 A | 6/1999 |
| JP | 11-184109 A | 7/1999 |
| JP | 11-184119 A | 7/1999 |
| JP | 11184119 A | 7/1999 |
| JP | 2000-302756 A | 10/2000 |
| JP | 2001-288462 A | 10/2001 |
| JP | 2002-69044 A | 3/2002 |
| JP | 2003-48868 A | 2/2003 |
| JP | 2005-44791 A | 2/2005 |
| JP | 2005-290000 A | 10/2005 |
| JP | 2007-48833 A | 2/2007 |
| JP | 2008-34701 A | 2/2008 |
| JP | 2008-130840 A | 6/2008 |
| JP | 2008-285460 A | 11/2008 |
| JP | 2008-300503 A | 12/2008 |
| JP | 2009-10364 A | 1/2009 |
| JP | 2009-147276 A | 7/2009 |
| JP | 2009-149850 A | 7/2009 |
| JP | 2009149850 A | 7/2009 |
| JP | 2010-37312 A | 2/2010 |
| JP | 2010-92940 A | 4/2010 |
| JP | WO 2010106806 A1 | 9/2010 |
| JP | 2010-222268 A | 10/2010 |
| JP | WO 2011021520 A1 | 2/2011 |
| JP | 2011-51936 A | 3/2011 |
| JP | 2012-41387 A | 3/2012 |
| JP | 2012-111719 A | 6/2012 |
| JP | 2013-63929 A | 4/2013 |
| JP | 2013-107853 A | 6/2013 |
| JP | 2013-539205 A | 10/2013 |
| KR | 10-0573137 B1 | 4/2006 |
| KR | 10-2007-0012110 A | 1/2007 |
| KR | 10-2010-0003632 A | 1/2010 |
| KR | 10-2010-0006072 A | 1/2010 |
| KR | 10-2010-0007639 A | 1/2010 |
| KR | 20100003632 A | 1/2010 |
| KR | 10-2010-0013165 A | 2/2010 |
| KR | 10-2010-0118514 A | 11/2010 |
| KR | 10-1029082 B1 | 4/2011 |
| KR | 2011-0111844 A | 10/2011 |
| KR | 10-2011-0134581 A | 12/2011 |
| KR | 2011-134581 A | 12/2011 |
| KR | 10-2012-0001576 A | 1/2012 |
| KR | 10-2012-0011445 A | 2/2012 |
| KR | 10-2012-0017382 | 2/2012 |
| KR | 10-2012-0052993 A | 5/2012 |
| KR | 10-2012-0066076 | 6/2012 |
| KR | 10-2012-0137321 A | 12/2012 |
| KR | 10-2013-0051321 A | 5/2013 |
| KR | 2013-51321 A | 5/2013 |
| KR | 10-2013-0121597 A | 11/2013 |
| KR | 2013-121516 A | 11/2013 |
| KR | 2013-121597 A | 11/2013 |
| KR | 2014-33301 A | 3/2014 |
| TW | 201016663 A1 | 5/2010 |
| WO | WO 2004/097020 A2 | 11/2004 |
| WO | WO 2007/125714 A1 | 11/2007 |
| WO | WO 2007/148660 A1 | 12/2007 |

(56) References Cited

FOREIGN PATENT DOCUMENTS

| | | |
|---|---|---|
| WO | WO 2008/062636 A1 | 5/2008 |
| WO | WO 2008/132103 A1 | 11/2008 |
| WO | WO 2008/143175 A1 | 11/2008 |
| WO | WO 2009/008100 A1 | 1/2009 |
| WO | WO 2009/099060 A1 | 8/2009 |
| WO | WO 2009/145016 A1 | 12/2009 |
| WO | WO 2010/013675 A1 | 2/2010 |
| WO | WO 2010/064871 A1 | 6/2010 |
| WO | WO 2010/113761 | 10/2010 |
| WO | WO 2011/008169 A1 | 1/2011 |
| WO | WO 2011/021520 A1 | 2/2011 |
| WO | WO 2011/037429 A2 | 3/2011 |
| WO | WO 2012/011642 A1 | 1/2012 |
| WO | WO 2012/015265 A1 | 2/2012 |
| WO | WO 2012015265 A1 | 2/2012 |
| WO | WO 2012/070226 A1 | 5/2012 |
| WO | WO 2012/078005 A2 | 6/2012 |
| WO | WO 2012/091471 A2 | 7/2012 |
| WO | WO 2012/096263 A1 | 7/2012 |
| WO | WO 2012/096382 A1 | 7/2012 |
| WO | WO 2012091471 A2 | 7/2012 |
| WO | WO 2012/105629 A1 | 8/2012 |
| WO | WO 2012/137741 A1 | 10/2012 |
| WO | WO 2012/157211 A1 | 11/2012 |
| WO | WO 2012/176818 A1 | 12/2012 |
| WO | WO 2012/177006 A2 | 12/2012 |
| WO | WO 2013/002514 A2 | 1/2013 |
| WO | WO 2013/032304 A2 | 3/2013 |
| WO | WO 2013/035329 A1 | 3/2013 |
| WO | WO 2013/039073 A1 | 3/2013 |
| WO | WO 2013/039221 A1 | 3/2013 |
| WO | WO 2013/042769 A1 | 3/2013 |
| WO | WO 2013/042775 A1 | 3/2013 |
| WO | WO 2013/077385 A1 | 5/2013 |
| WO | WO 2013/077405 A1 | 5/2013 |
| WO | WO 2013/077406 A1 | 5/2013 |
| WO | WO 2013/087142 A1 | 6/2013 |
| WO | WO 2013/118812 A1 | 8/2013 |
| WO | WO 2013/118846 A1 | 8/2013 |
| WO | WO 2013/118847 A1 | 8/2013 |
| WO | WO 2013/175747 A1 | 11/2013 |
| WO | WO 2013/187007 A1 | 12/2013 |
| WO | WO 2014/002873 A1 | 1/2014 |
| WO | WO 2014/015935 A2 | 1/2014 |
| WO | WO 2014/015937 A1 | 1/2014 |
| WO | WO 2014/015938 A1 | 1/2014 |
| WO | WO 2014/30822 A1 | 2/2014 |
| WO | WO 2014/034795 A1 | 6/2014 |

OTHER PUBLICATIONS

Combined Office Action and Search Report dated Jan. 27, 2016 in Chinese Patent Application No. 201380045022.3 (with English translation of Categories of Cited Documents).
Japanese Office Action dated Dec. 15, 2015 in Patent Application No. 2015-149545 (without English Translation).
Office Action dated Apr. 27, 2016 in Korean Patent Application No. 10-2015-7005242.
Office Action dated Sep. 29, 2016 in Korean Patent Application No. 10-2016-7013080.
Combined Chinese Office Action and Search Report dated May 24, 2017 in Patent Application No. 201510747799.5 (with English language translation of categories of cited documents).
Machine translation for WO2012091471 A2.
Machine translation of JP 11/144875 A.
Korean Office Action dated May 30, 2018 in Korean Patent Application No. 10-2017-7014653 (with unedited computer generated English translation), 13 pages.
Office Action dated Aug. 30, 2019 in Chinese Patent No. 201710696223.X.
Office Action dated Jan. 22, 2020 in Chinese Patent Application No. 201510747799.5, 9 pages.
Office Action dated May 26, 2020 in Chinese Patent Application No. 201710696223.X, (w/ English translation).
Decision on Appeal in the corresponding U.S. Appl. No. 15/854,404, dated Sep. 9, 2020.
Office Action dated Nov. 4, 2020, in corresponding European Patent Application No. 13833783.7.
Chinese Office Action dated Dec. 1, 2020, in Chinese Patent Application No. 201710696223.X, 5 pages.
Notice of submission of cancellation opinion dated Jun. 4, 2019 in Korean Patent Application No. 10-2015-7005242 (with English language translation), 21 pages.
Office Action dated Aug. 19, 2020 in co-pending U.S. Appl. No. 16/901,610, 27 pages.
Office Action dated Mar. 29, 2021, in corresponding U.S. Appl. No. 16/901,610.
Office Action dated Sep. 28, 2021, in co-pending U.S. Appl. No. 15/854,404.
Office Action dated Nov. 26, 2021, in corresponding U.S. Appl. No. 16/901,610.
Office Action dated Mar. 18, 2022, in corresponding U.S. Appl. No. 15/854,404.
Office Action dated Jul. 8, 2022, in co-pending U.S. Appl. No. 15/854,404 Examiner E. Dahlburg.

* cited by examiner

AROMATIC AMINE DERIVATIVE, AND ORGANIC ELECTROLUMINESCENT ELEMENT USING SAME

CROSS REFERENCE TO RELATED APPLICATIONS

This application is a continuation application of prior U.S. application Ser. No. 15/854,404, filed Dec. 26, 2017, the disclosure of which is incorporated herein by reference in its entirety. U.S. application Ser. No. 15/854,404 is a continuation application of prior U.S. application Ser. No. 14/424,656, filed Feb. 27, 2015, the disclosure of which is incorporated herein by reference in its entirety. U.S. application Ser. No. 14/424,656 is the National Stage of PCT/JP13/073187, filed Aug. 29, 2013, the disclosure of which is incorporated herein by reference in its entirety. U.S. application Ser. No. 14/424,656 claims priority to Japanese Application No. 2012-191939, filed Aug. 31, 2012, the disclosure of which is incorporated herein by reference in its entirety.

TECHNICAL FIELD

The present invention relates to aromatic amine derivatives and organic electroluminescence devices using the aromatic amine derivatives. For example, the present invention relates to aromatic amine derivatives having a substituted or unsubstituted 9,9-diphenylfluorene skeleton and organic electroluminescence devices employing the aromatic amine derivative.

BACKGROUND ART

Generally, an organic electroluminescence (EL) device includes an anode, a cathode, and at least one organic thin film layers which are interposed between the anode and the cathode. When applying a voltage between both electrodes, electrons are injected into an emission region from the cathode side and holes are injected into the emission region from the anode side. The injected electrons and holes are recombined in the emission region to generate an excited state. When the excited state returns to a ground state, light is emitted. Therefore, to obtain a high-efficiency organic EL device, it is important to develop a compound which efficiently transports electrons or holes into an emission region and facilitates the recombination of electron and hole.

Generally, when driving or storing an organic EL device in a high-temperature environment, various problems occur, for example, the emission color is changed, the emission efficiency is reduced, the driving voltage is increased, and the emission life is shortened. To eliminate these drawbacks, various hole transporting materials have been proposed, for example, Patent Document 1 discloses an aromatic amine derivative in which a N-carbazolyl group is directly bonded to a 9,9-diphenylfluorene skeleton, Patent Document 2 discloses an aromatic amine derivative in which a 3-carbazolyl group is directly bonded to a 9,9-dimethylfluorene skeleton, Patent Document 3 discloses an aromatic amine derivative in which a N-carbazolylphenyl group is bonded to a 9,9-diphenylfluorene skeleton via a nitrogen atom, and Patent Document 4 discloses an aromatic amine derivative in which a 3-carbazolyl group is bonded to a 9,9-diphenylfluorene skeleton via a nitrogen atom.

However, the aromatic amine derivatives disclosed in Patent Documents 1 to 4 are still insufficient for reducing the driving voltage and prolonging the lifetime. Therefore, a further improvement has been required.

Patent Document 5 proposes an aromatic amine derivative which includes a skeleton selected from a fluorene skeleton, a carbazole skeleton, a dibenzofuran skeleton, and a dibenzothiophene skeleton and teaches that an organic EL device in which the aromatic amine derivative is used as a material for an organic EL device, particularly as a hole transporting material, is capable of driving a low voltage and has a long lifetime. Patent Document 5 discloses a compound in which a diarylamino group is bonded to 2-position of a 9,9-diphenylfluorene skeleton. In the proposed compound, a carbazole skeleton, a dibenzofuran skeleton, or a dibenzothiophene skeleton must be bonded to a terminal end of one aryl group of the diarylamino group. In all the exemplary compounds having a 9,9-diphenylfluorene skeleton which are disclosed in Patent Document 5, a biphenylene group intervenes between the terminal groups and the nitrogen atom. However, a 2-diarylamino-9,9-diphenyl fluorene compound having such an intervening biphenylene group is insufficient in the emission efficiency when driving at a low voltage and also insufficient in the lifetime (see Examples 1-1 to 1-4 and Comparative Examples 1-1 to 1-2 described herein). Therefore, it has been required to develop a material for an organic EL device, particularly a hole transporting material, which can be synthesized easily and realize an organic EL device having a high efficiency when driving at a low voltage and long-lifetime.

CITATION LIST

Patent Documents

Patent Document 1: WO 07/148660
Patent Document 2: WO 08/062636
Patent Document 3: US 2007/0215889
Patent Document 4: JP 2005-290000A
Patent Document 5: WO 2011/021520

SUMMARY OF THE INVENTION

Problems to be Solved by the Invention

The present invention has been made in view of solving the above problems and an object of the invention is to provide a long-lifetime, high-efficiency organic EL device which is capable of driving at a low voltage and provide a material for an organic EL device, for example, a hole transporting material, which realizes such an organic EL device.

Means for Solving the Problems

As a result of extensive research, the inventors have found that a compound wherein a disubstituted amino group is bonded to 2-position of a 9,9-diphenylfluorene skeleton directly or indirectly and at least one substituent of the disubstituted amino group is bonded to the nitrogen atom directly or via a phenylene group is excellent in the hole injecting ability and the hole transporting ability, and further found that such a compound realizes a long-lifetime, high-efficiency organic EL device which is capable of driving at a low voltage.

The present invention provides an aromatic amine derivative represented by formula (1):

(1)
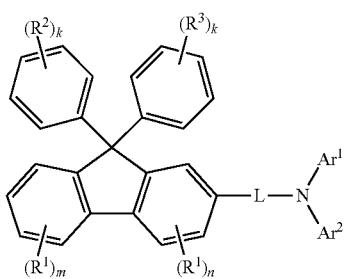
in formula (1), Ar¹ represents a group selected from formulae (2) to (4):
(2)
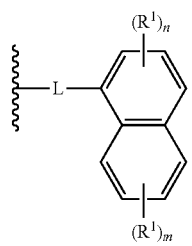
(3)
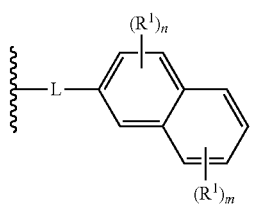
(4)
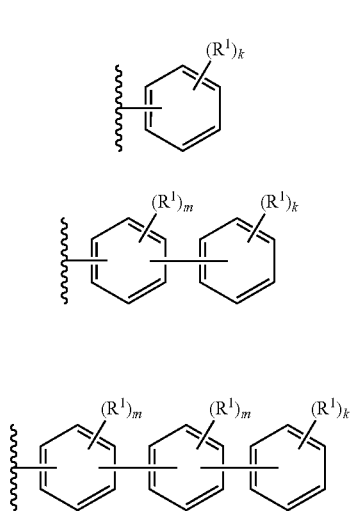
Ar² represents a group selected from formulae (6) to (15):
(6)
(7)
(8)
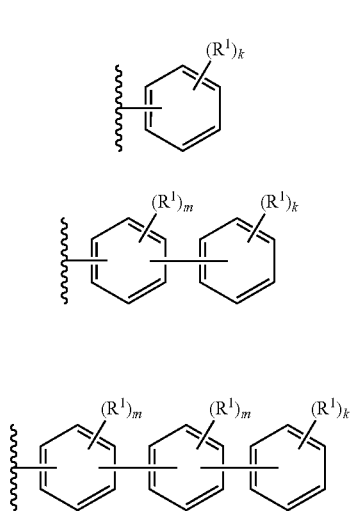
(9)
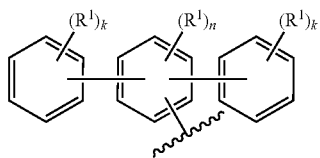
(10)
(11)
(12)
(13)
(14)
(15)
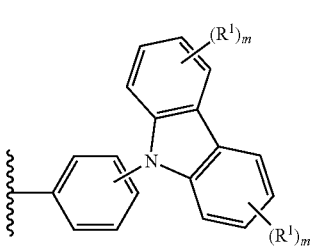
in formulae (1) to (4) and (10) to (14), L represents a single bond or a divalent group represented by formula (16), and when the aromatic amine derivative represented by formula (1) includes groups L, the groups L may be the same or different;

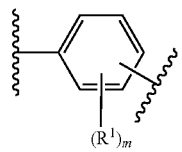

(16)

in formulae (1) to (4) and (6) to (16), $R^1$ represents a hydrogen atom, a substituted or unsubstituted alkyl group having 1 to 20 carbon atoms, a substituted or unsubstituted aryl group having 6 to 50 ring carbon atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, or a cyano group, and when groups $R^1$ exist, the groups $R^1$ may be the same or different;

in formula (1), $R^2$ and $R^3$ may be the same or different and independently represent a hydrogen atom, a substituted or unsubstituted alkyl group having 1 to 20 carbon atoms, a substituted or unsubstituted aryl group having 6 to 50 ring carbon atoms, a substituted or unsubstituted heterocyclic group having 3 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group, when groups $R^2$ exist, the groups $R^2$ may be the same or different, and when groups $R^3$ exist, the groups $R^3$ may be the same or different;

in formulae (4) and (14), two groups $R^4$ may be the same or different and independently represent a hydrogen atom, a substituted or unsubstituted alkyl group having 1 to 20 carbon atoms, a substituted or unsubstituted aryl group having 6 to 50 ring carbon atoms, a substituted or unsubstituted heterocyclic group having 3 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group, and when the aromatic amine derivative represented by formula (1) includes a group represented by formula (4) and/or a group represented by formula (14), $R^2$, $R^3$ and $R^4$ may be the same or different;

k represents an integer of 1 to 5;
m represents an integer of 1 to 4; and
n represents an integer of 1 to 3.

The present invention further provides an organic electroluminescence device comprising an anode, a cathode, and at least one organic thin film layers between the anode and the cathode, wherein the at least one organic thin film layers comprises a light emitting layer and at least one of the organic thin film layers comprises the aromatic amine derivative represented by formula (1).

Effects of the Invention

By using the aromatic amine derivative of the invention, a long-lifetime, high-efficiency organic EL device capable of driving at a low voltage is obtained.

Mode for Carrying Out the Invention

The term of "a to b carbon atoms" referred to by "a substituted or unsubstituted X group having a to b carbon atoms" used herein is the number of carbon atoms of the unsubstituted X group and does not include any carbon atom in the substituent of the substituted X group.

The definition of "hydrogen atom" used herein includes isotopes different in the neutron numbers, i.e., light hydrogen (protium), heavy hydrogen (deuterium), and tritium.

The optional substituent referred to by "substituted or unsubstituted" used herein is selected from the group consisting of an alkyl group having 1 to 50, preferably 1 to 10, more preferably 1 to 5 carbon atoms; a cycloalkyl group having 3 to 50, preferably 3 to 6, more preferably 5 or 6 ring carbon atoms; an aryl group having 6 to 50, preferably 6 to 24, more preferably 6 to 12 ring carbon atoms; an aralkyl group having 1 to 50, preferably 1 to 10, more preferably 1 to 5 carbon atoms which includes an aryl group having 6 to 50, preferably 6 to 24, more preferably 6 to 12 ring carbon atoms; an amino group; a mono- or dialkylamino group having an alkyl group having 1 to 50, preferably 1 to 10, more preferably 1 to 5 carbon atoms; a mono- or diarylamino group having an aryl group having 6 to 50, preferably 6 to 24, more preferably 6 to 12 ring carbon atoms; an alkoxy group having an alkyl group having 1 to 50, preferably 1 to 10, more preferably 1 to 5 carbon atoms; an aryloxy group having an aryl group having 6 to 50, preferably 6 to 24, more preferably 6 to 12 ring carbon atoms; a mono-, di- or tri-substituted silyl group having a substituent selected from an alkyl group having 1 to 50, preferably 1 to 10, more preferably 1 to 5 carbon atoms and an aryl group having 6 to 50, preferably 6 to 24, more preferably 6 to 12 ring carbon atoms; a heteroaryl group having 5 to 50, preferably 5 to 24, more preferably 5 to 12 ring atoms and having 1 to 5, preferably 1 to 3, more preferably 1 to 2 hetero atoms, such as a nitrogen atom, an oxygen atom and a sulfur atom; a halogen atom selected from a fluorine atom, a chlorine atom, a bromine atom and an iodine atom; a cyano group; and a nitro group.

The aromatic amine derivative of the invention is represented by formula (1):

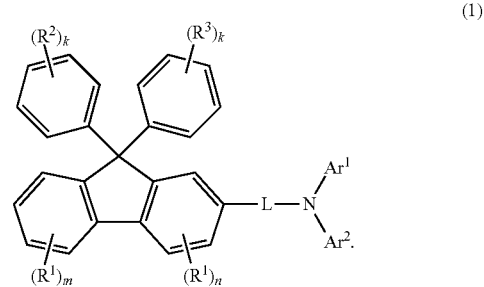

(1)

In formula (1), $Ar^1$ represents a group selected from formulae (2) to (4):

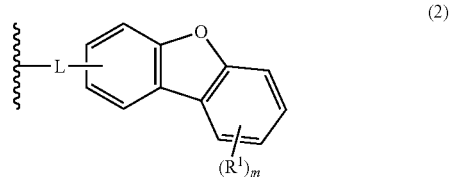

(2)

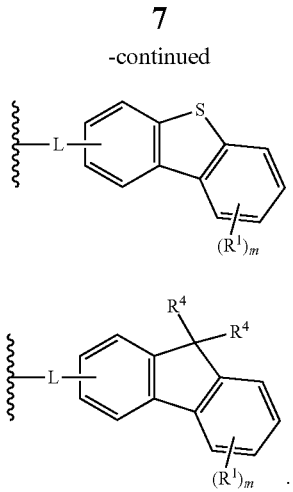
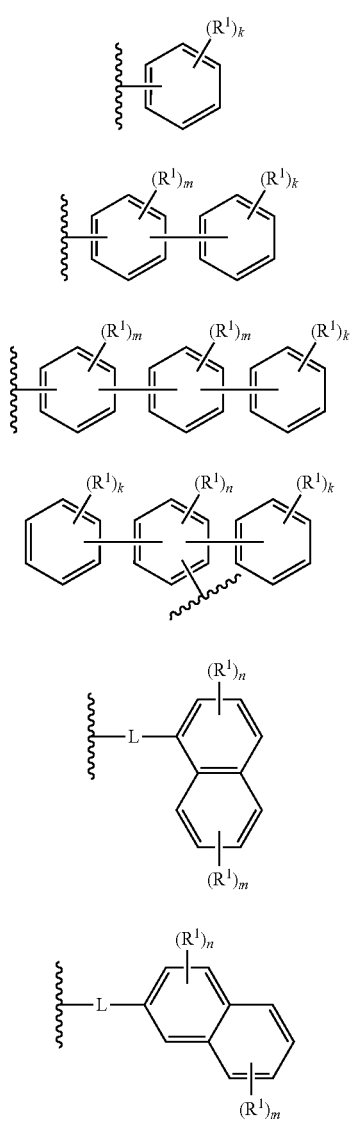
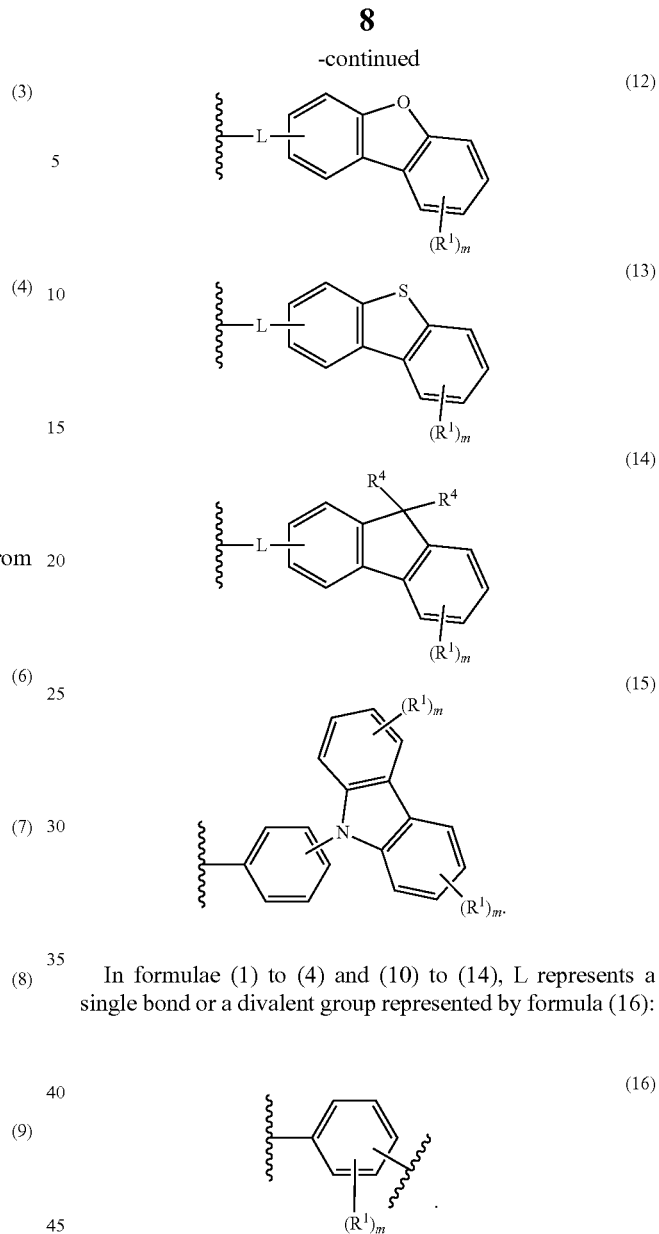

In formula (1), Ar² represents a group selected from formulae (6) to (15):

In formulae (1) to (4) and (10) to (14), L represents a single bond or a divalent group represented by formula (16):

L in formula (1) represents preferably a single bond or a phenylene group and more preferably a single bond. L in formulae (2) to (4) and (10) to (14) represents preferably a single bond or a phenylene group and more preferably a phenylene group and preferably bonds to 2- or 4-position of a dibenzofuran skeleton and a dibenzothiophene skeleton and bonds to 2-position of a fluorene skeleton. When the aromatic amine derivative represented by formula (1) includes groups L, the groups L may be the same or different.

In formulae (1) to (4) and (6) to (16), $R^1$ represents a hydrogen atom, a substituted or unsubstituted alkyl group having 1 to 20, preferably 1 to 5, and more preferably 1 to 4 carbon atoms, a substituted or unsubstituted aryl group having 6 to 50, preferably 6 to 24, and more preferably 6 to 12 ring carbon atoms, a halogen atom, a substituted or unsubstituted fluoroalkyl group having 1 to 20, preferably 1 to 5, and more preferably 1 to 4 carbon atoms, a substituted or unsubstituted alkoxy group having 1 to 20, preferably 1 to 5, and more preferably 1 to 4 carbon atoms, a substituted or unsubstituted fluoroalkoxy group having 1 to 20, preferably 1 to 5, and more preferably 1 to 4 carbon atoms, or a cyano group. When the aromatic amine derivative represented by formula (1) includes groups $R^1$, the groups $R^1$ may be the same or different.

Examples of the alkyl group having 1 to 20 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups), with a methyl group, an ethyl group, a n-propyl group, an isopropyl group, a n-butyl group, an isobutyl group, a s-butyl group, a t-butyl group, and a pentyl group (inclusive of isomeric groups) being preferred, a methyl group, an ethyl group, a n-propyl group, an isopropyl group, a n-butyl group, an isobutyl group, a s-butyl group, and a t-butyl group being more preferred, and a methyl group and a t-butyl group being particularly preferred.

Examples of the aryl group having 6 to 50 ring carbon atoms include a phenyl group, a naphthylphenyl group, a biphenylyl group, a terphenylyl group, a biphenylenyl group, a naphthyl group, a phenylnaphthyl group, an acenaphthylenyl, an anthryl group, a benzanthryl group, an aceanthryl group, a phenanthryl group, a benzophenanthryl group, a phenalenyl group, a fluorenyl group, a 9,9-dimethylfluorenyl group, a 7-phenyl-9,9-dimethylfluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, and a perylenyl group, with a phenyl group, a naphthylphenyl group, a biphenylyl group, a terphenylyl group, a naphthyl group, and a 9,9-dimethylfluorenyl group being preferred, a phenyl group, a biphenylyl group, a naphthyl group, and a 9,9-dimethylfluorenyl group being more preferred, and a phenyl group being particularly preferred.

Examples of the halogen atom include a fluorine atom, a chlorine atom, a bromine atom and an iodine atom, with a fluorine atom being particularly preferred.

Examples of the fluoroalkyl group having 1 to 20 carbon atoms include a group obtained by substituting a fluorine atom for at least one hydrogen atom, preferably 1 to 7 hydrogen atom of the alkyl group having 1 to 20 carbon atoms mentioned above, and preferably a heptafluoropropyl group, a pentafluoroethyl group, a 2,2,2-trifluoroethyl group, and a trifluoromethyl group, more preferably a pentafluoroethyl group, a 2,2,2-trifluoroethyl group, and a trifluoromethyl group, and particularly preferably a trifluoromethyl group.

Examples of the alkoxy group having 1 to 20 carbon atoms are represented by $-OR^{10}$, wherein $R^{10}$ represents the alkyl group having 1 to 20 carbon atoms mentioned above, and preferably a t-butoxy group, a propoxy group, an ethoxy group or a methoxy group, more preferably an ethoxy group or a methoxy group, and particularly preferably a methoxy group.

Examples of the fluoroalkoxy group having 1 to 20 carbon atoms are represented by $-OR^{11}$, wherein $R^{10}$ represents the fluoroalkyl group having 1 to 20 carbon atoms mentioned above, and preferably a heptafluoropropoxy group, a pentafluoroethoxy group, a 2,2,2-trifluoroethoxy group, or a trifluoromethoxy group, more preferably a pentafluoroethoxy group, a 2,2,2-trifluoroethoxy group, or a trifluoromethoxy group, and particularly preferably a trifluoromethoxy group.

In a preferred embodiment of the invention, $R^1$ to be bonded to the fluorene skeleton of formula (1) is preferably a hydrogen atom, the halogen atom mentioned above (a fluorine atom), the alkyl group mentioned above (a methyl group and a t-butyl group), and the aryl group mentioned above (a phenyl group). $R^1$ is preferably bonded to 7-positon of the fluorene skeleton and particularly preferably a hydrogen atom.

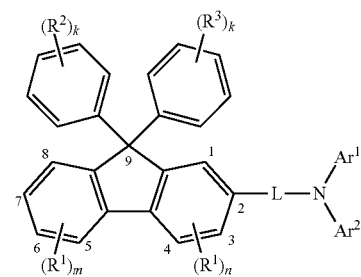

In a preferred embodiment of the invention, $R^1$ of formulae (2), (3), (12) and (13) is preferably a hydrogen atom, the alkyl group mentioned above (a methyl group), or the aryl group mentioned above (a phenyl group), which is preferably bonded to 6- or 8-position of the dibenzofuran skeleton and the dibenzothiophene skeleton. $R^1$ is particularly preferably a hydrogen atom.

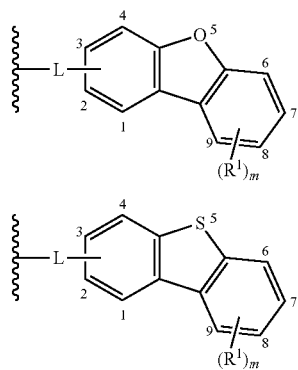

In a preferred embodiment of the invention, $R^1$ of formulae (4), (14) and (15) is preferably a hydrogen atom, a methyl group, a t-butyl group, or a phenyl group, which is preferably bonded to 7-position of the fluorene skeleton or 3- or 6-position of the carbazole skeleton. $R^1$ is particularly preferably a hydrogen atom.

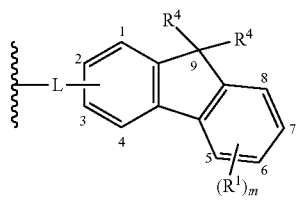

-continued

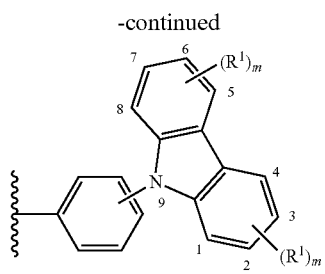

In a preferred embodiment of the invention, $R^1$ of formulae (6) to (9) is preferably selected from a hydrogen atom, the alkyl group mentioned above (a methyl group and a t-butyl group), the halogen atom mentioned above (a fluorine atom), the fluoroalkyl group mentioned above (a trifluoromethyl group), the alkoxy group mentioned above (a methoxy group), the fluoroalkoxy group mentioned above (a trifluoromethoxy group), and a cyano group. $R^1$ is preferably bonded to o-position and/or p-position of the terminal phenyl group and o-position and/or m-position of the phenylene group. W is particularly preferably a hydrogen atom.

In a preferred embodiment of the invention, $R^1$ of formulae (10) and (11) is preferably a hydrogen atom, a methyl group, a t-butyl group, or a phenyl group. $R^1$ is preferably bonded to 6- or 7-position of the naphthalene skeleton. $R^1$ is particularly preferably a hydrogen atom.

In formula (1), $R^2$ and $R^3$ may be the same or different and independently represent a hydrogen atom, a substituted or unsubstituted alkyl group having 1 to 20, preferably 1 to 5, and more preferably 1 to 4 carbon atoms, a substituted or unsubstituted aryl group having 6 to 50, preferably 6 to 24, and more preferably 6 to 12 ring carbon atoms, a substituted or unsubstituted heterocyclic group having 3 to 50, preferably 3 to 24, and more preferably 3 to 12 ring atoms, a halogen atom, a substituted or unsubstituted fluoroalkyl group having 1 to 20, preferably 1 to 5, and more preferably 1 to 4 carbon atoms, a substituted or unsubstituted alkoxy group having 1 to 20, preferably 1 to 5, and more preferably 1 to 4 carbon atoms, a substituted or unsubstituted fluoroalkoxy group having 1 to 20, preferably 1 to 5, and more preferably 1 to 4 carbon atoms, a substituted or unsubstituted aryloxy group having 6 to 50, preferably 6 to 24, and more preferably 6 to 12 carbon atoms, or a cyano group. When the aromatic amine derivative represented by formula (1) includes groups $R^2$, the groups $R^2$ may be the same or different, and when includes groups $R^3$, the groups $R^3$ may be the same or different.

The details of the alkyl group having 1 to 20 carbon atoms, the aryl group having 6 to 50 ring carbon atoms, the halogen atom, the fluoroalkyl group having 1 to 20 carbon atoms, the alkoxy group having 1 to 20 carbon atoms, and the fluoroalkoxy group having 1 to 20 carbon atoms for $R^2$ and $R^3$ are the same as defined above with respect to $R^1$.

The heterocyclic group having 3 to 50 ring atoms includes at least one, preferably 1 to 3 hetero atoms, for example, a nitrogen atom, a sulfur atom, and an oxygen atom. Examples thereof include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group, and a xanthenyl group. Preferred are a furyl group, a thienyl group, a pyridyl group, a pyridazinyl group, a pyrimidinyl group, a pyrazinyl group, a triazinyl group, a benzofuranyl group, a benzothiophenyl group, a dibenzofuranyl group, and a dibenzothiophenyl group. More preferred are a benzofuranyl group, a benzothiophenyl group, a dibenzofuranyl group, and a dibenzothiophenyl group.

The aryloxy group having 6 to 50 ring carbon atoms is represented by $—OR^{12}$, wherein $R^{12}$ represents the aryl group having 6 to 50 ring carbon atoms which is defined above with respect to $R^1$, preferably a terphenyl group, a biphenyl group or a phenyl group, more preferably a biphenyl group or a phenyl group, and particularly preferably a phenyl group.

In a preferred embodiment of the invention, each of $R^2$ and $R^3$ preferably represents a hydrogen atom, the alkyl group mentioned above (a methyl group or a t-butyl group), the aryl group mentioned above (a phenyl group), or a cyano group. Each of $R^2$ and $R^3$ is preferably bonded to p-position of each phenyl group. Each of $R^2$ and $R^3$ is particularly preferably a hydrogen atom.

In formulae (4) and (14), two groups $R^4$ may be the same or different and independently represent a hydrogen atom, a substituted or unsubstituted alkyl group having 1 to 20, preferably 1 to 5, and more preferably 1 to 4 carbon atoms, a substituted or unsubstituted aryl group having 6 to 50, preferably 6 to 24, and more preferably 6 to 12 carbon atoms, a substituted or unsubstituted heterocyclic group having 3 to 50, preferably 3 to 24, and more preferably 3 to 12 ring atoms, a halogen atom, a substituted or unsubstituted fluoroalkyl group having 1 to 20, preferably 1 to 5, and more preferably 1 to 4 carbon atoms, a substituted or unsubstituted alkoxy group having 1 to 20, preferably 1 to 5, and more preferably 1 to 4 carbon atoms, a substituted or unsubstituted fluoroalkoxy group having 1 to 20, preferably 1 to 5, and more preferably 1 to 4 carbon atoms, a substituted or unsubstituted aryloxy group having 6 to 50, preferably 6 to 24, and more preferably 6 to 12 carbon atoms, or a cyano group. When the aromatic amine derivative represented by formula (1) includes the group represented by formula (4) and/or the group represented by formula (14), $R^2$, $R^3$ and $R^4$ may be the same or different.

The groups for two groups $R^4$ are the same as defined above with respect to $R^2$ and $R^3$. In a preferred embodiment of the invention, each of two groups $R^4$ is particularly preferably selected from the alkyl group mentioned above (a methyl group) and the aryl group mentioned above (a phenyl group).

The subscript k represents an integer of 1 to 5, preferably 1 to 3, and more preferably 1.

The subscript m represents an integer of 1 to 4, preferably 1 to 3, and more preferably 1.

The subscript n represents an integer of 1 to 3, preferably to 2, and more preferably 1.

The aromatic amine derivative represented by formula (1) is preferably represented by formula (20):

(20)

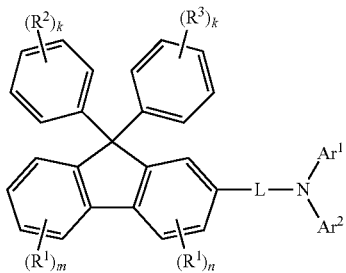

wherein Ar¹, Ar², R¹ to R³, k, m, and n are the same as defined in formula (1).

When the fluorene skeleton is directly bonded to the nitrogen atom as shown in formula (20), the ionization potential of the aromatic amine derivative is lowered. Therefore, the energy barrier of a light emitting layer to an anode or a hole injecting layer is reduced to facilitate the electron injection to the light emitting layer, thereby reducing the driving voltage of an organic EL device.

Ar¹ is preferably a group selected from formulae (21) to (25):

(21)

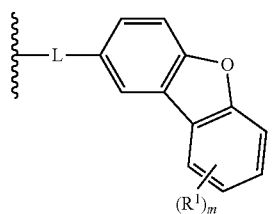

(22)

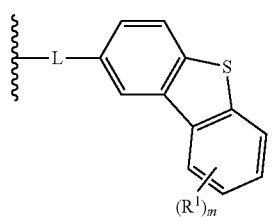

(23)

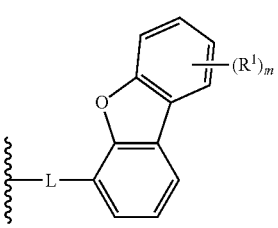

(24)

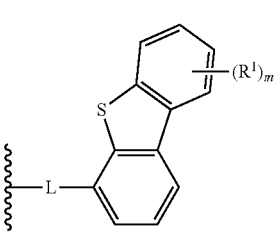

(25)

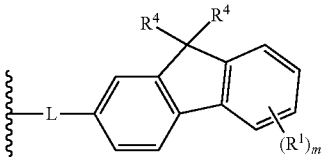

wherein L, $R^1$, $R^4$, and m are the same as defined in formulae (2) to (4).

Ar¹ is more preferably a group selected from formulae (26) to (30).

(26)

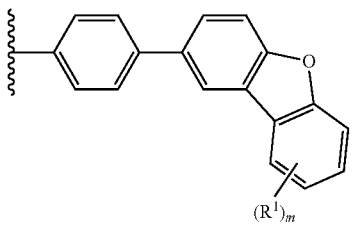

(27)

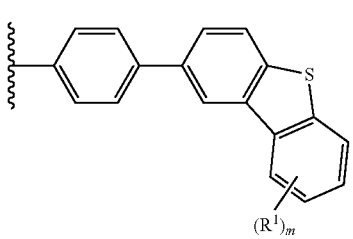

(28)

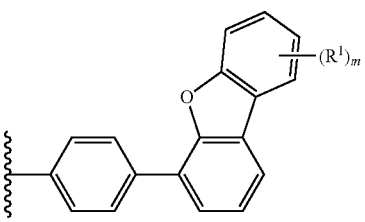

(29)

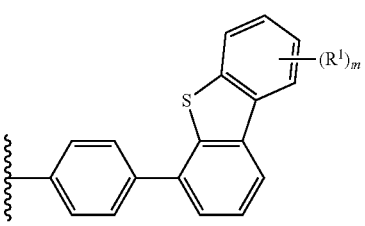

(30)

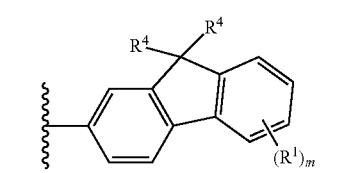

wherein $R^1$, $R^4$, and m are the same as defined in formulae (2) to (4).

In formulae (21) to (30), when L or the phenylene group is bonded to the clibenzofuran skeleton or the dibenzothiophene skeleton at o-position with respect to the oxygen atom or the sulfur atom, the lifetime is expected to be improved, while the efficiency is expected to be improved when bonded at p-position with respect to the oxygen atom or the sulfur atom. When L or the phenylene group is bonded to 2-position of the fluorene skeleton, the driving voltage is expected to be reduced.

The group represented by any of formulae (26) to (30) partly includes a p-biphenyl structure. The p-position of the benzene ring directly bonded to the central nitrogen atom is a portion with a high electron density and an electrochemically weak portion. In contrast, by the p-biphenyl structure, i.e., by protecting the p-position of the benzene ring with a phenyl group, the stability of the compound is improved and the deterioration of the material is prevented, and therefore, the lifetime of an organic EL device is prolonged.

Each of formulae (7), (8) and (9) for Ar$^2$ is preferably represented by any of formulae (7-1), (7-2), (8-1), and (9-1):

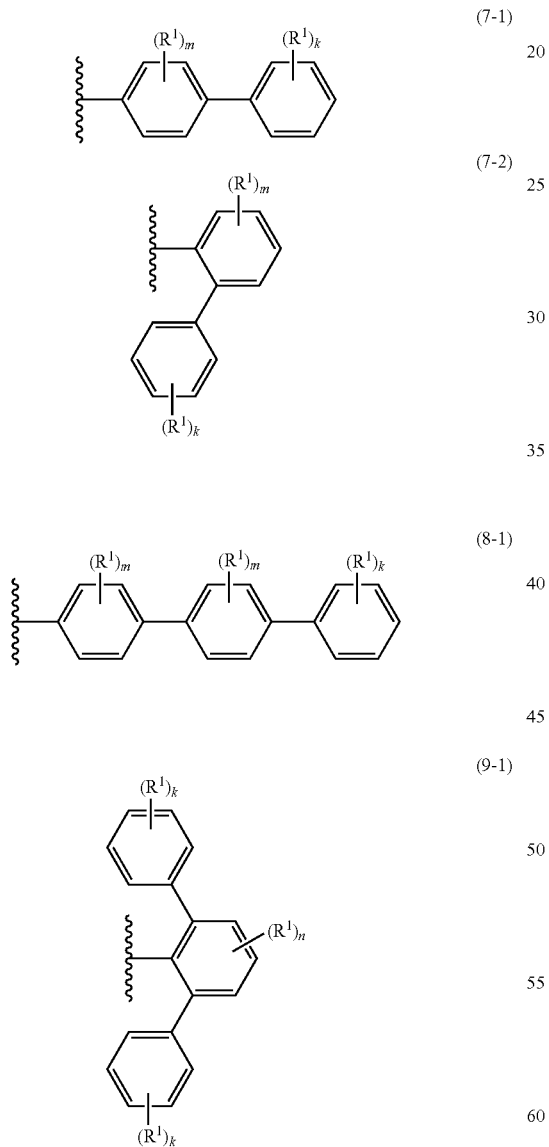

wherein R$^1$, k, m, and n are the same as defined in formulae (7), (8) and (9).

Each of formulae (12), (13) and (14) for Ar$^2$ is preferably represented by any of formulae (31) to (35):

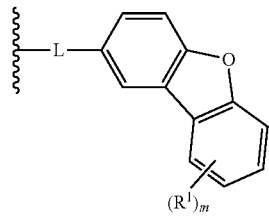

(31)

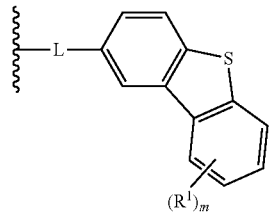

(32)

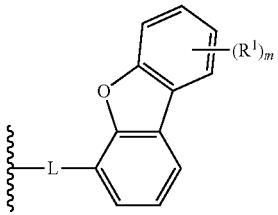

(33)

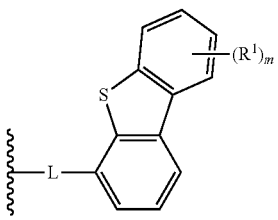

(34)

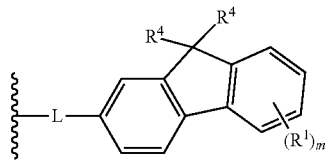

(35)

in formulae (31) to (35), R$^1$, R$^4$, L, and m are the same as defined in formulae (12) to (14), and more preferably represented by any of formulae (36) to (40):

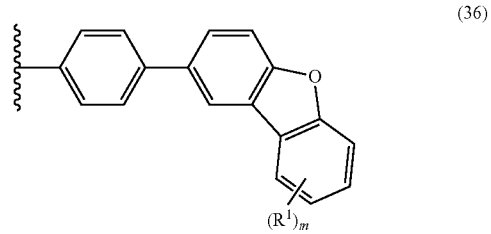

(36)

(37)
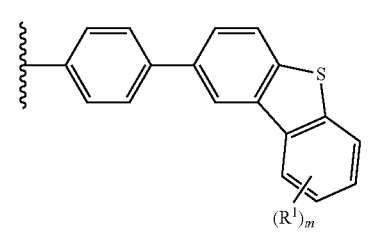
(38)
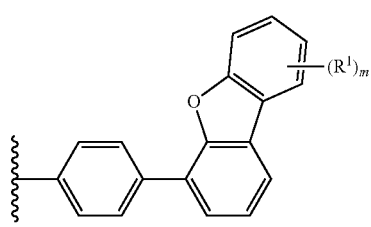
(39)
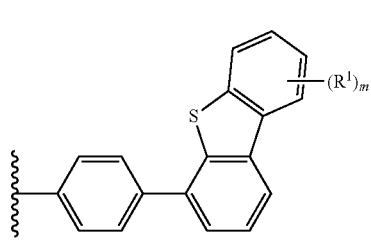
(40)
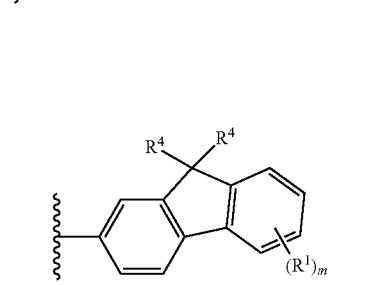
in formulae (31) to (35), $R^1$, $R^4$ and m are the same as defined in formulae (2) to (4).
Examples of the aromatic amine derivative represented by formula (1) are shown below, although not limited to the following compounds.
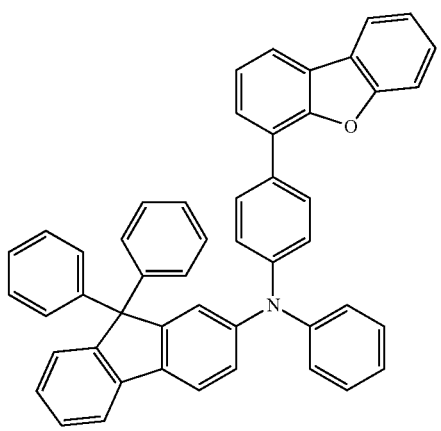
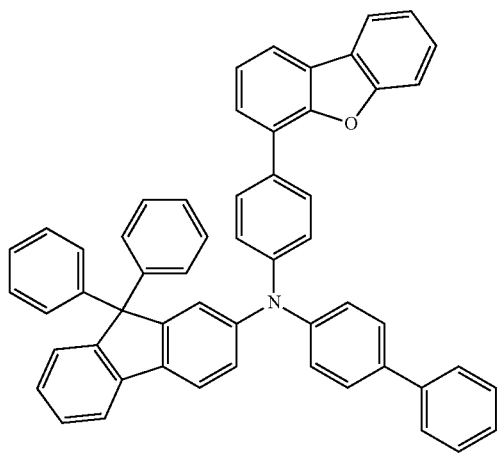
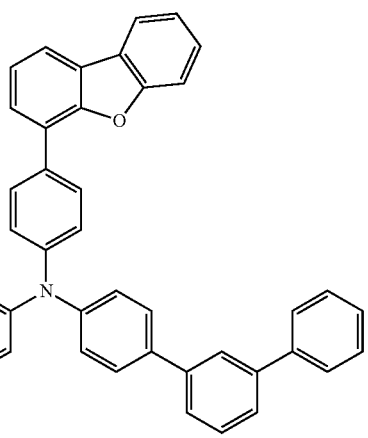

19
-continued
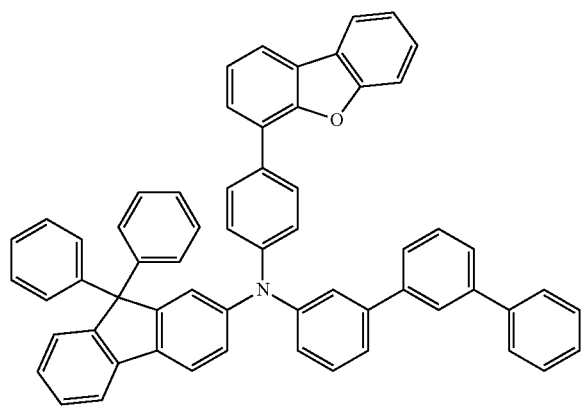
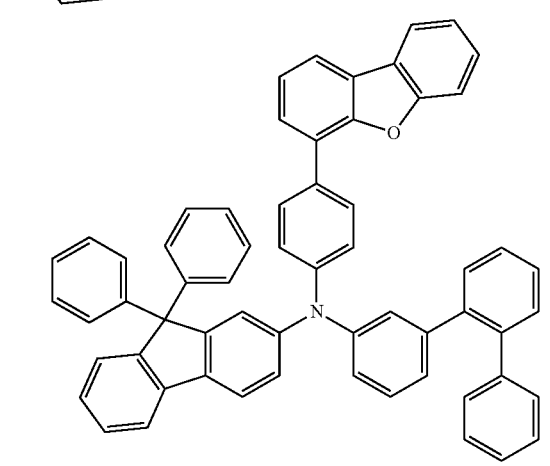
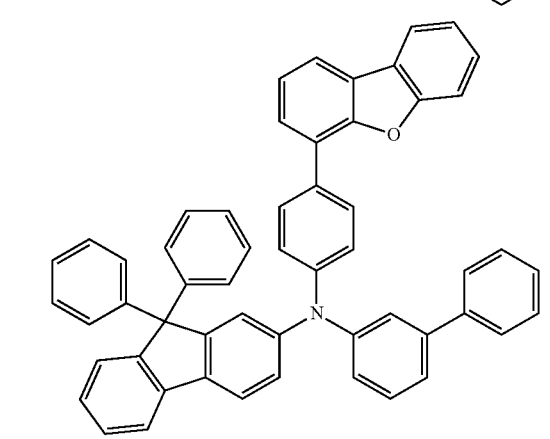
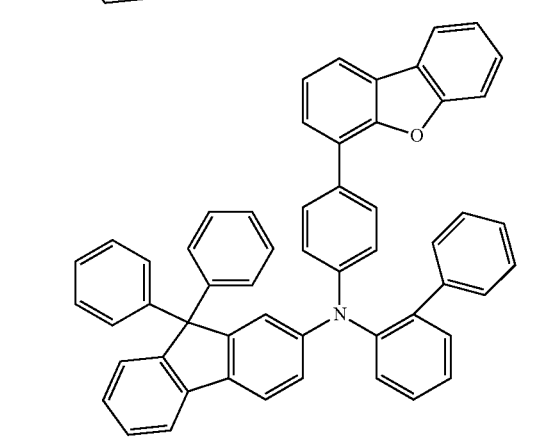
20
-continued
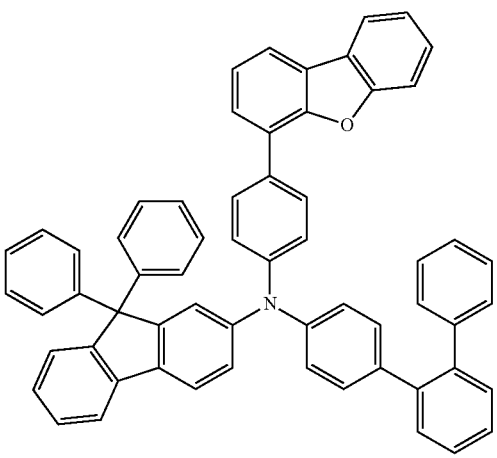
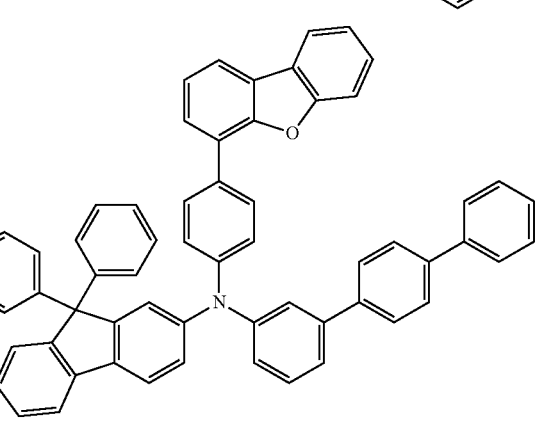
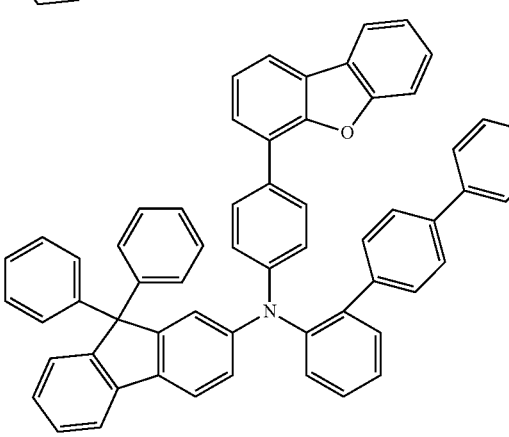
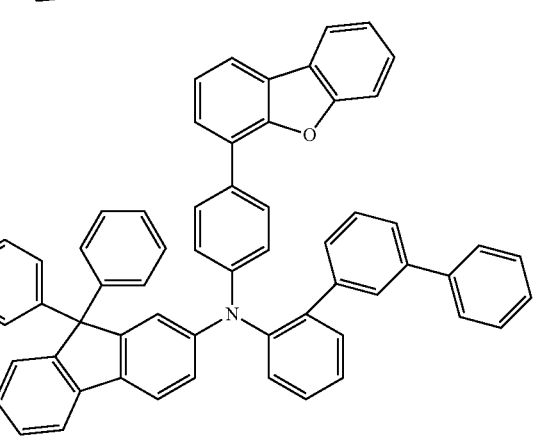

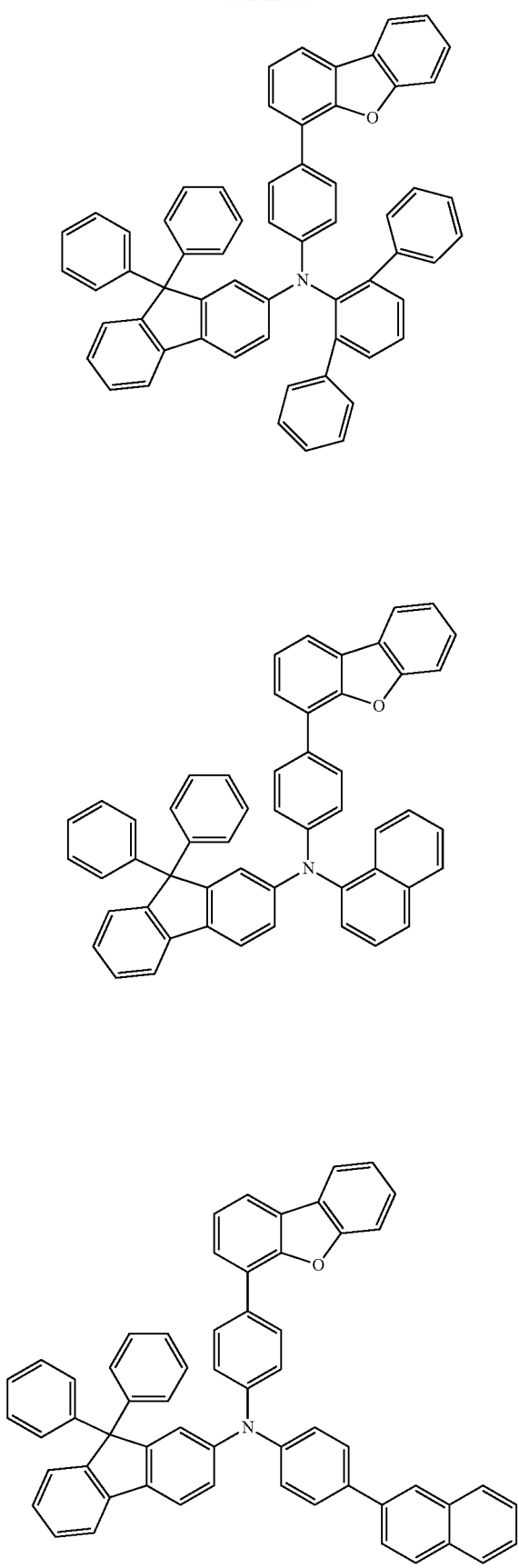
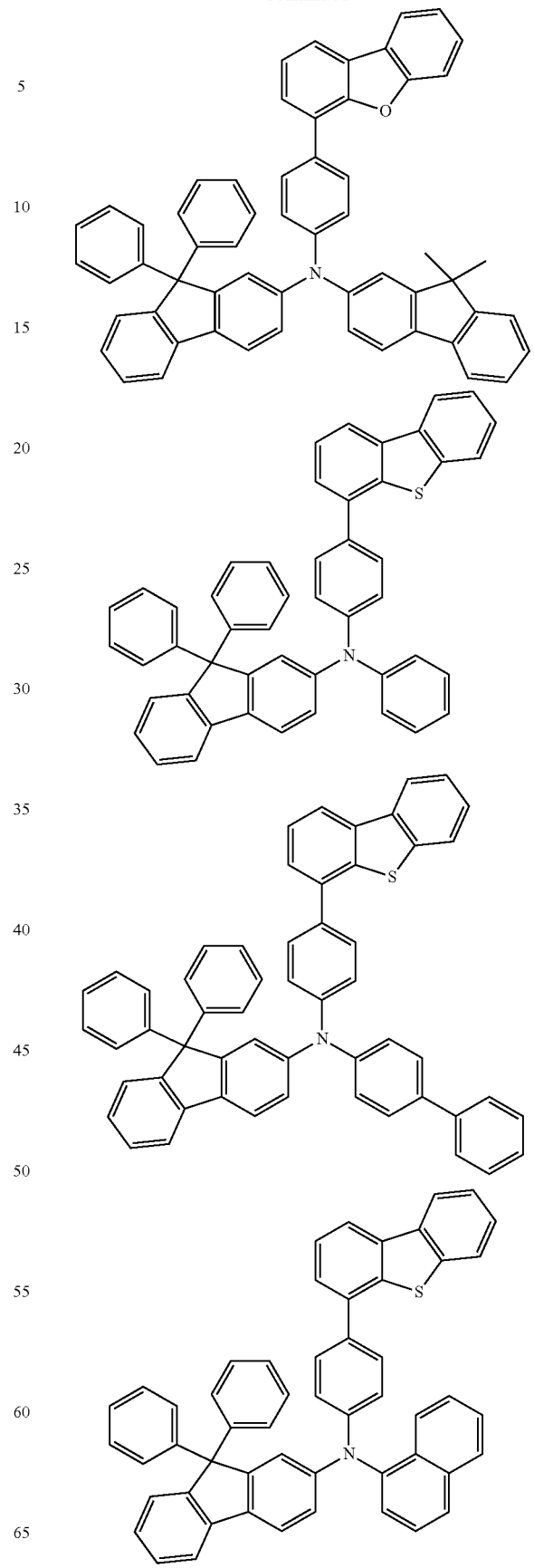

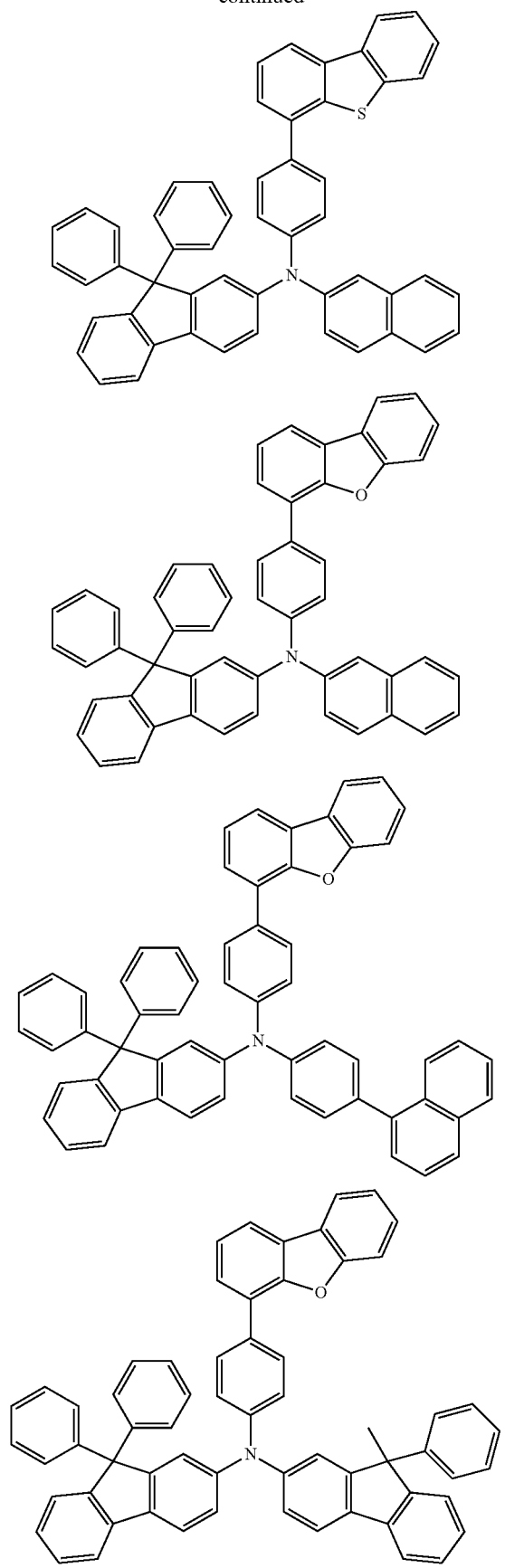
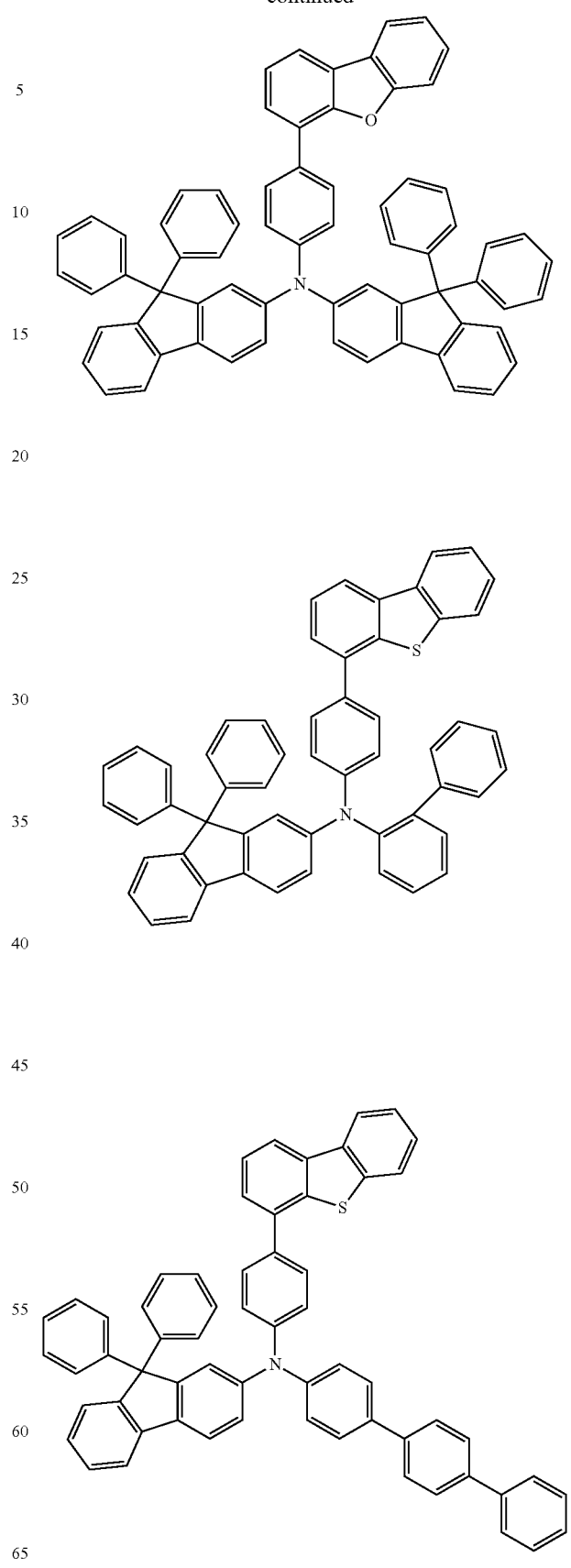

25
-continued
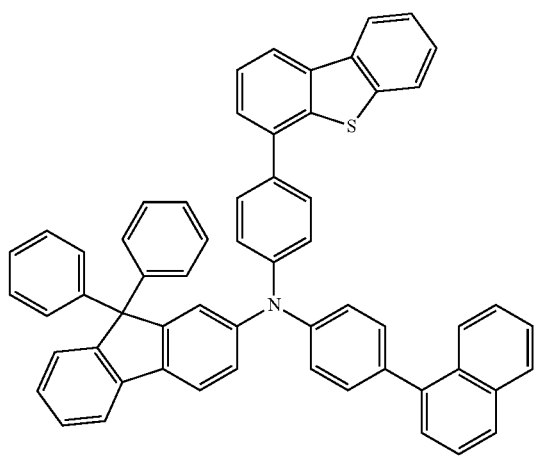
26
-continued
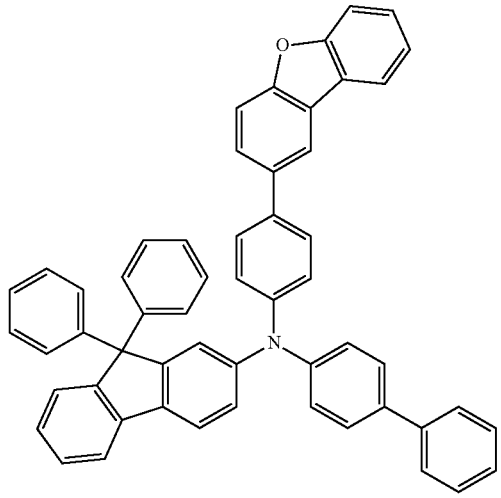
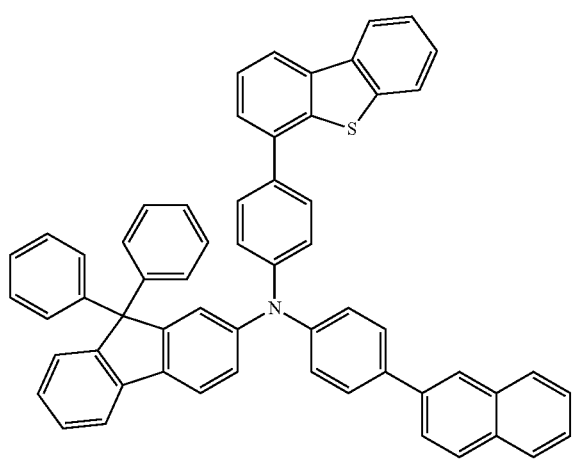
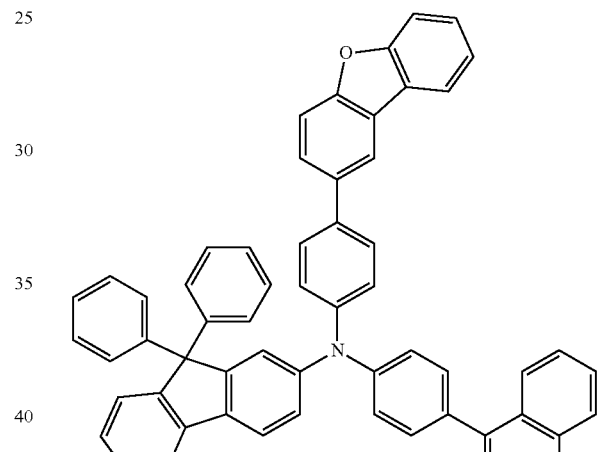
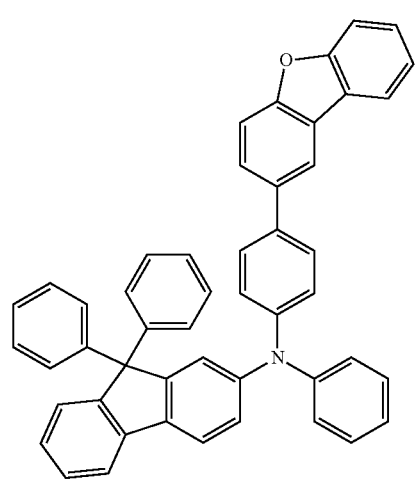
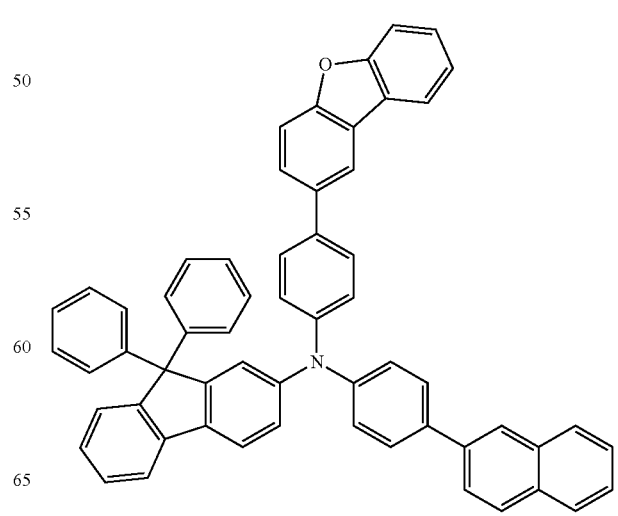

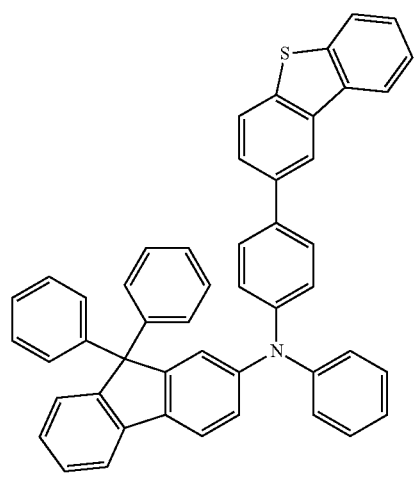
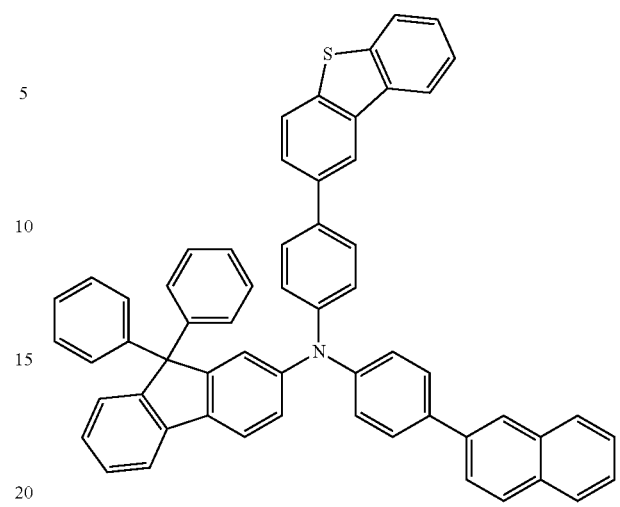
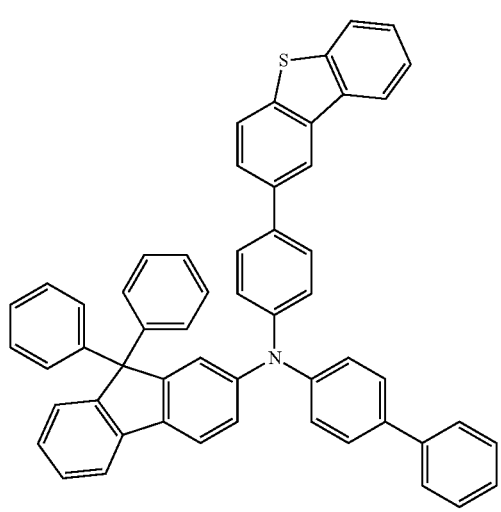
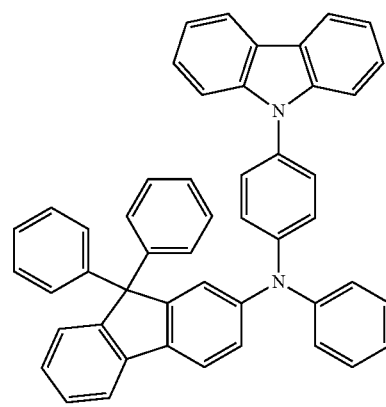
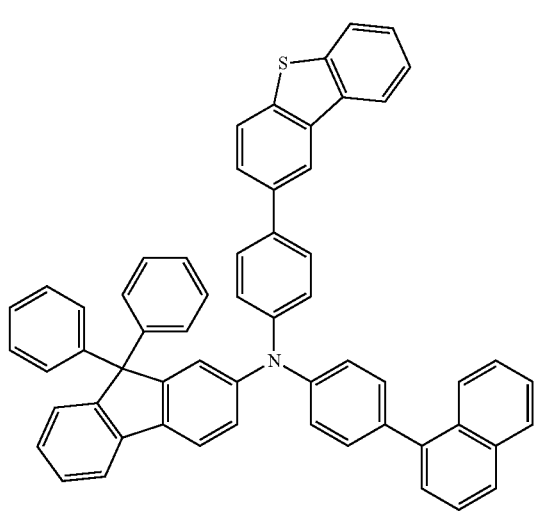
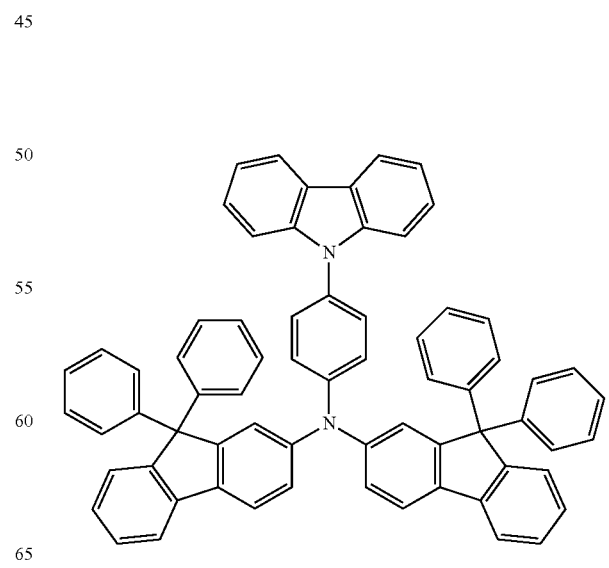

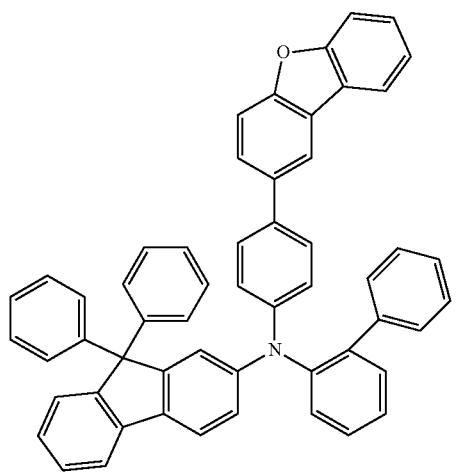
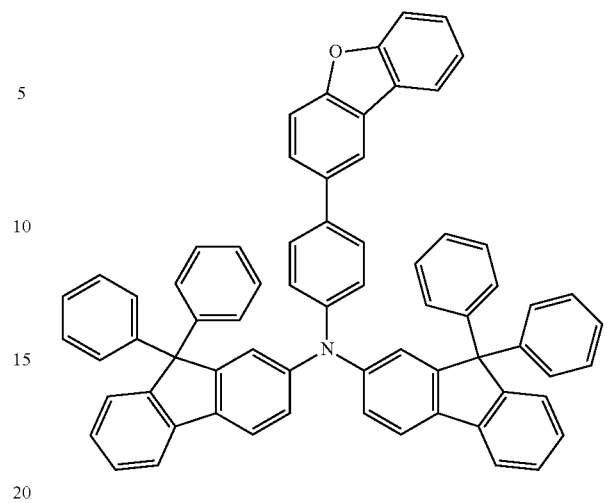
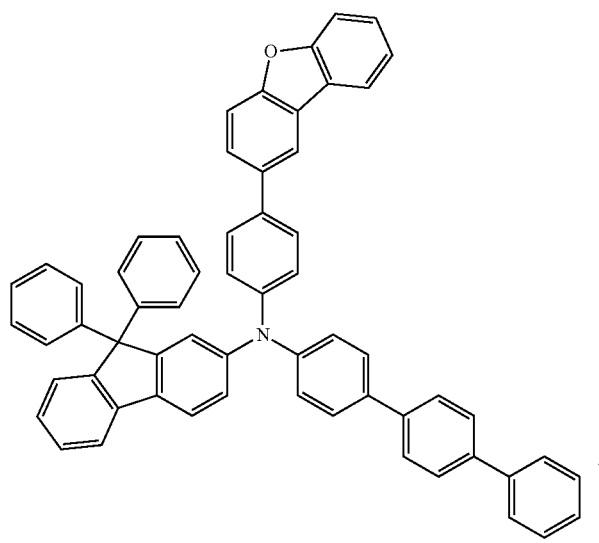
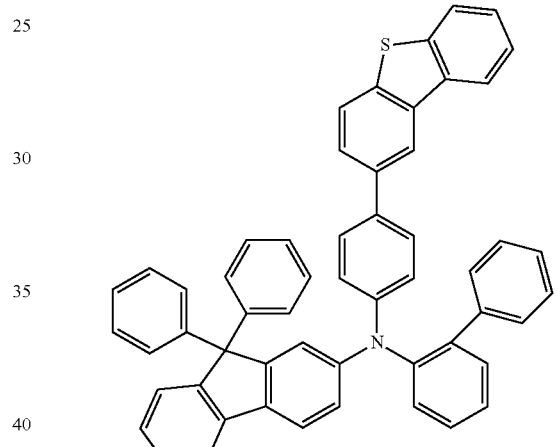
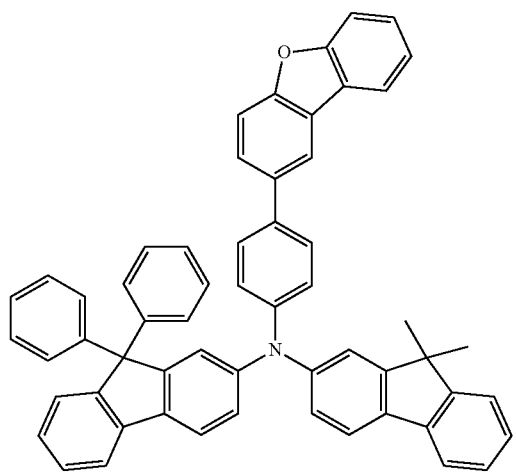
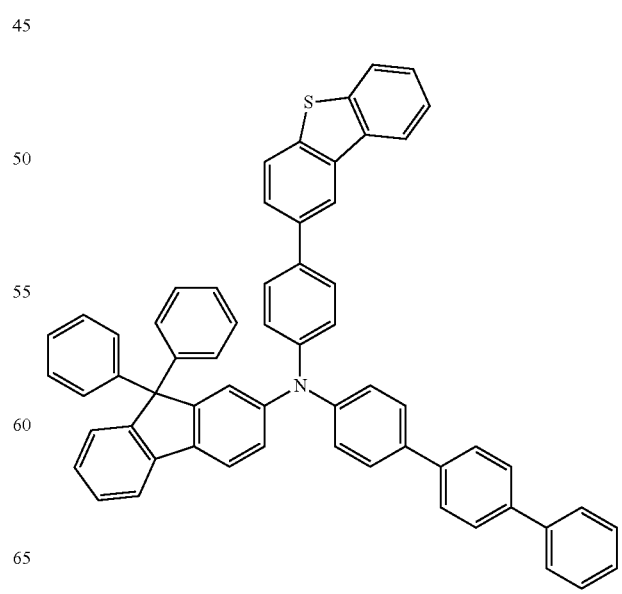

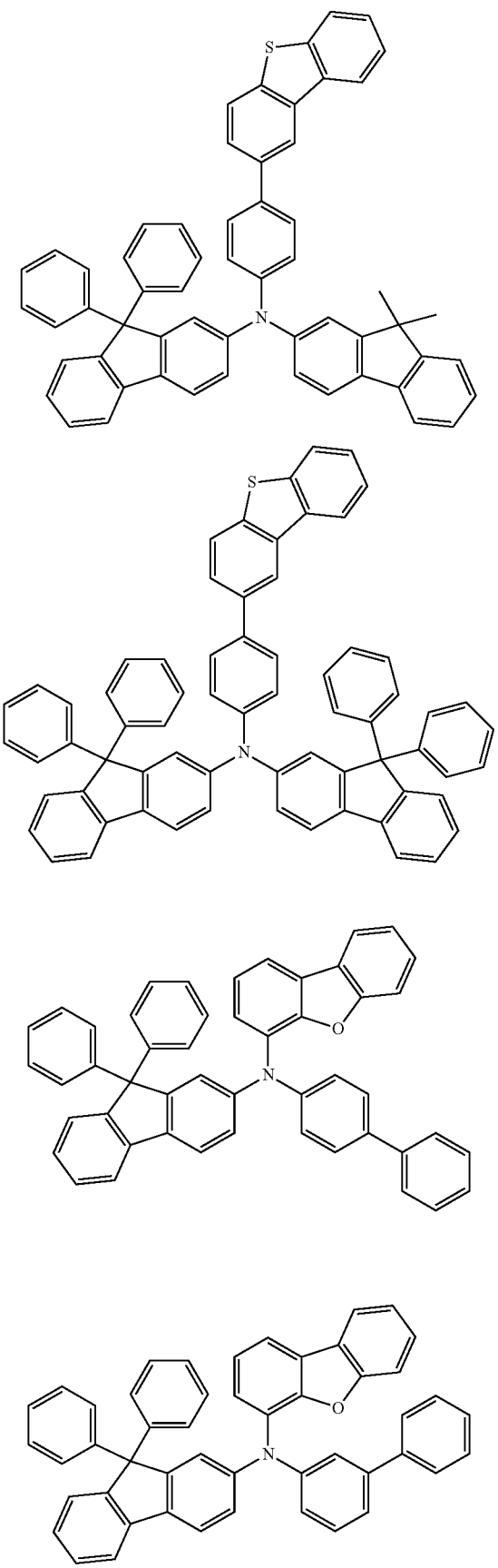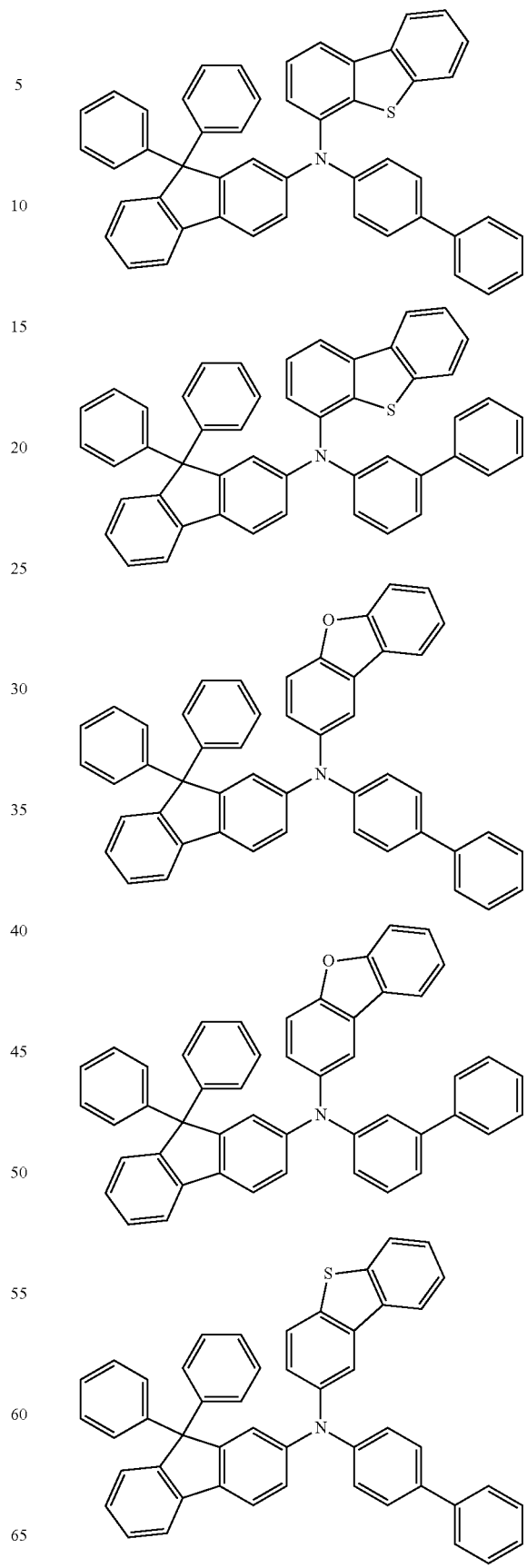

-continued
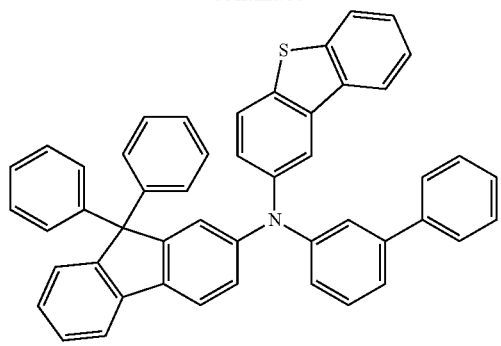
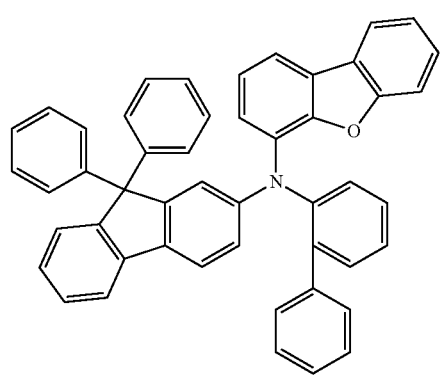
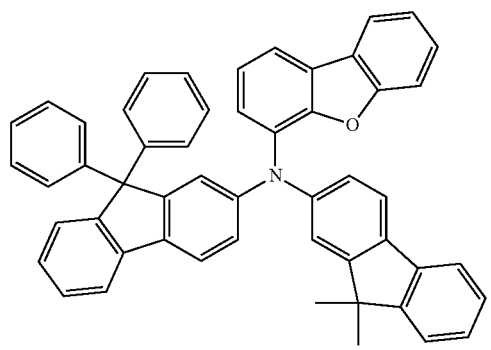
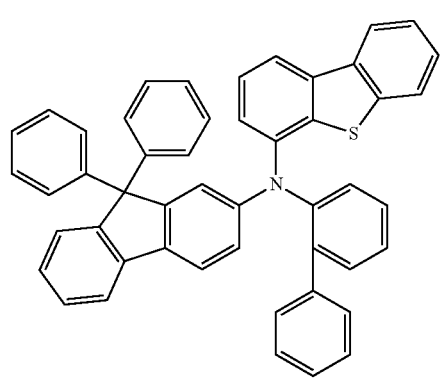
-continued
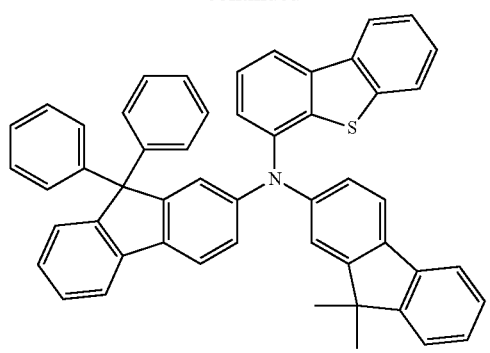
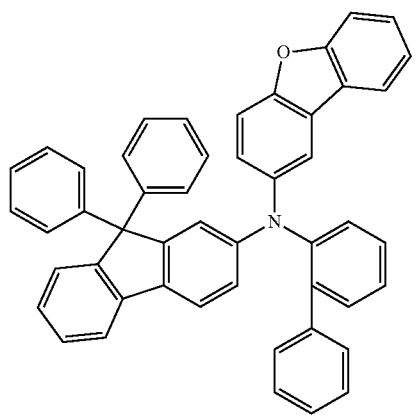
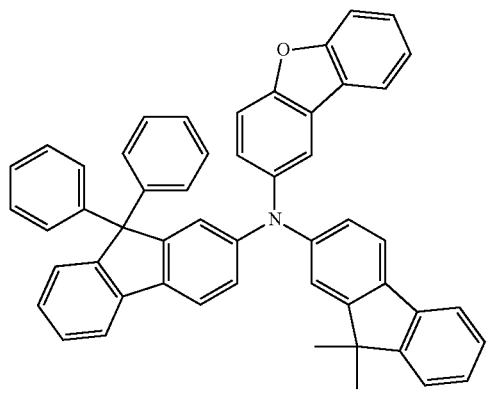
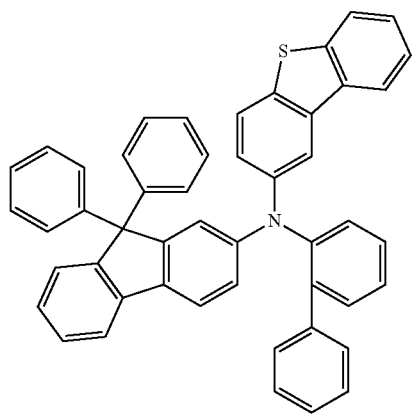

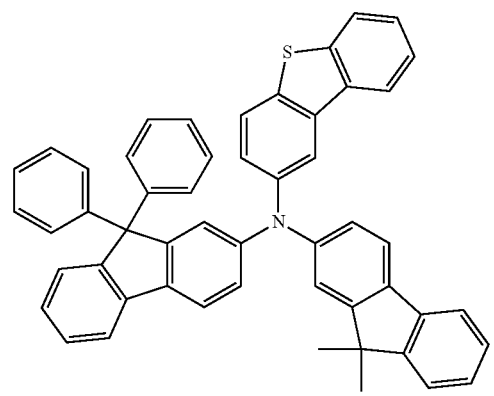
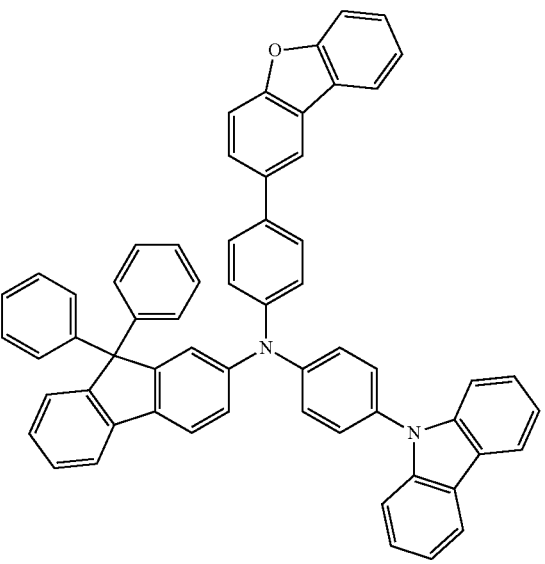
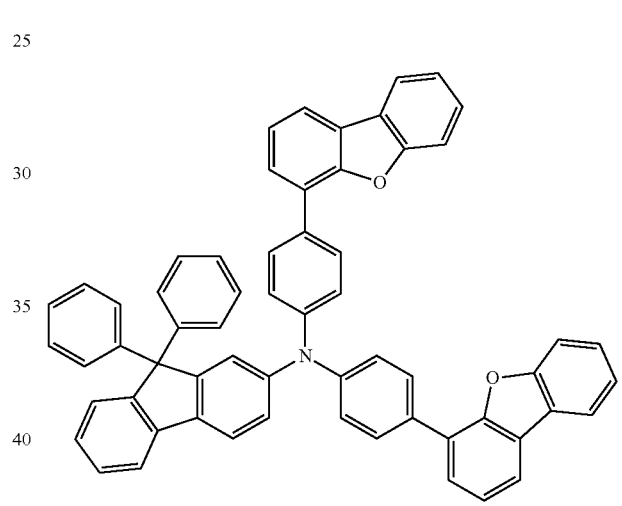
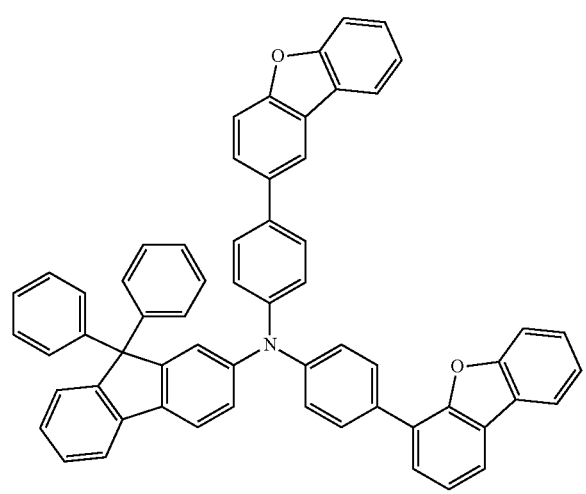
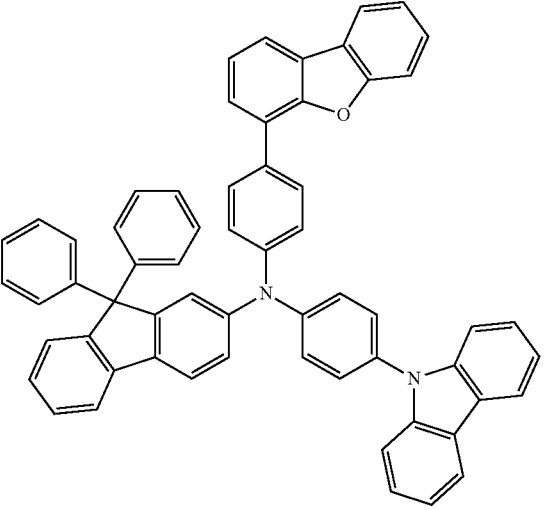

| 37 -continued | 38 -continued |
|---|---|
| 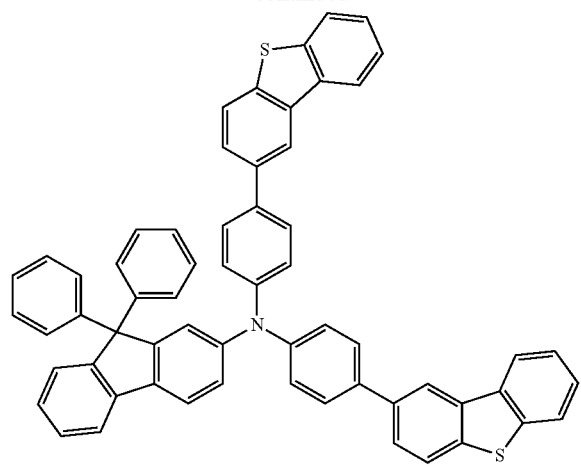 | 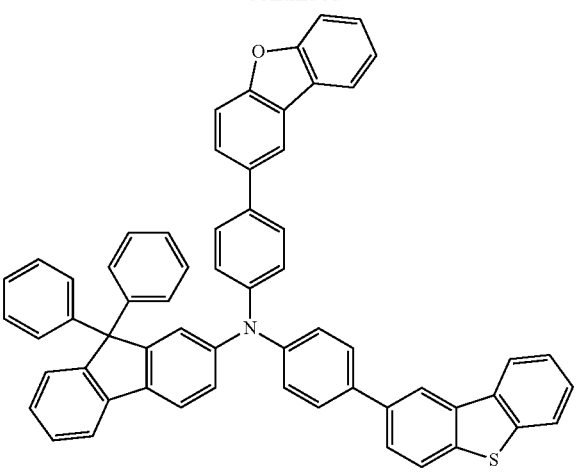 |
| 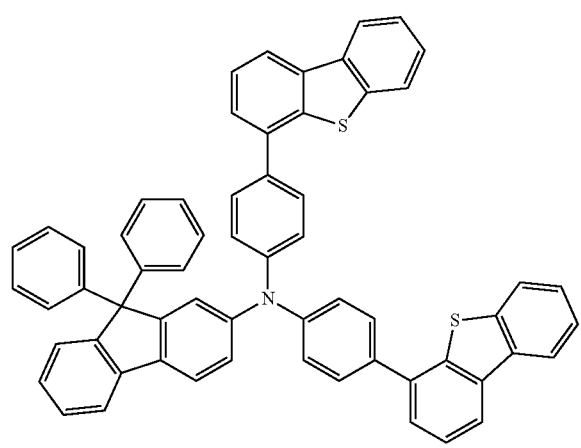 | 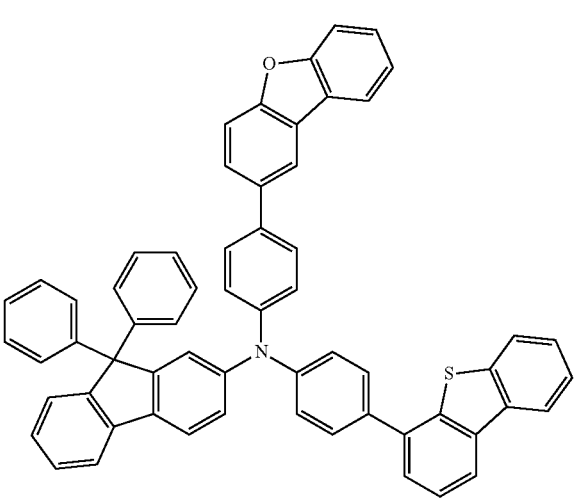 |
| 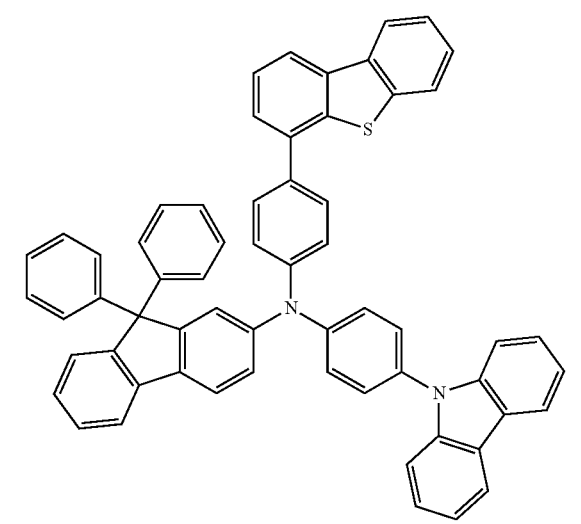 | 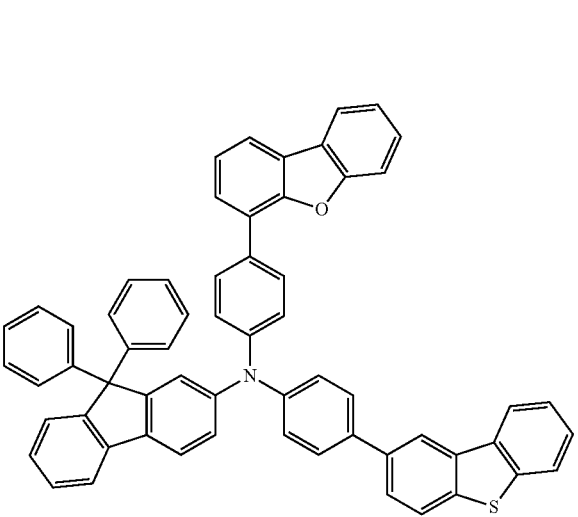 |

39
-continued
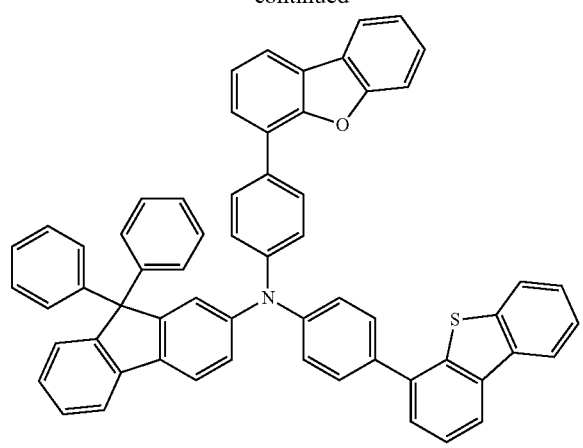
40
-continued
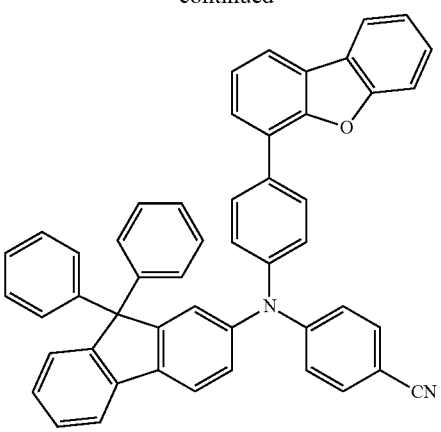
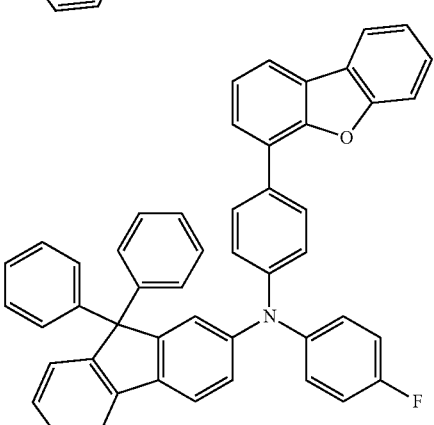
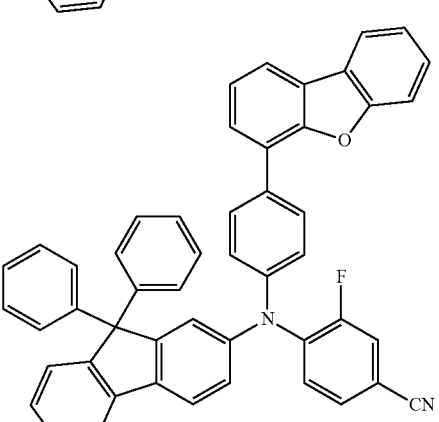
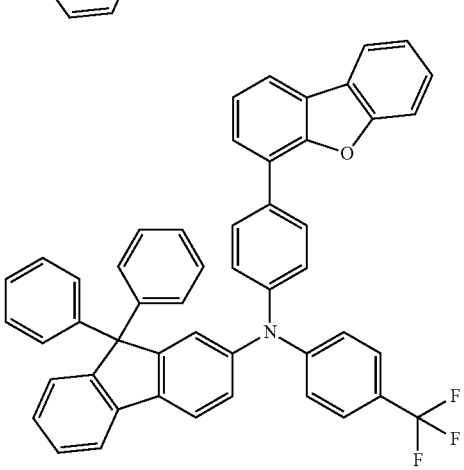

-continued
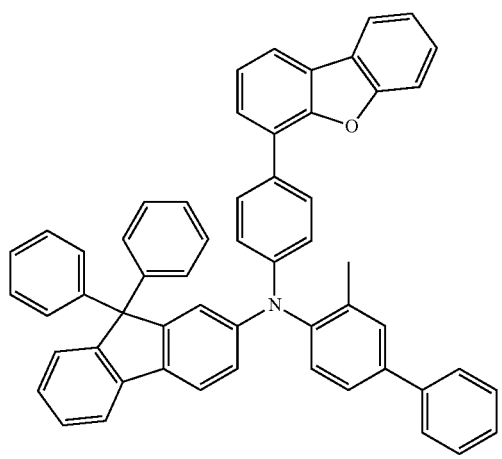
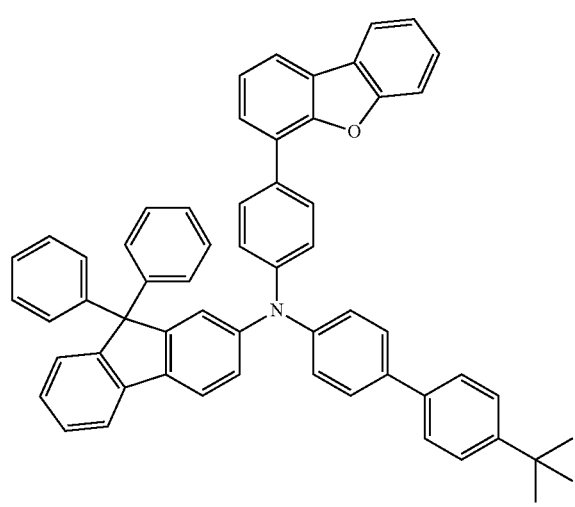
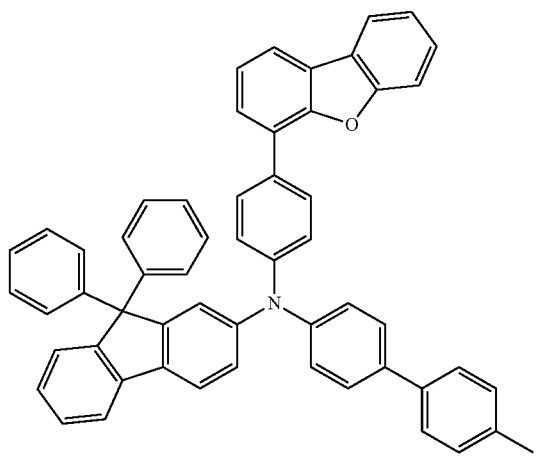
-continued
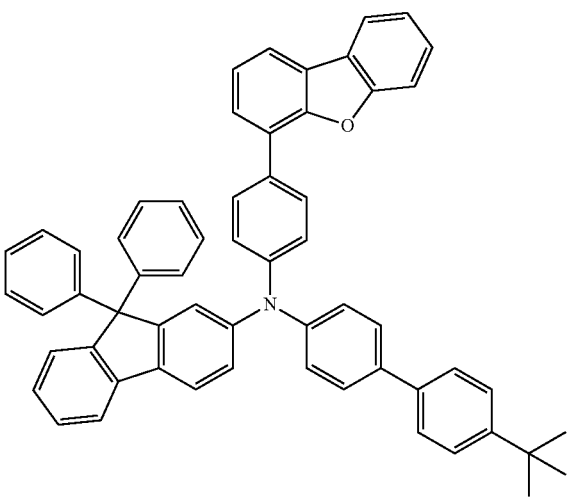
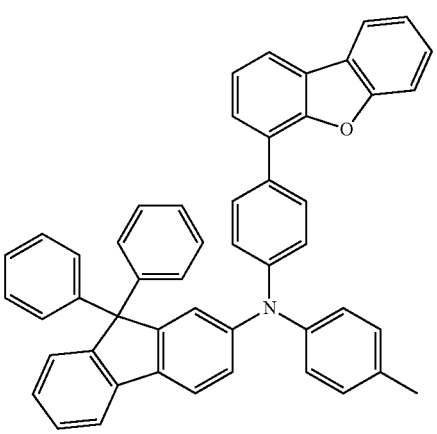
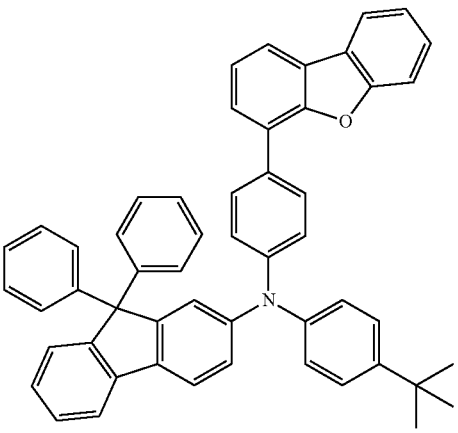

-continued
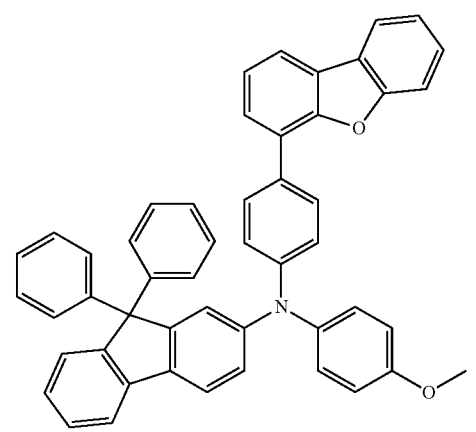
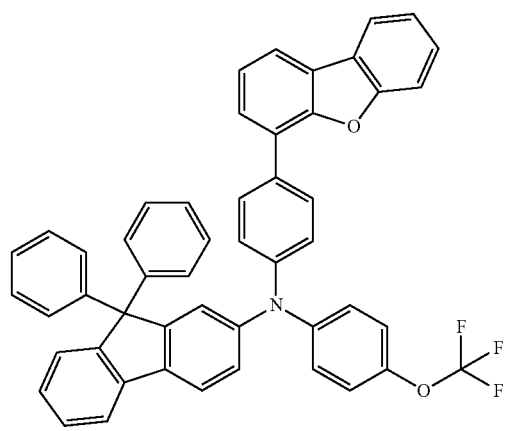
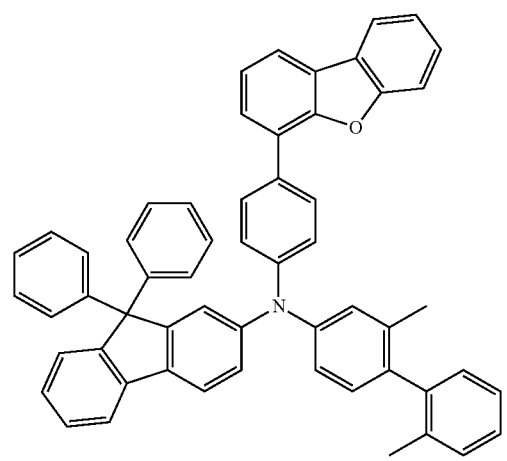
-continued
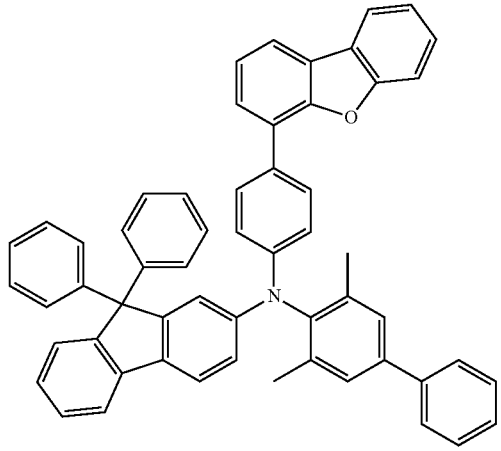
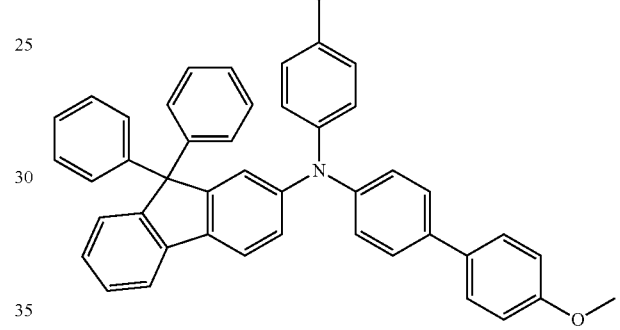
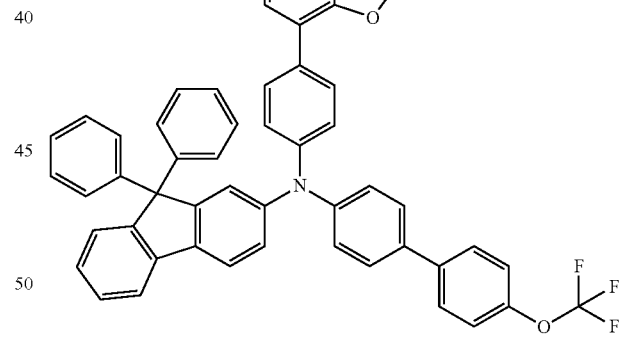
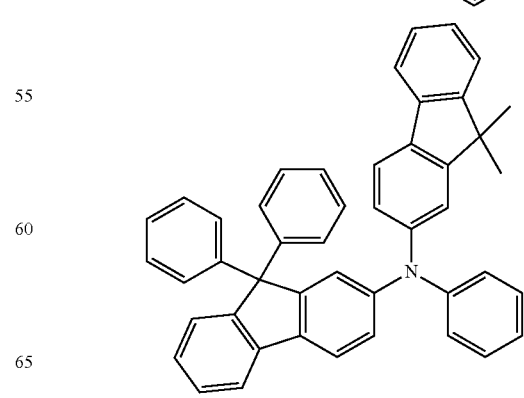

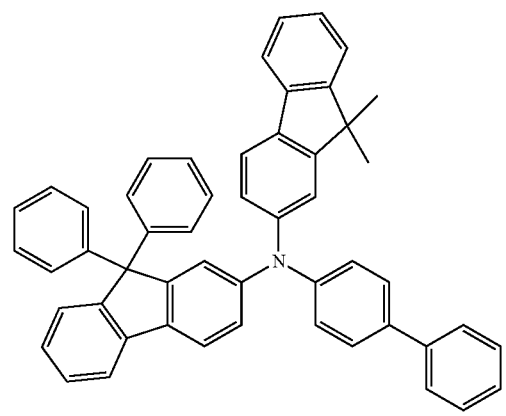
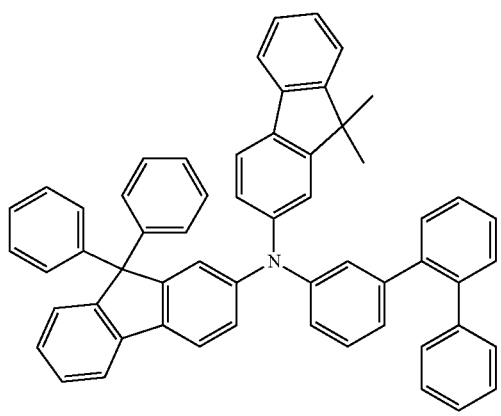

-continued
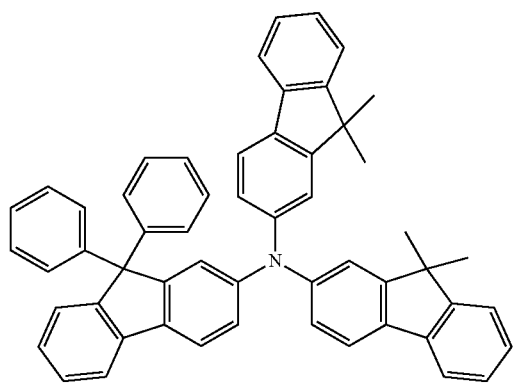
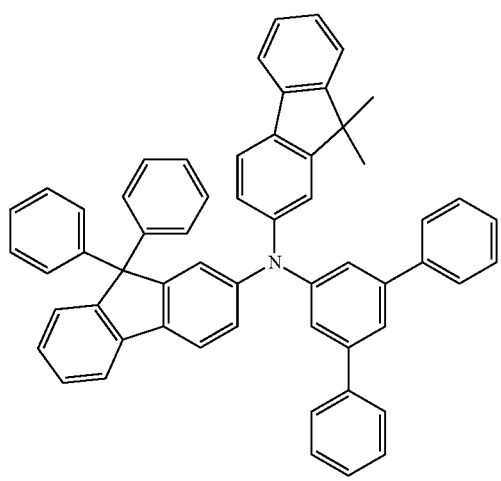
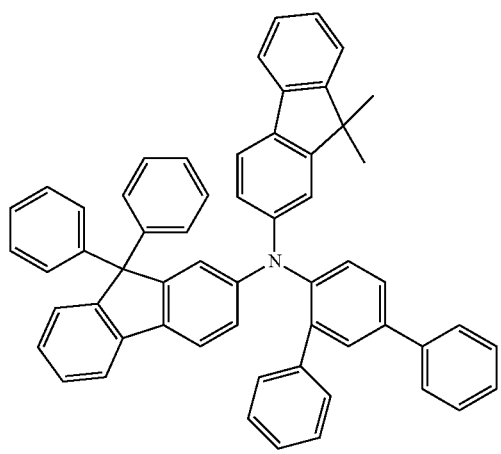
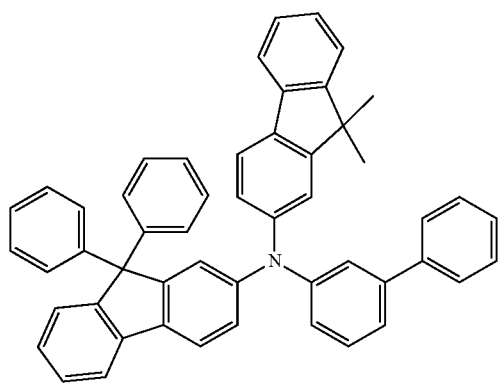
-continued
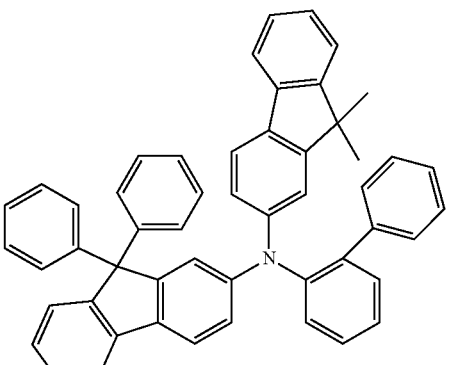
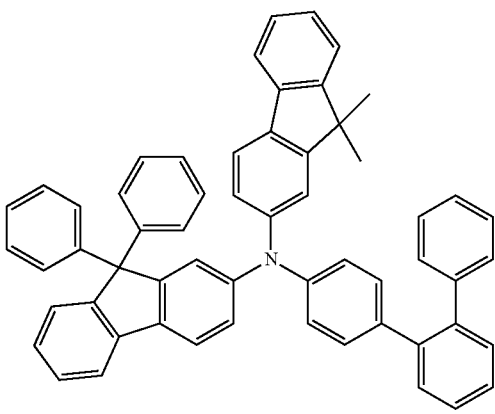
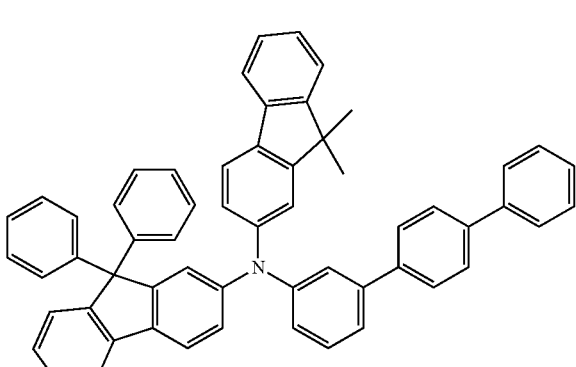
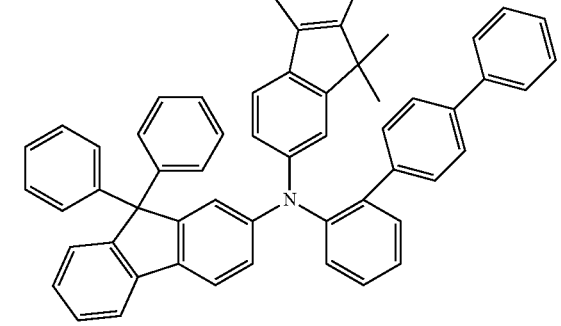

-continued
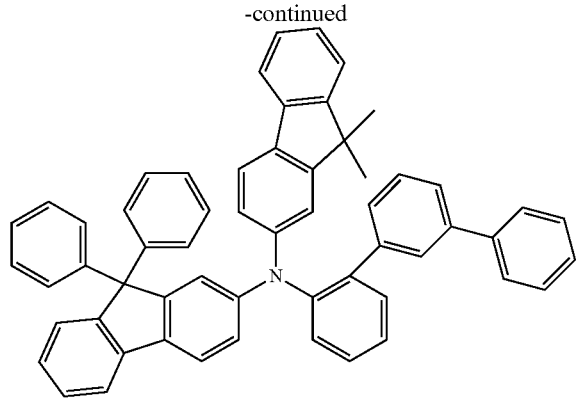
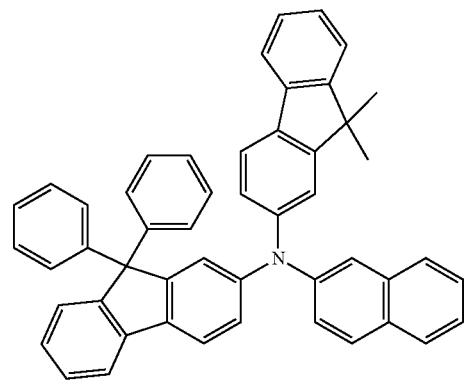
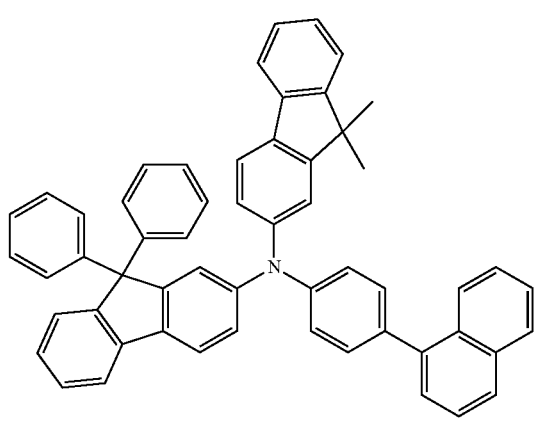
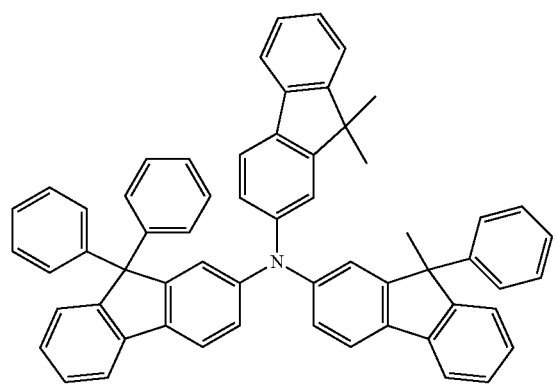
-continued
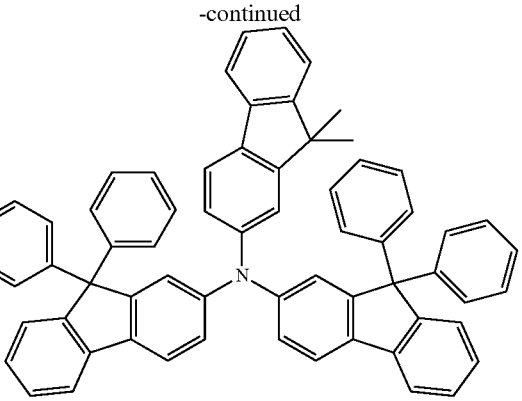
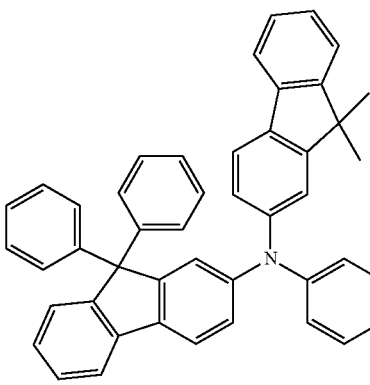
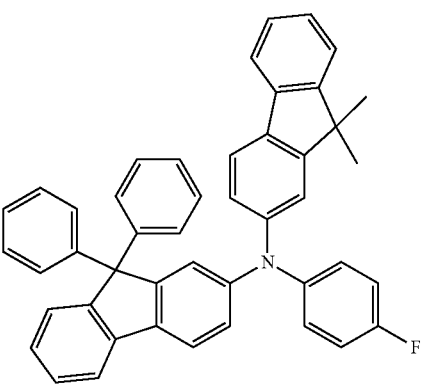
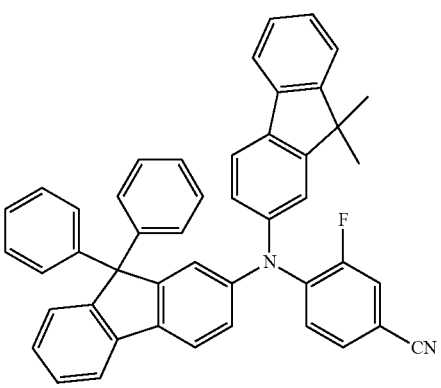

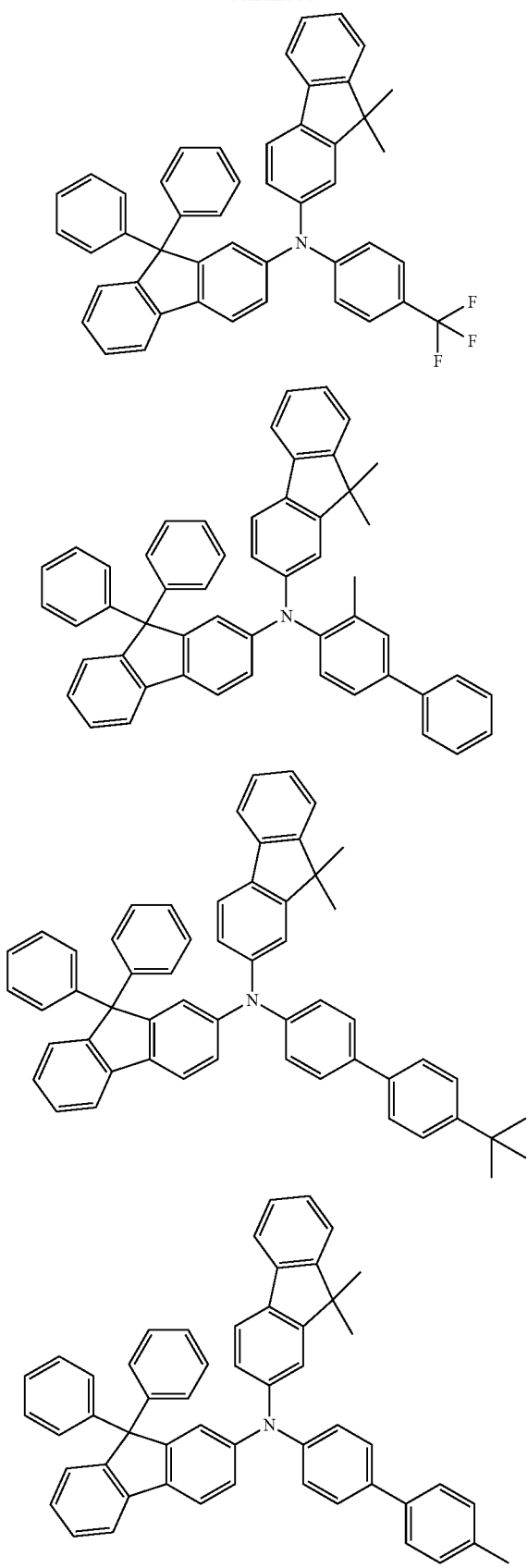
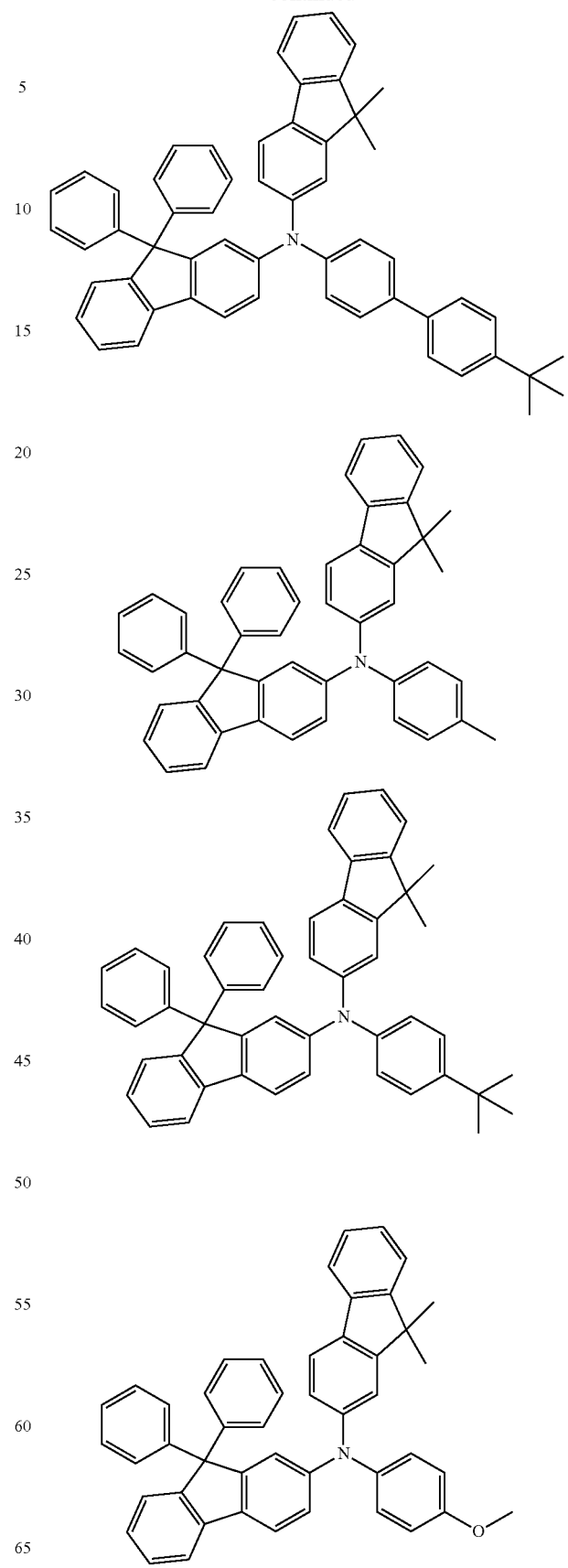

53
-continued
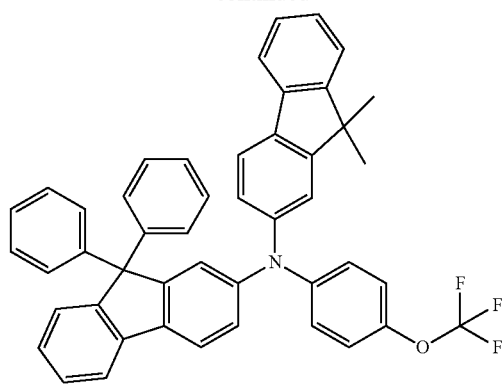
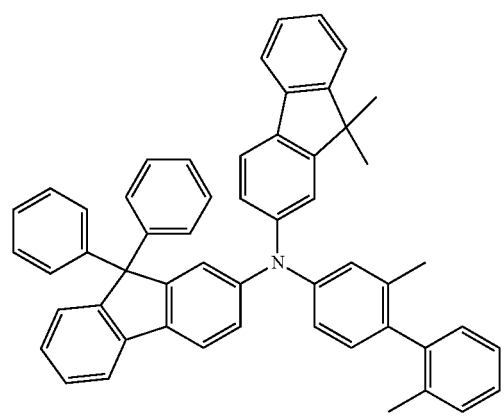
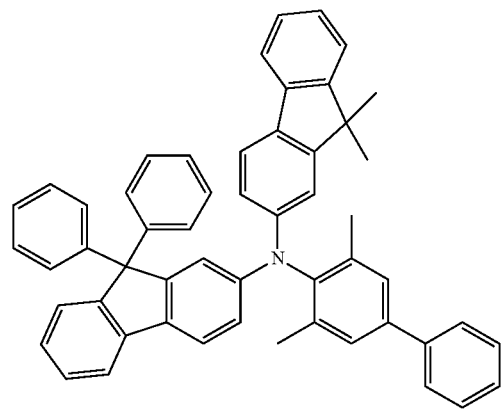
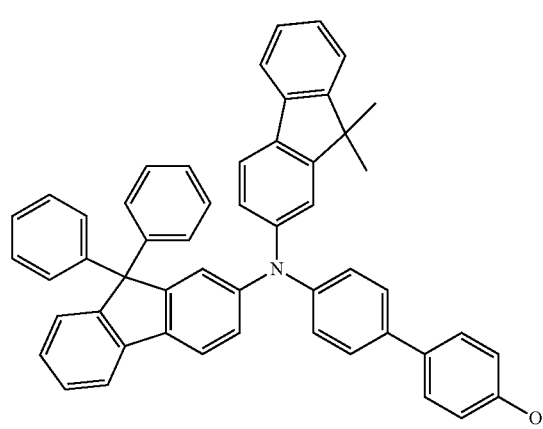
54
-continued
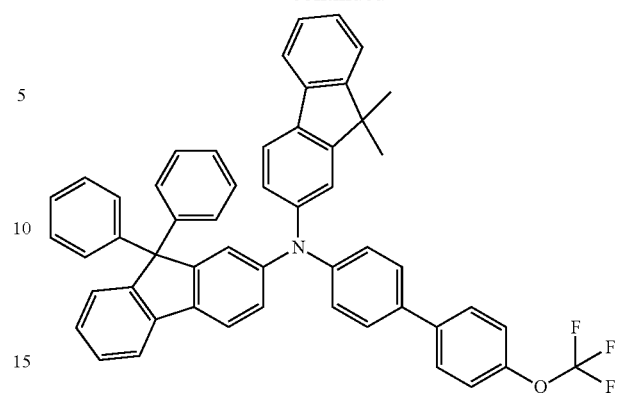
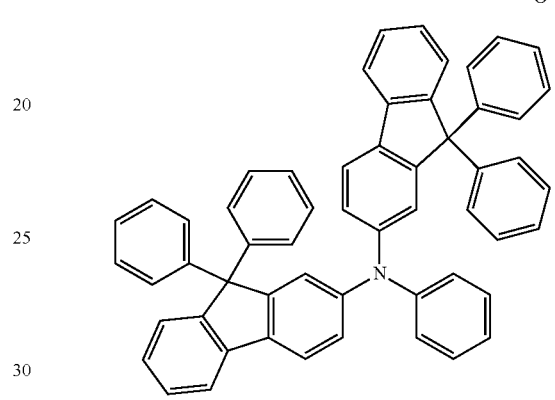
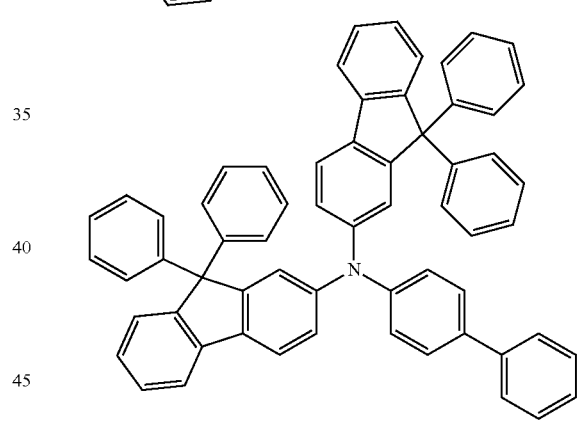
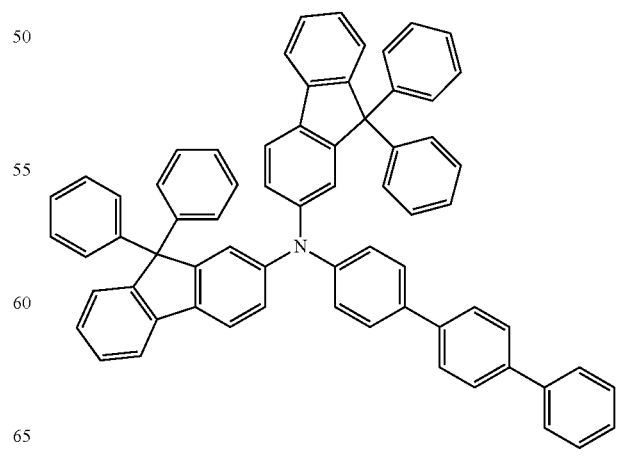

-continued
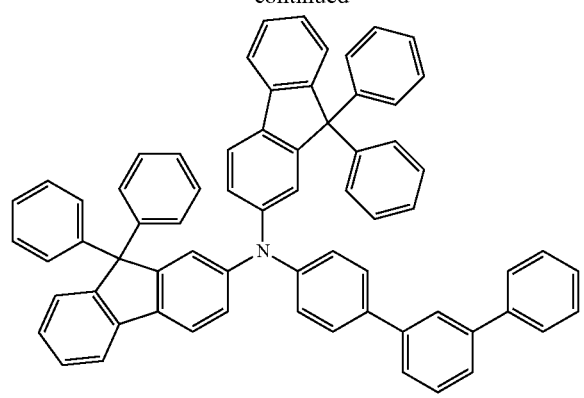
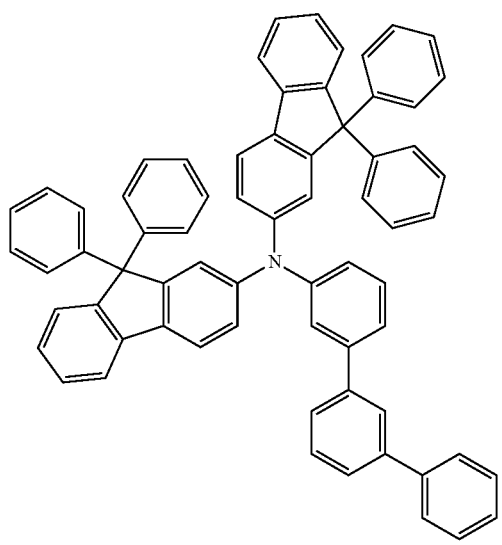
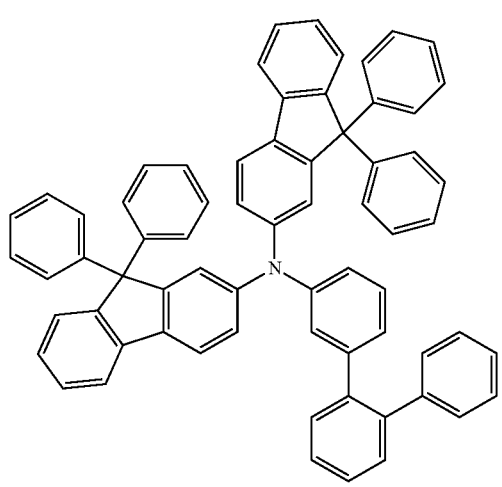
-continued
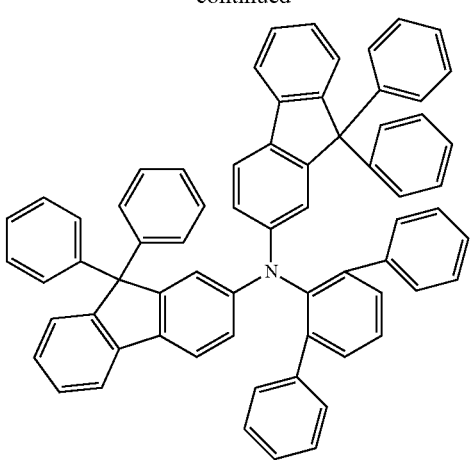
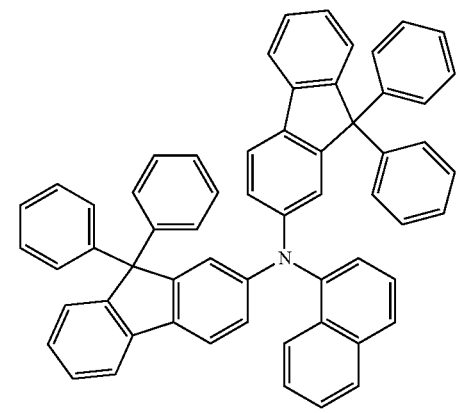
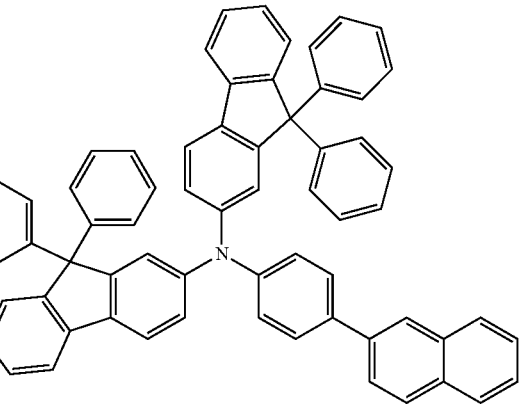
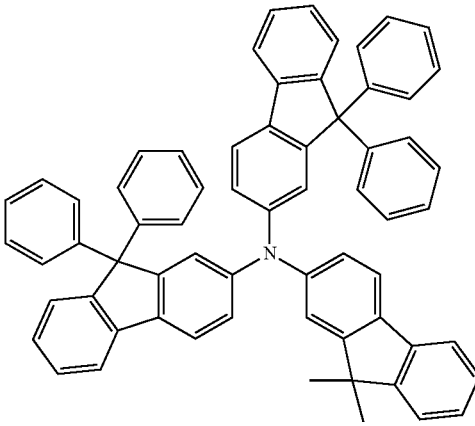

57
-continued
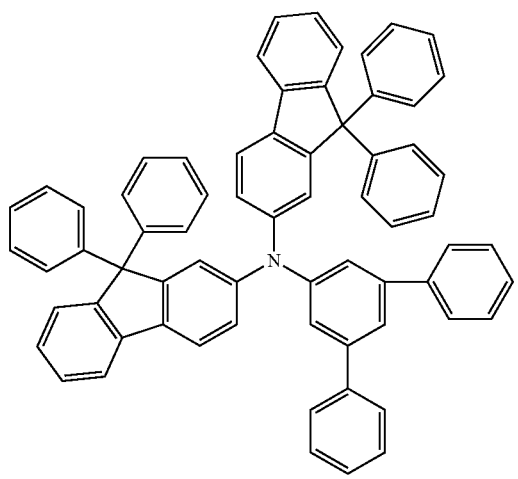
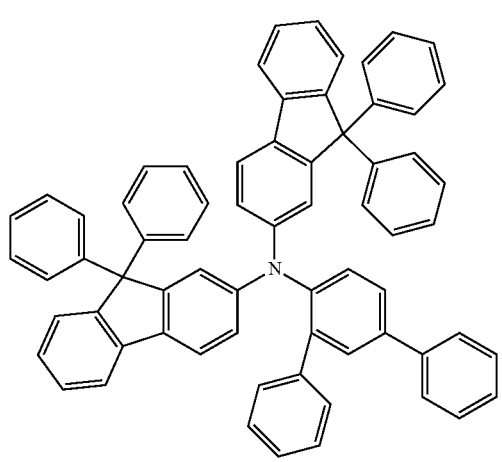
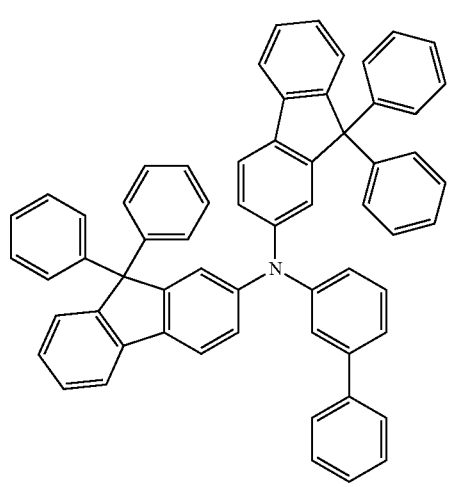
58
-continued
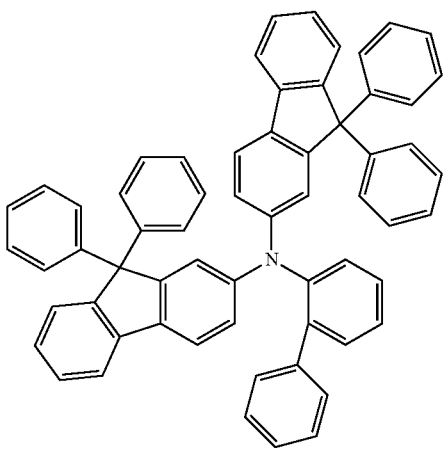
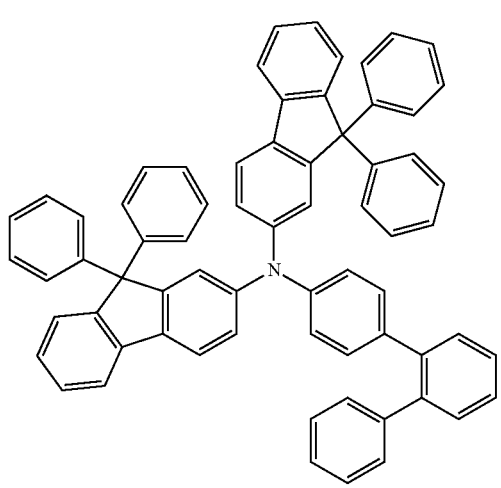
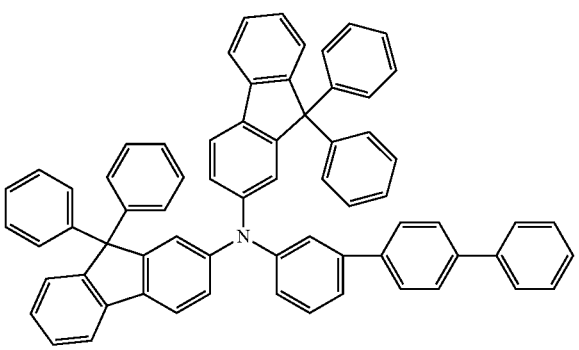

-continued

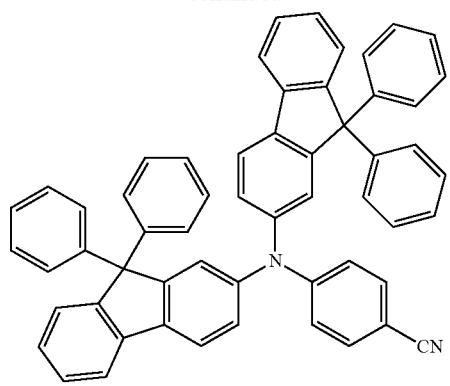
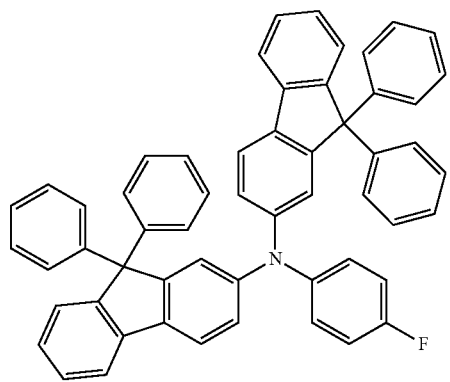
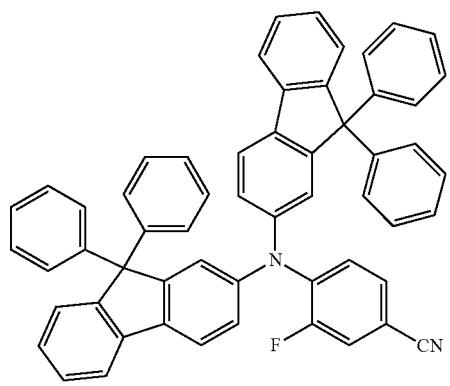
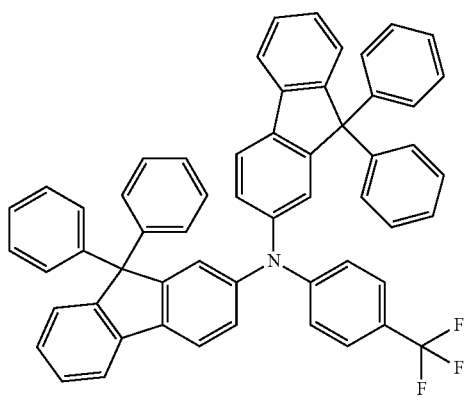
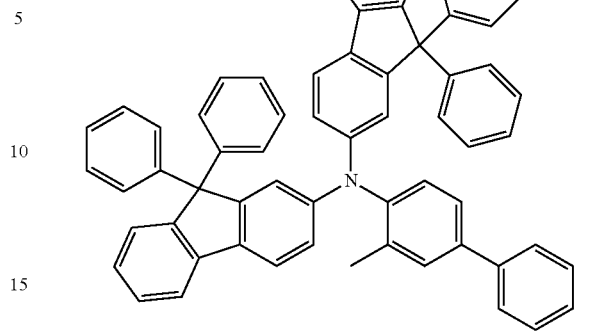
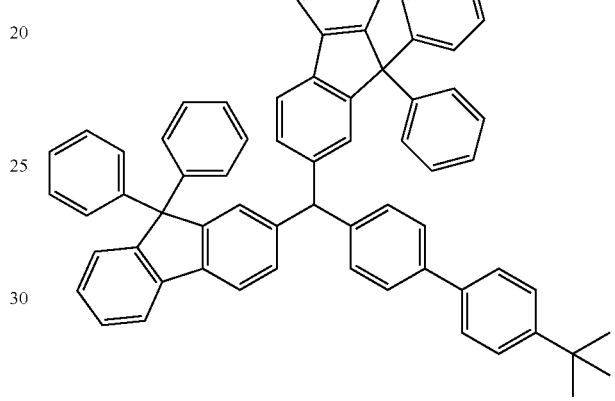
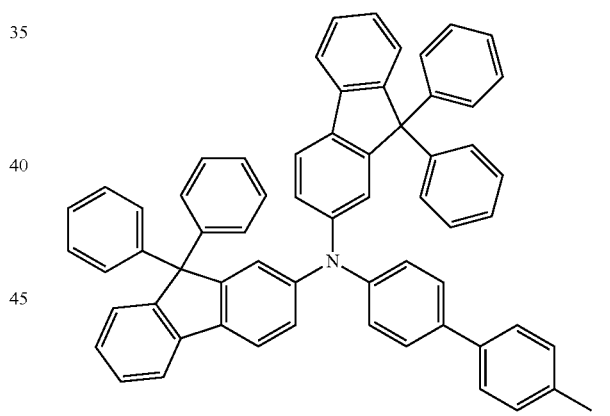
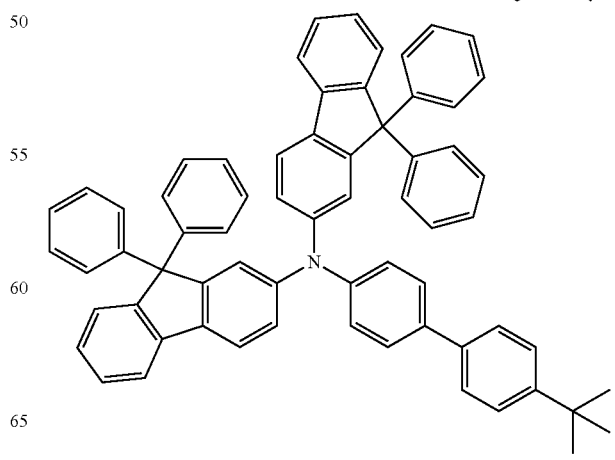

63
-continued
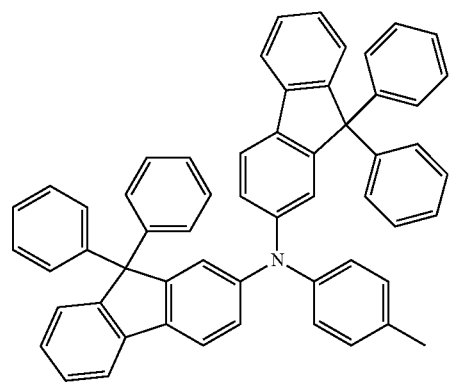
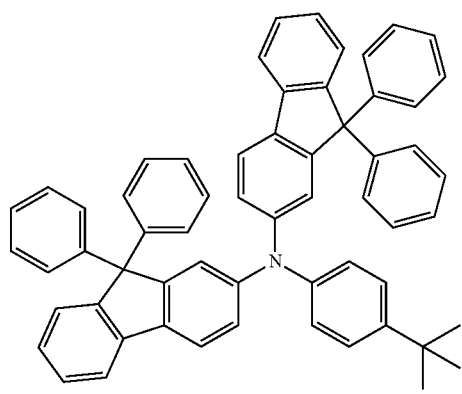
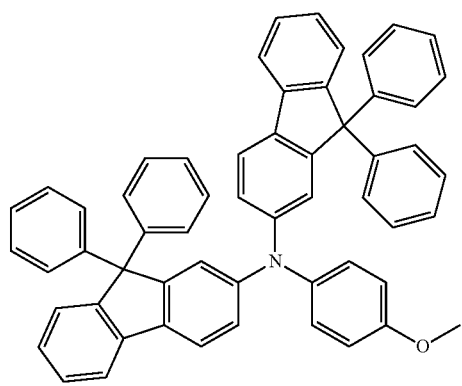
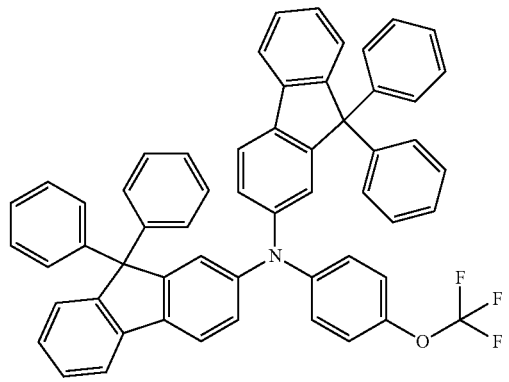
64
-continued
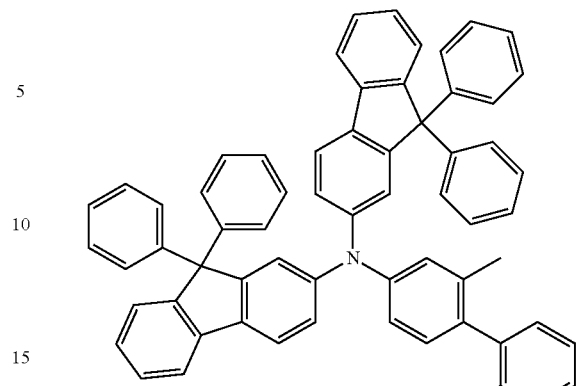
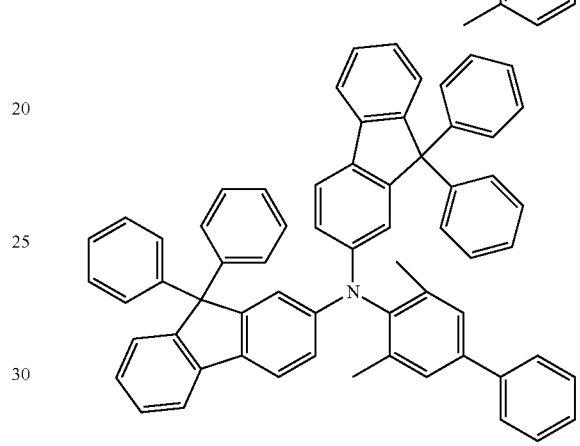
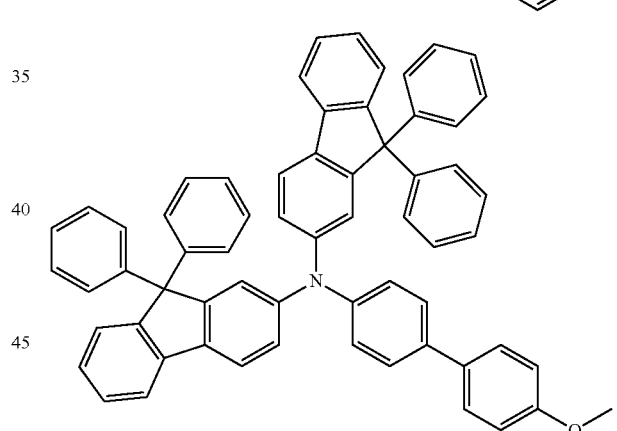
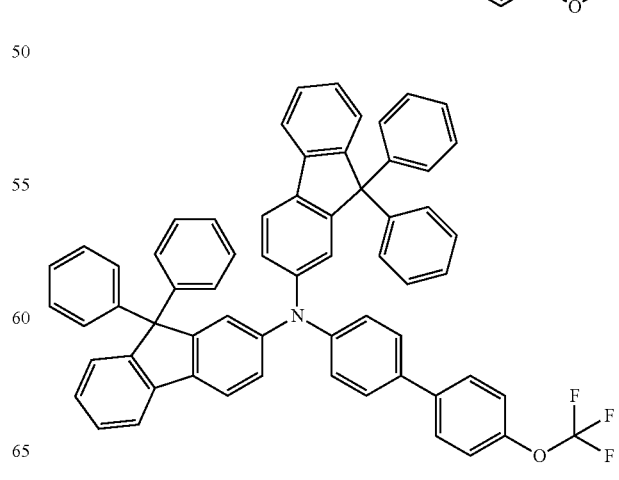

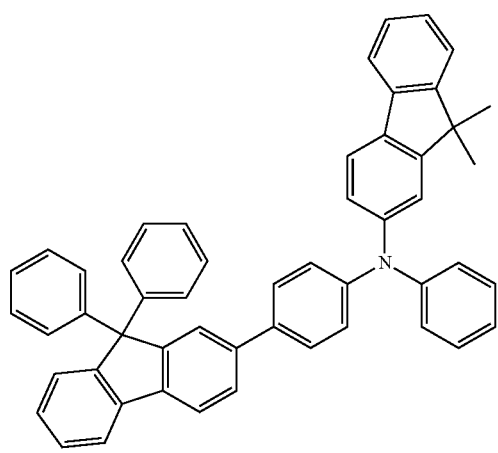
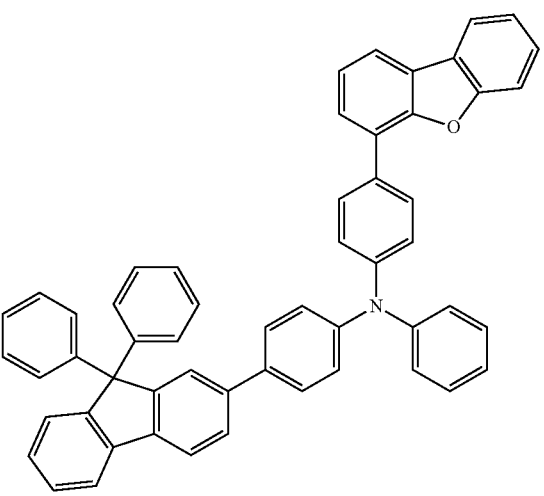
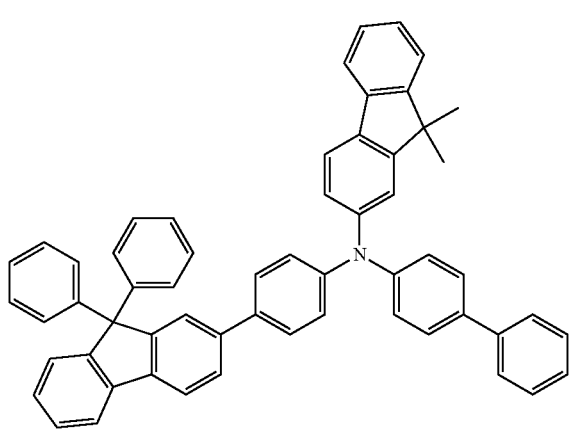
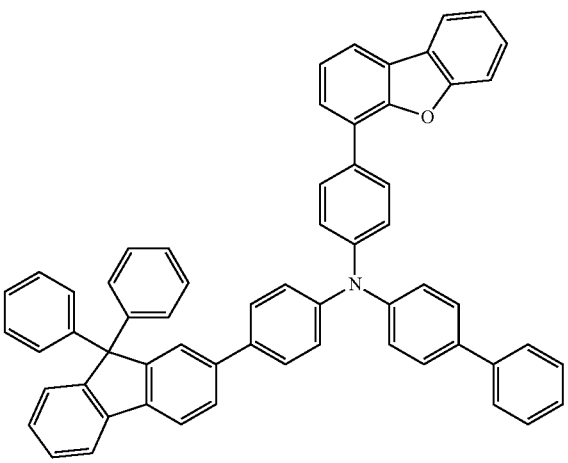
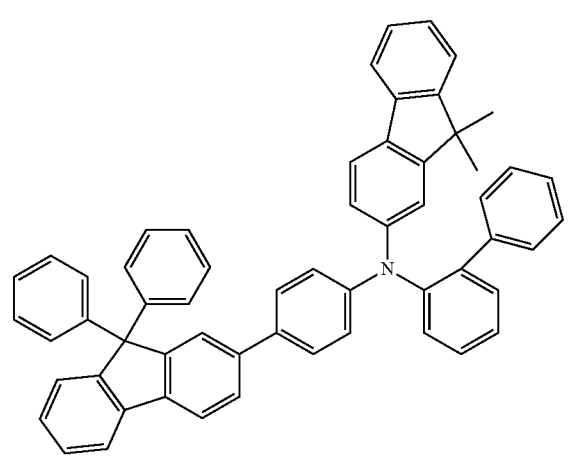
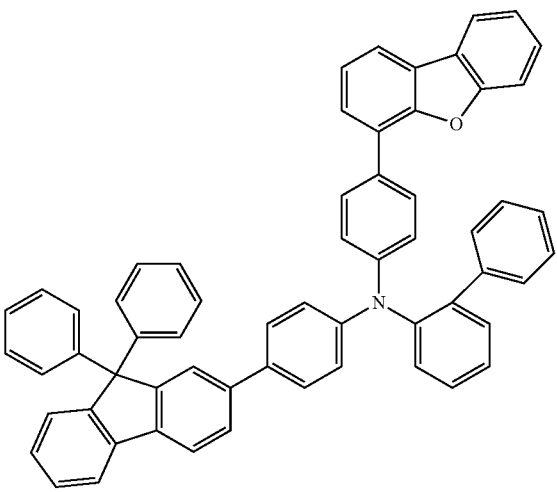

67
-continued
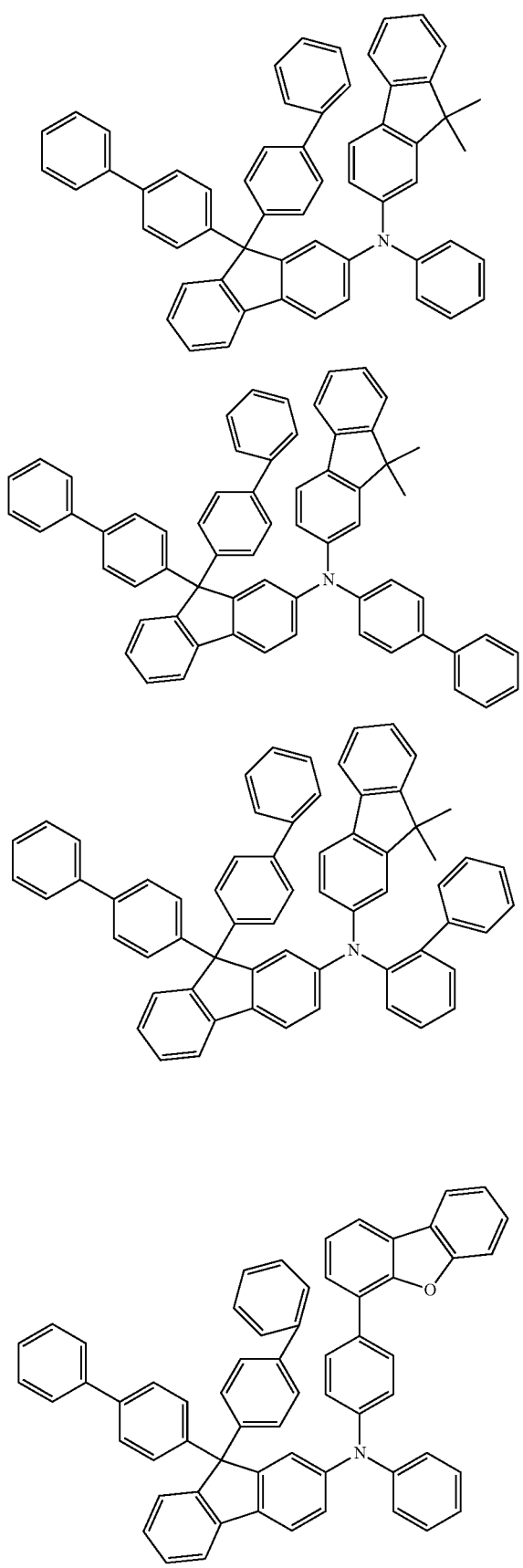
68
-continued
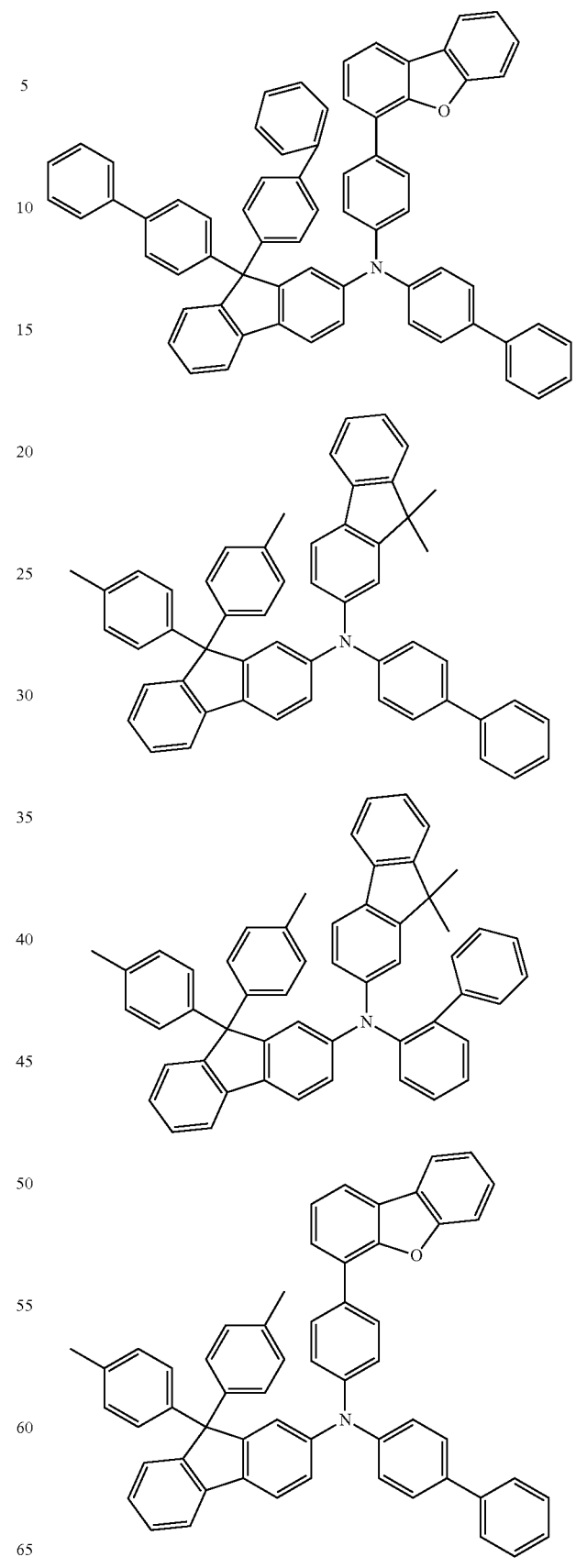

69
-continued
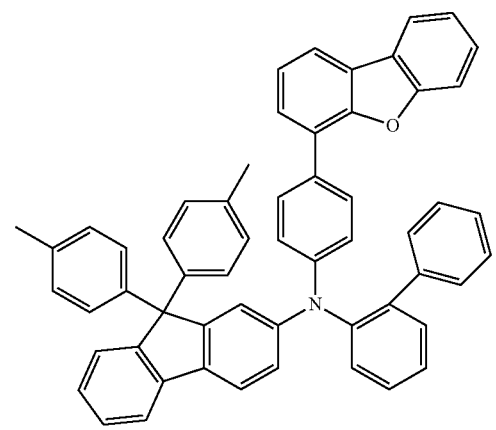
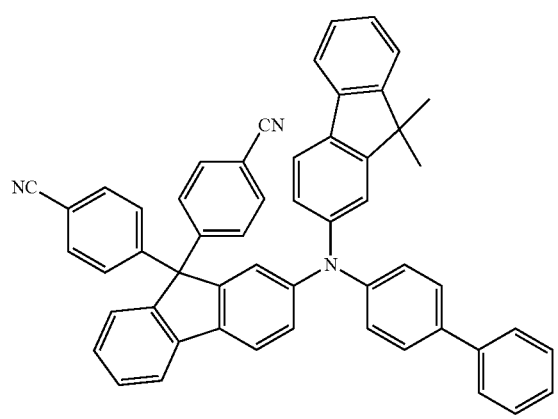
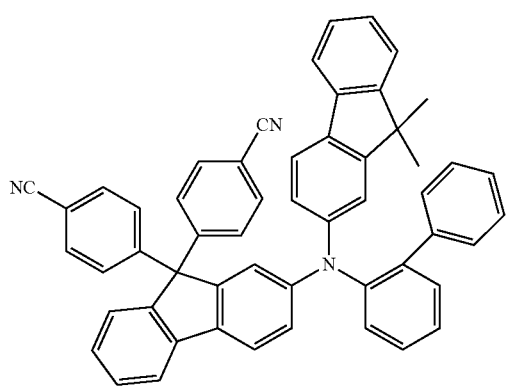
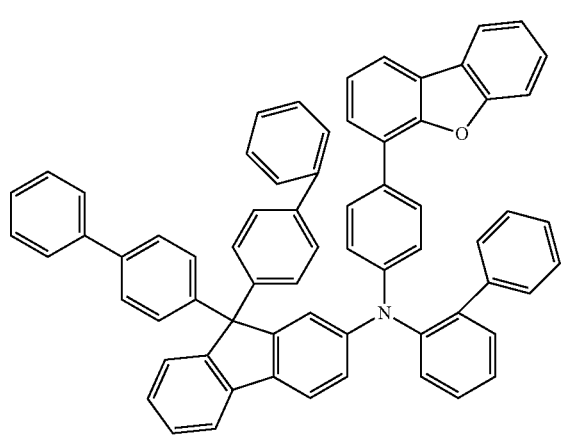
70
-continued
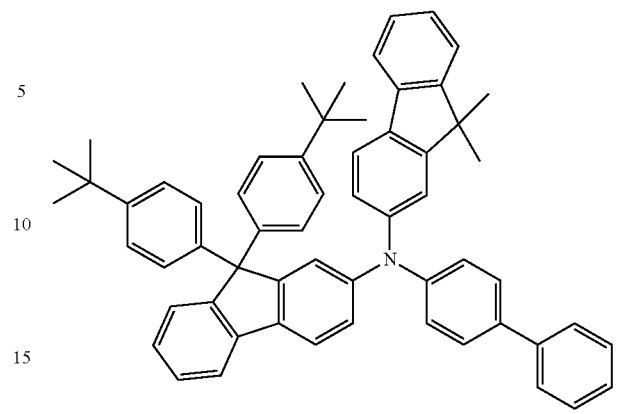
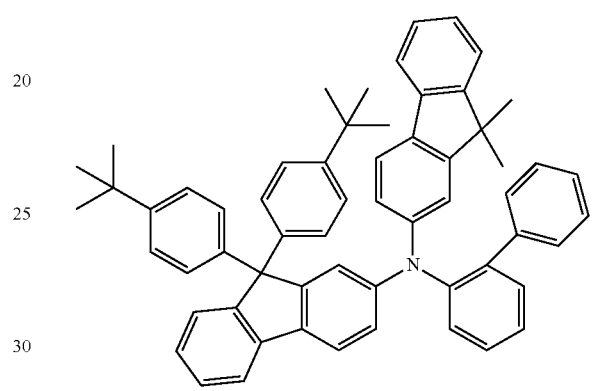
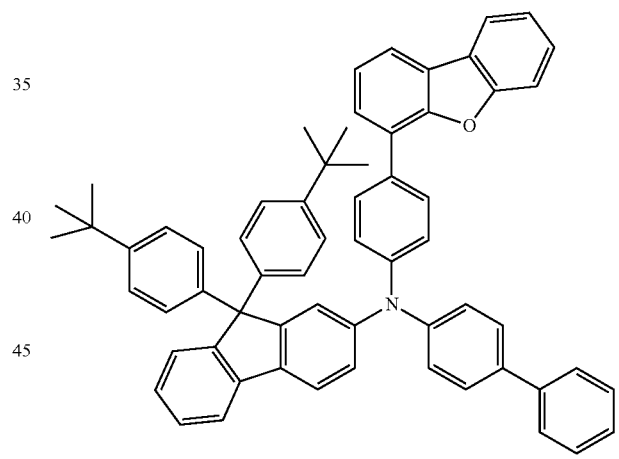
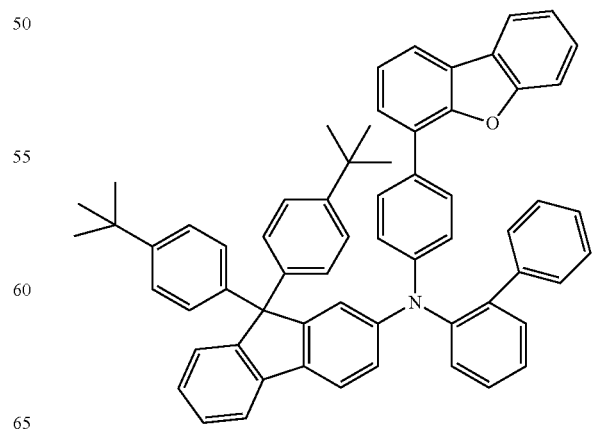

71
-continued
72
-continued
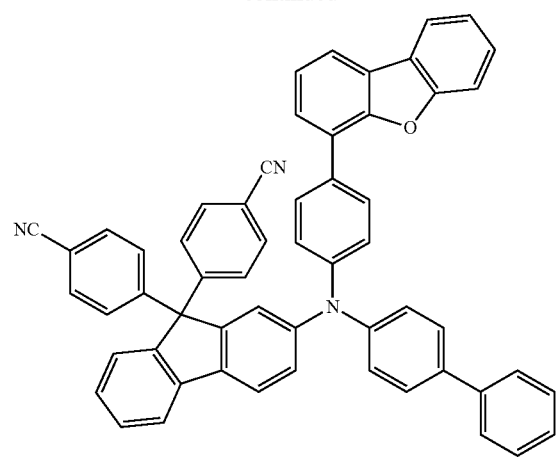
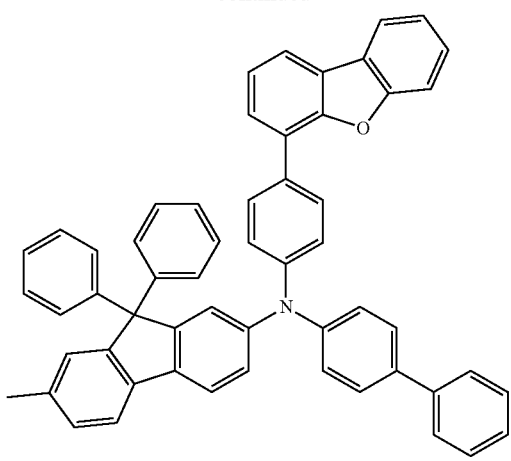

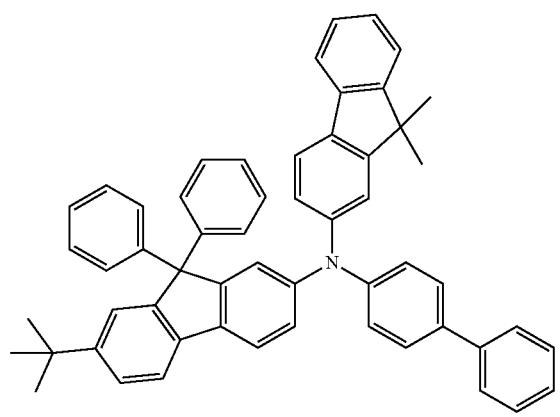
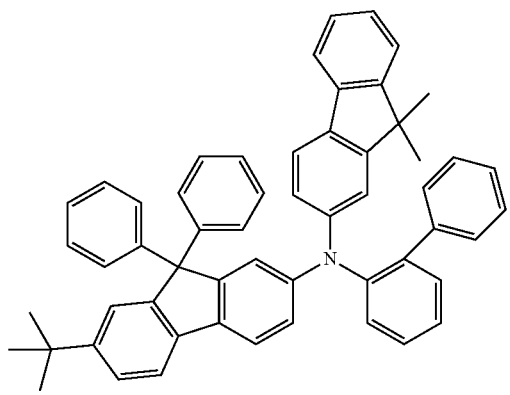
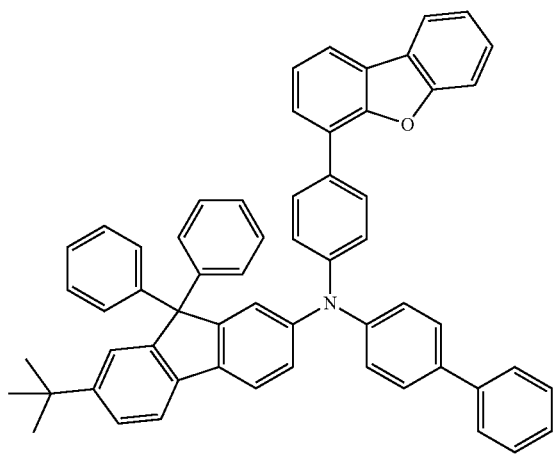
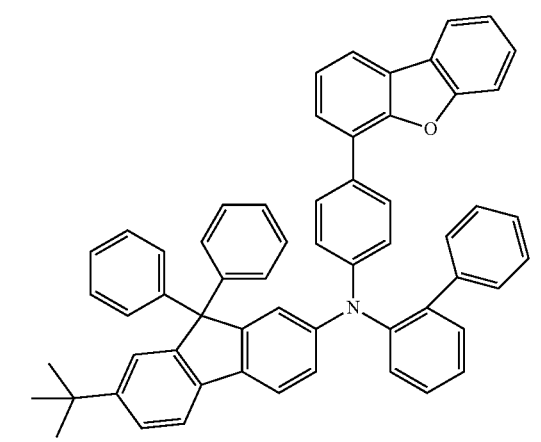
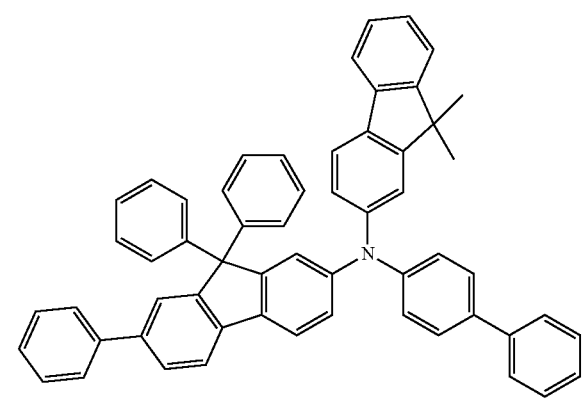
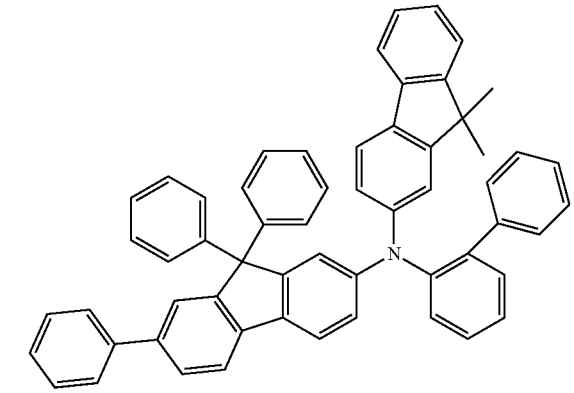
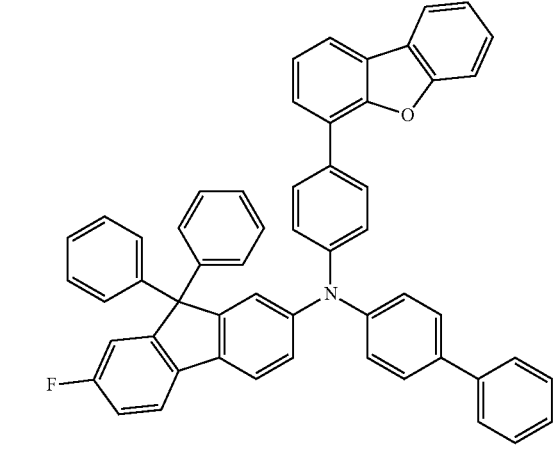
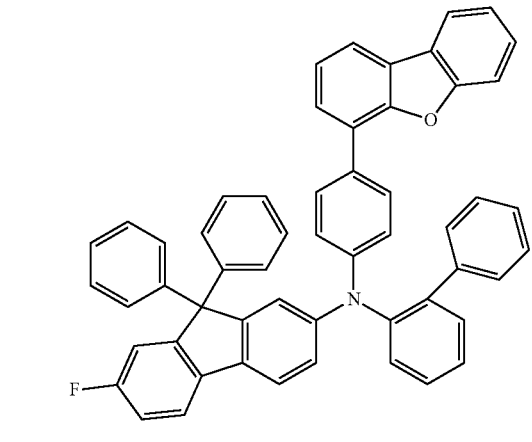

75
-continued
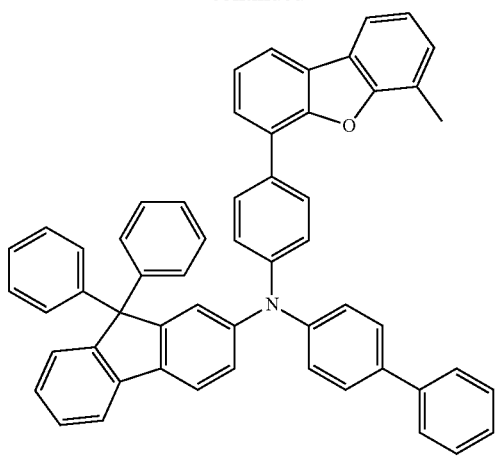
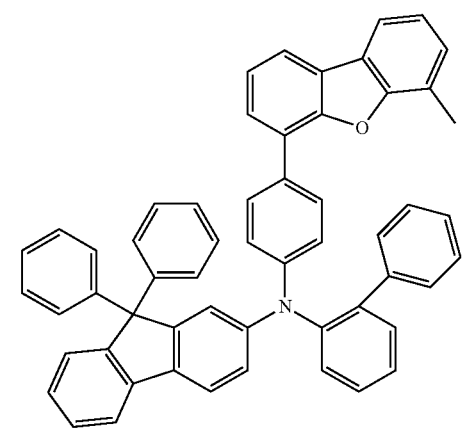
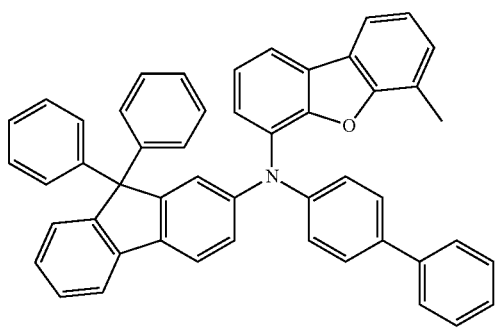
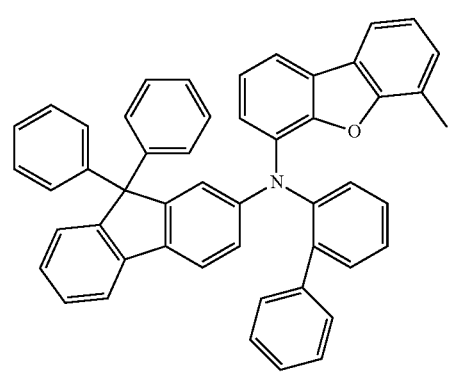
76
-continued
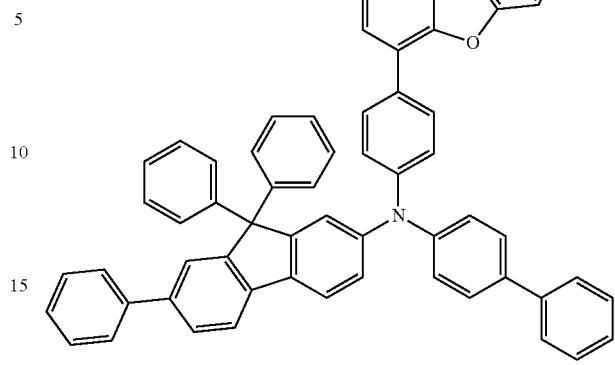
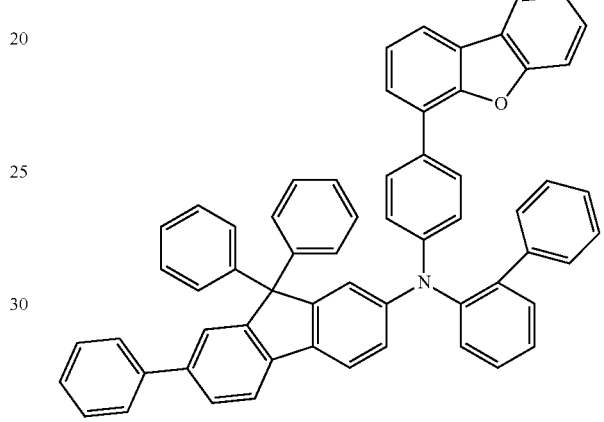
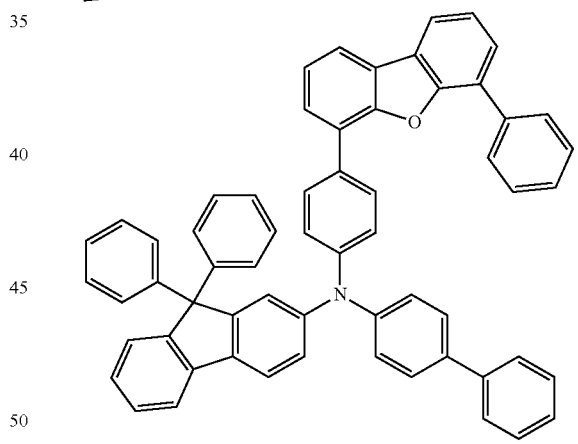
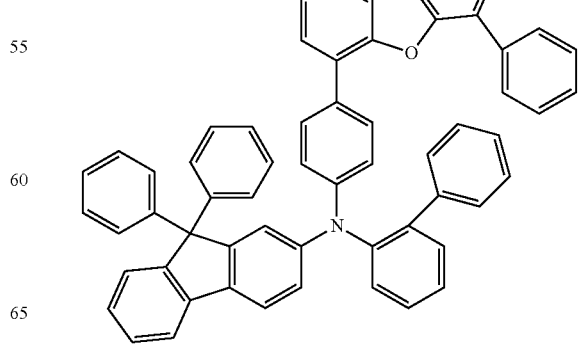

77
-continued
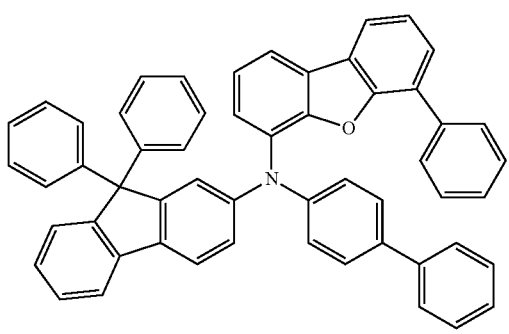
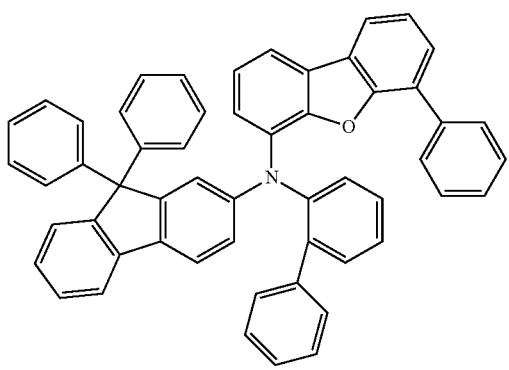
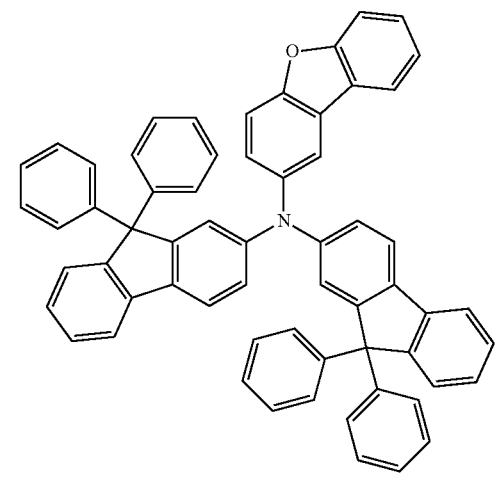
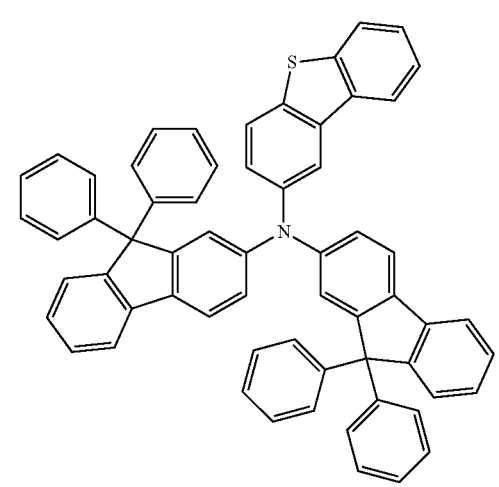
78
-continued
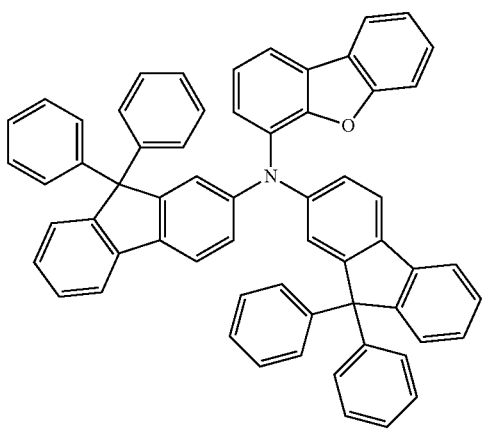
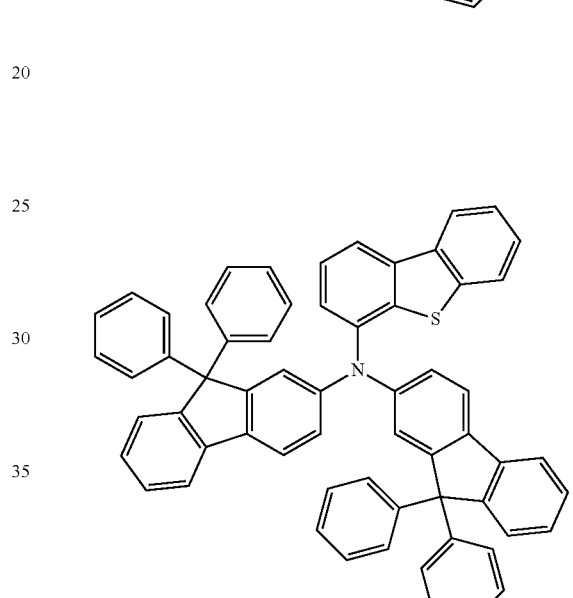
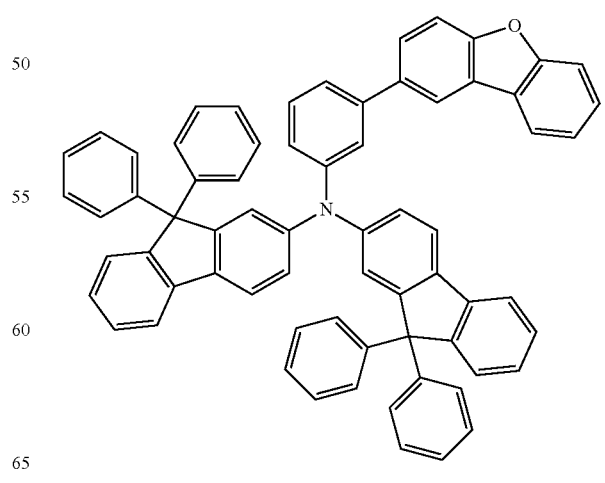

-continued
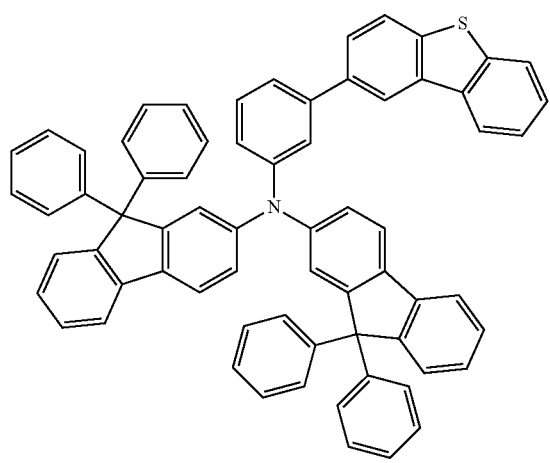
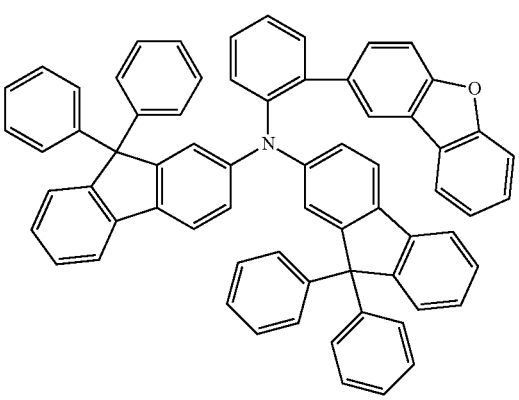
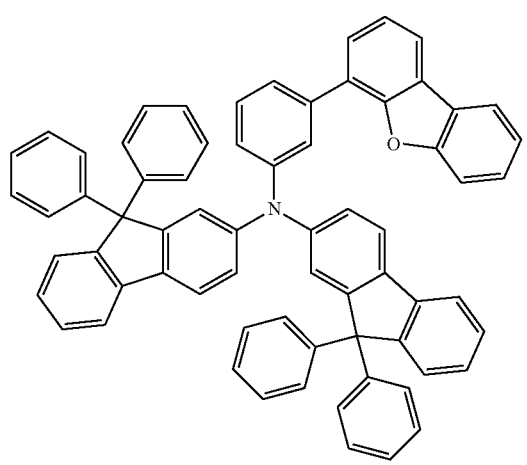
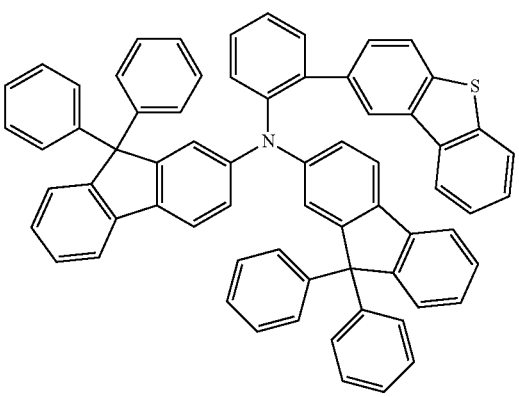
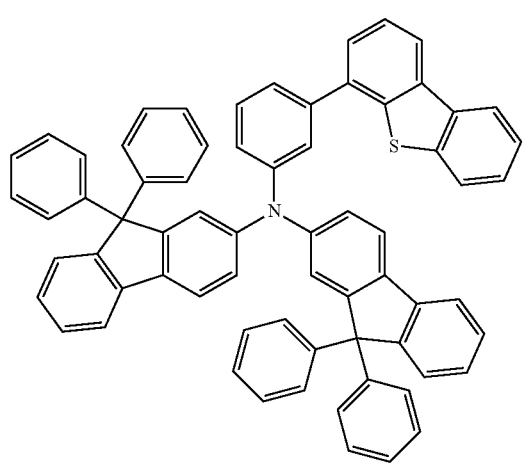
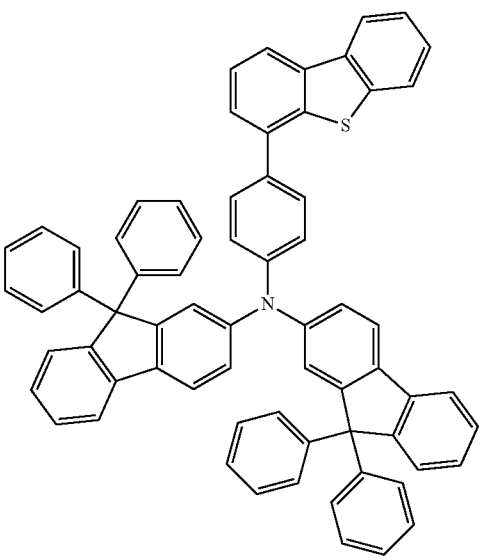

81
-continued
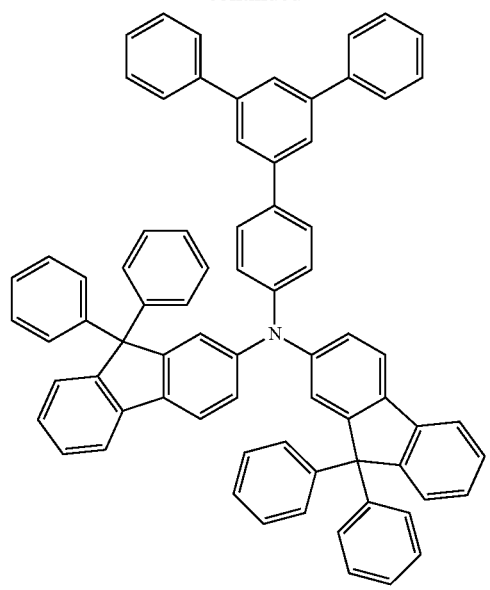
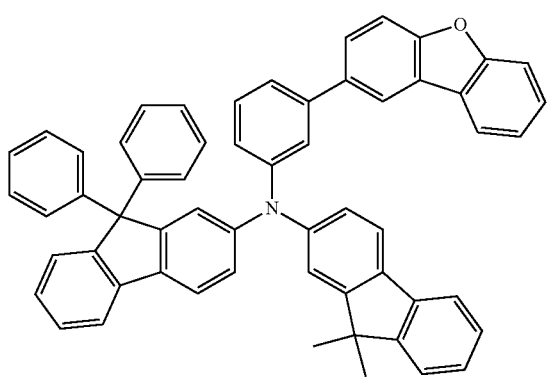
82
-continued
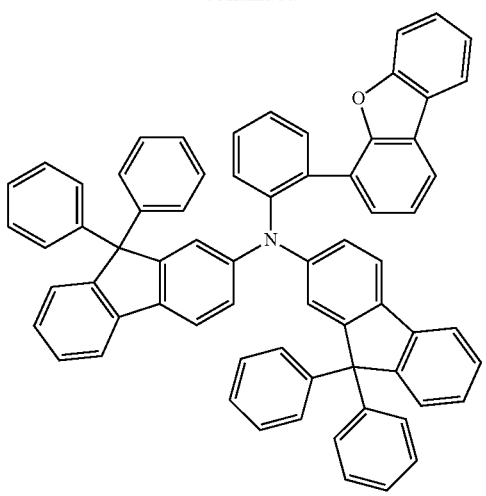
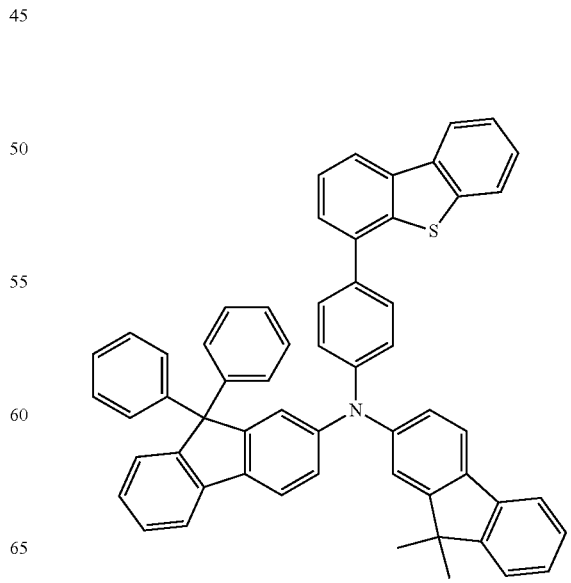

83
-continued
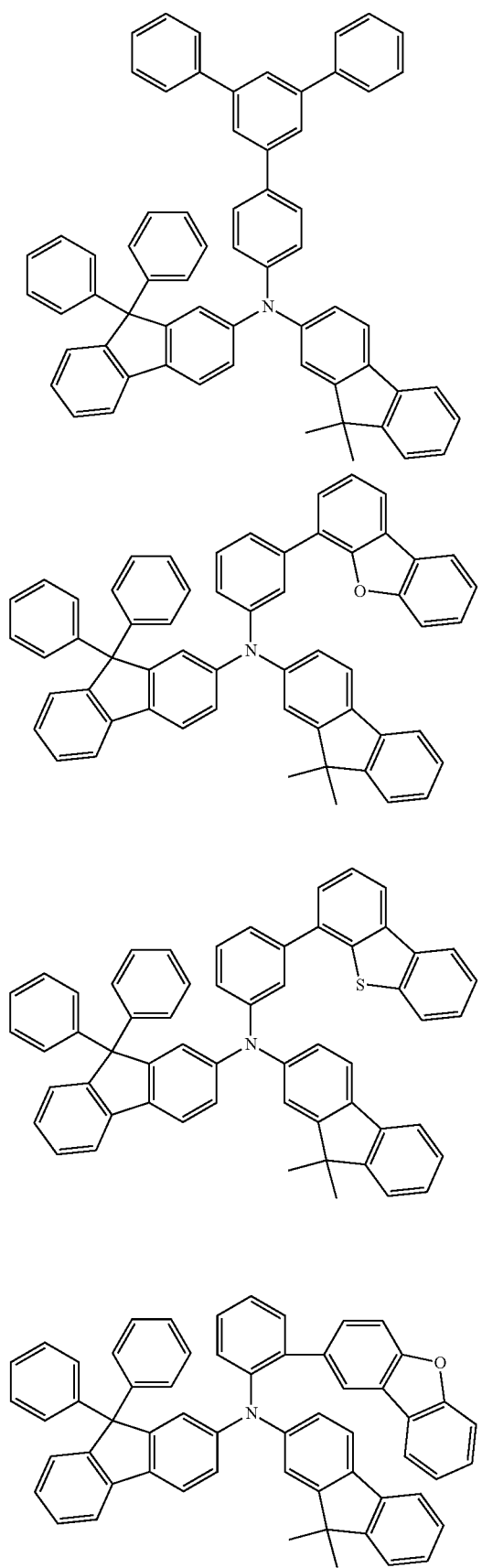
84
-continued
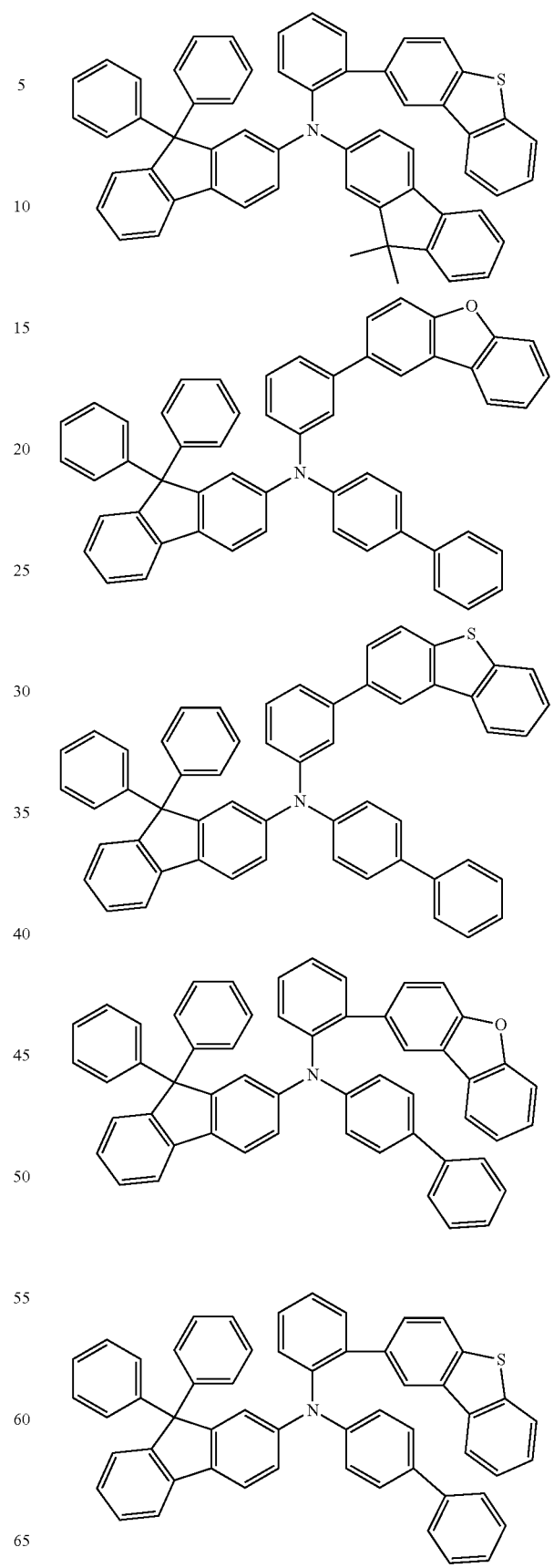

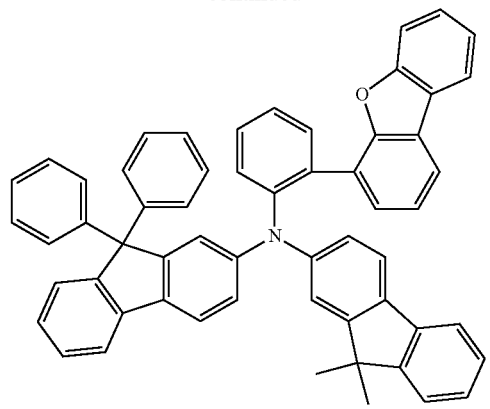
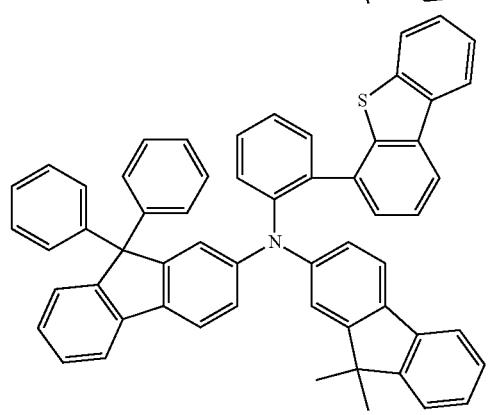
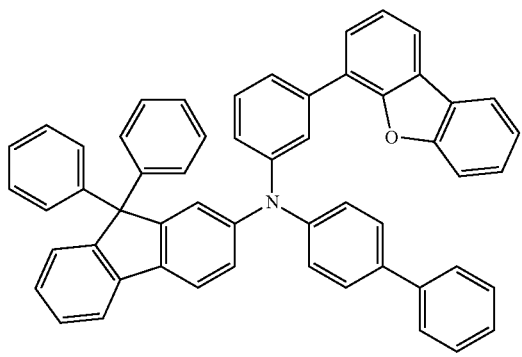
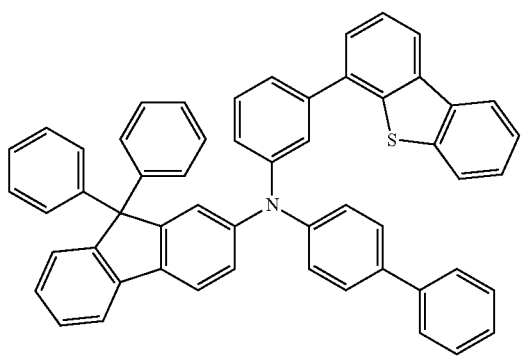
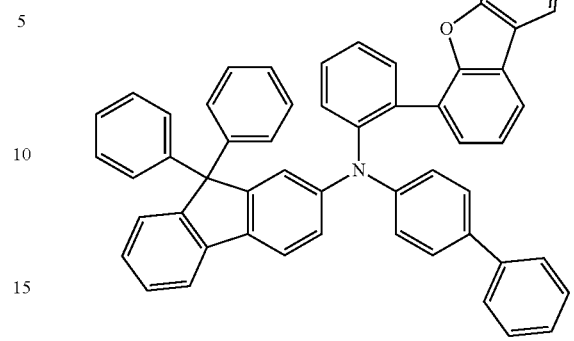
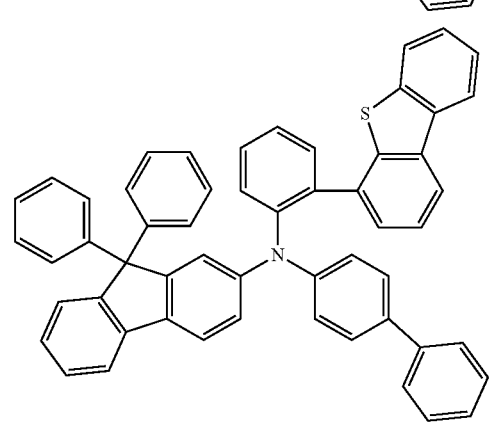
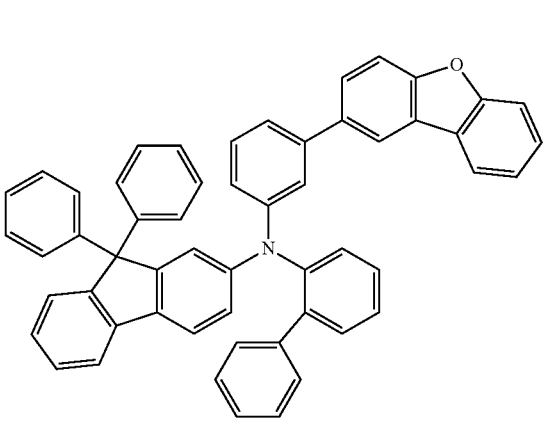
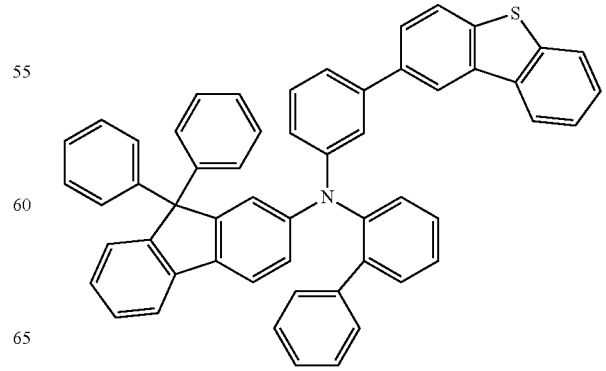

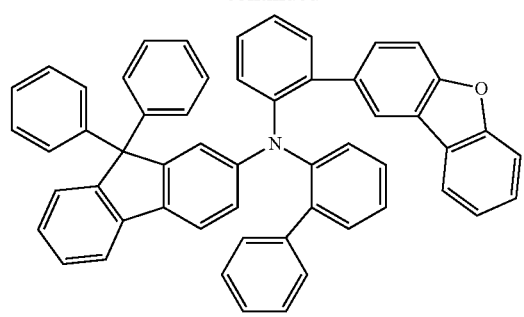
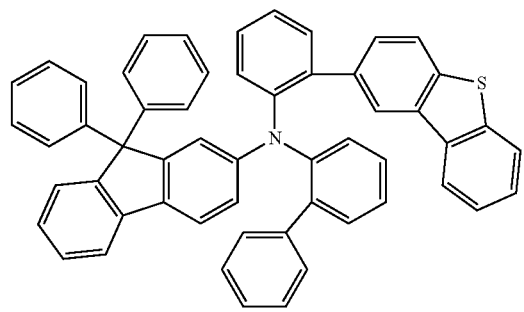
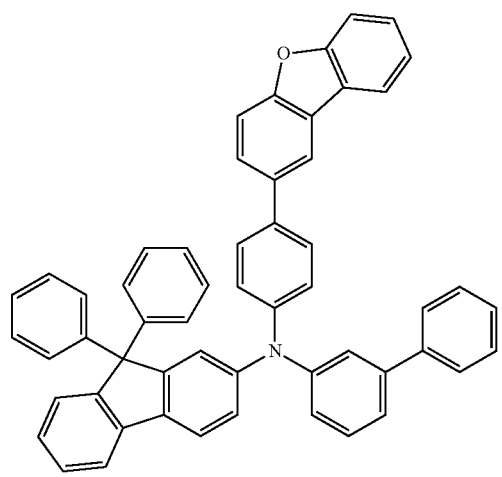
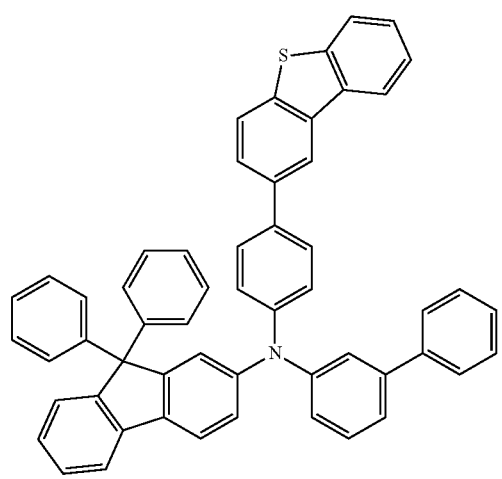
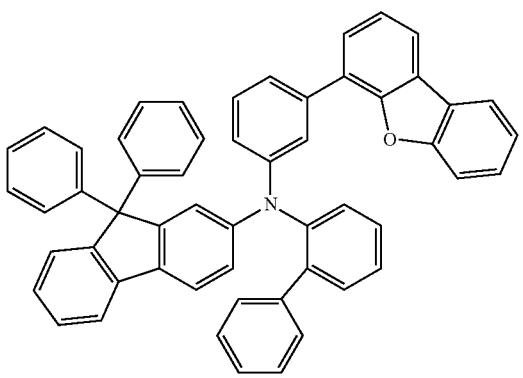
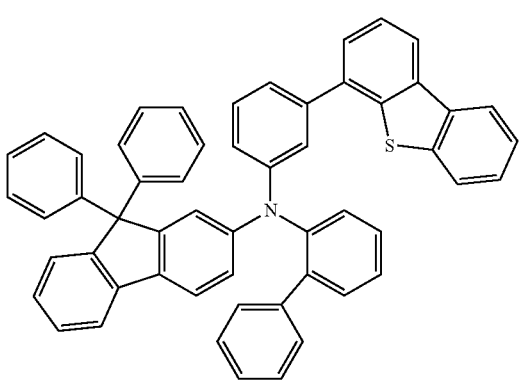
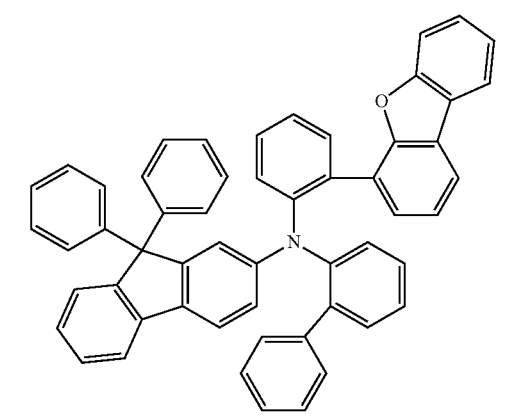
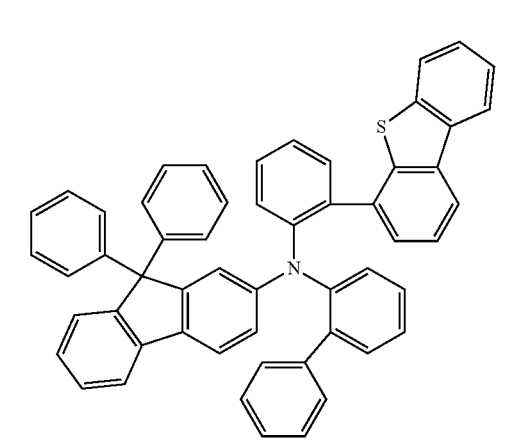

89
-continued
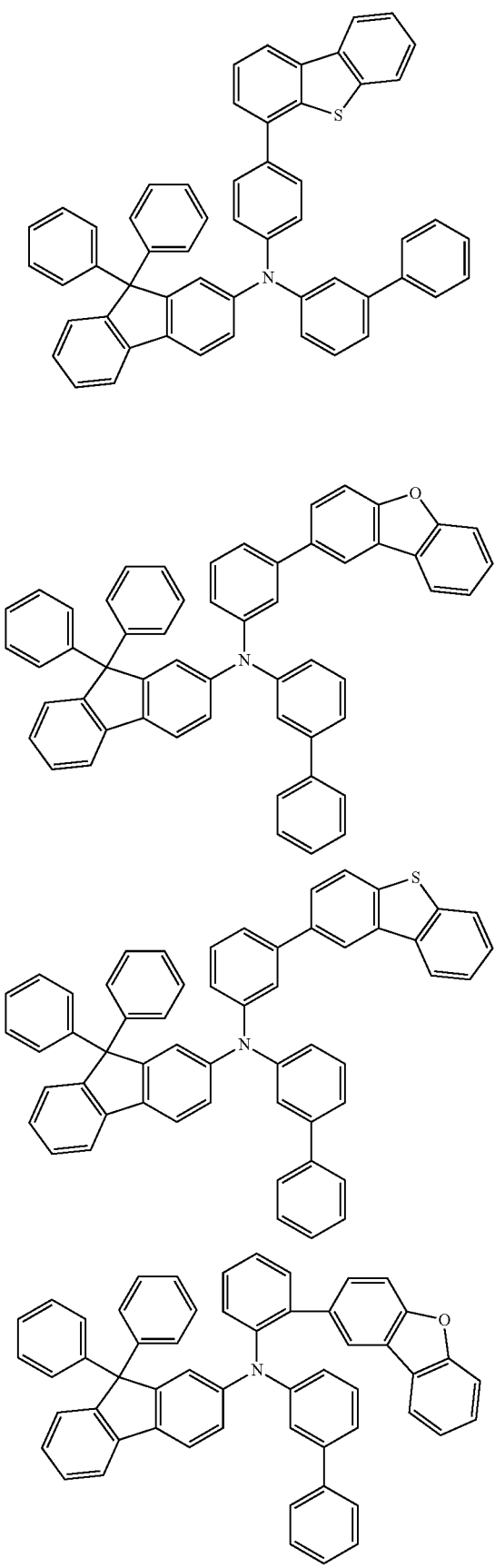
90
-continued
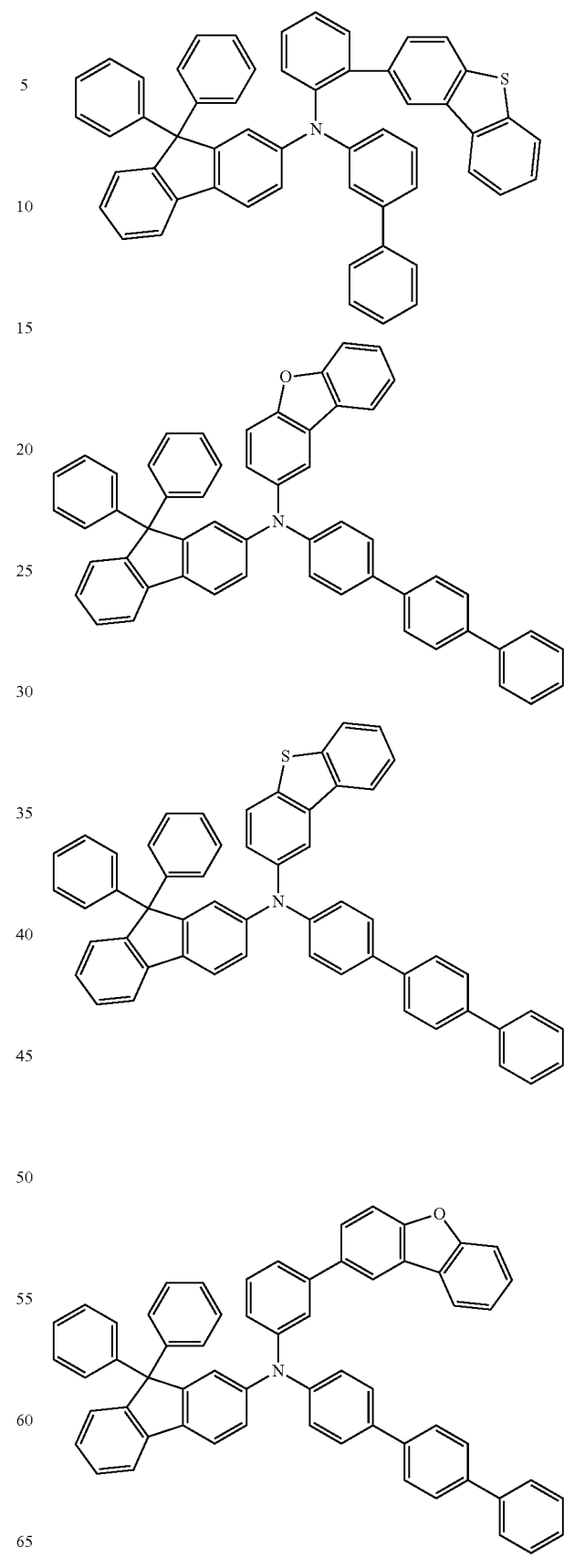

-continued
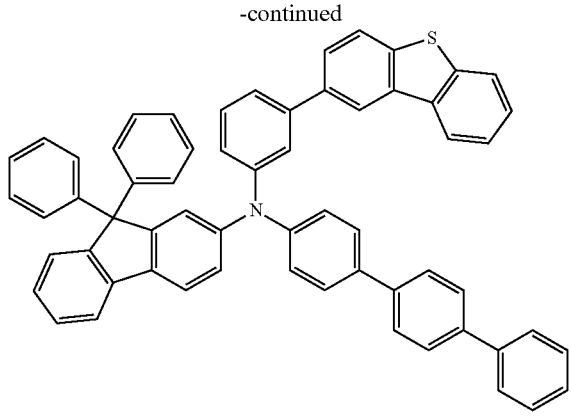
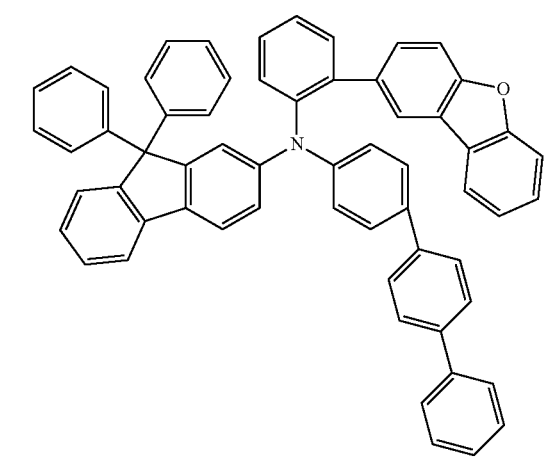
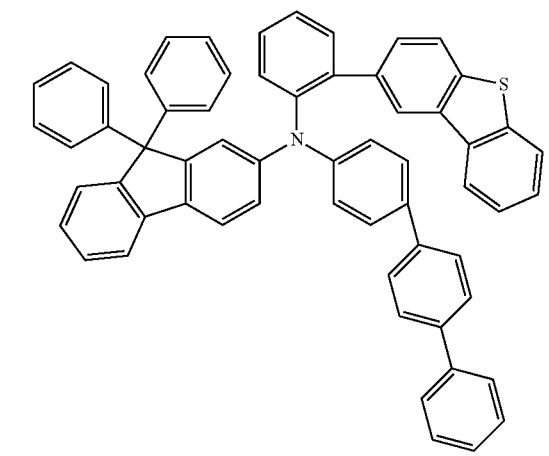
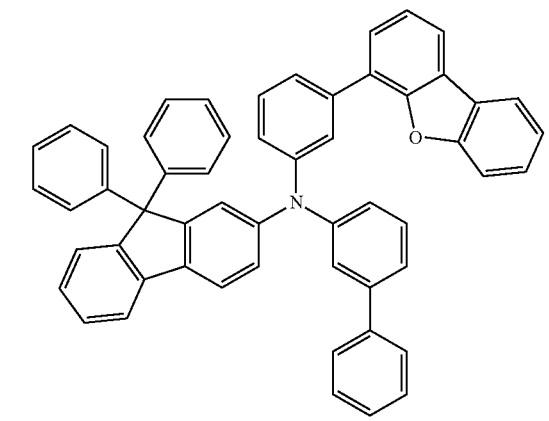
-continued
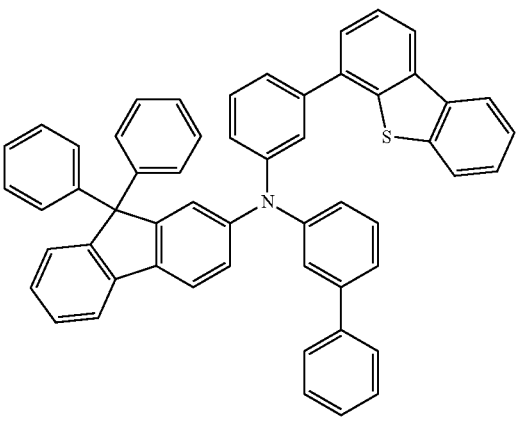
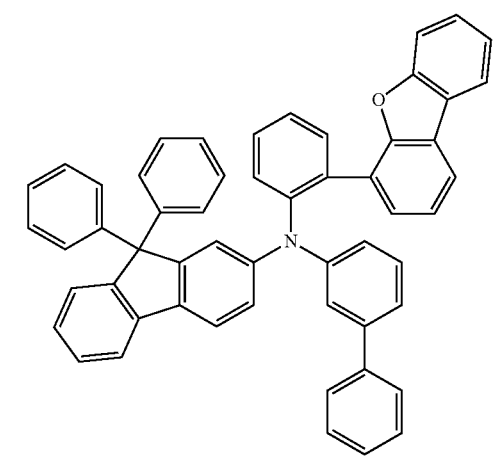
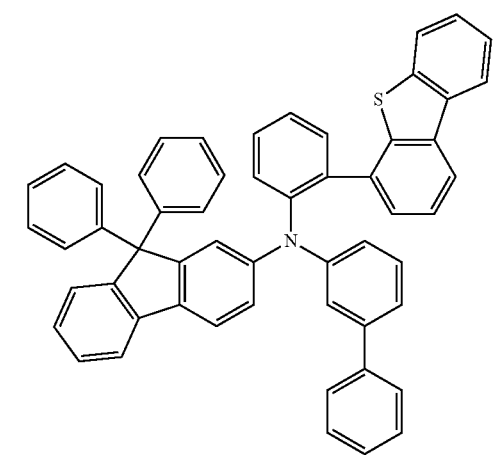
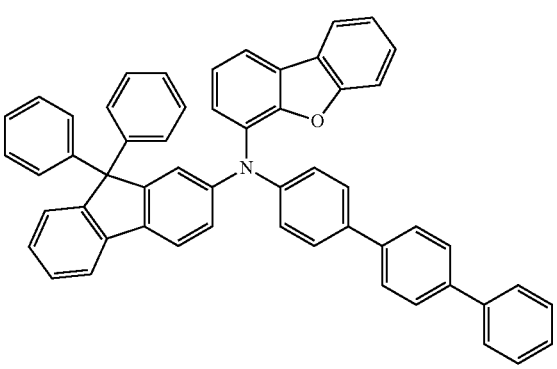

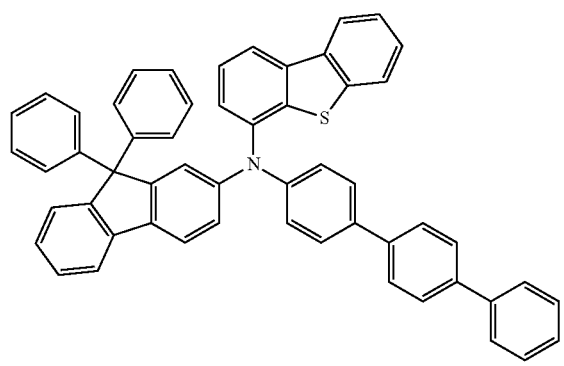
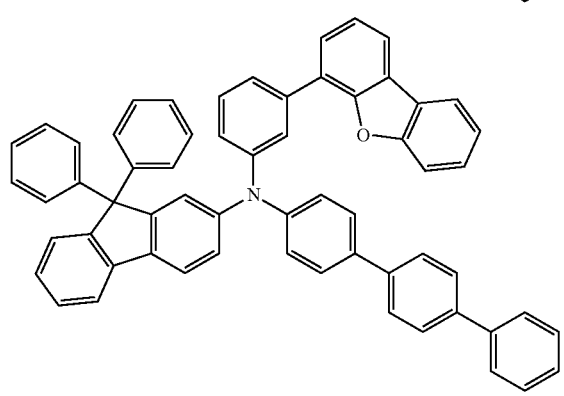
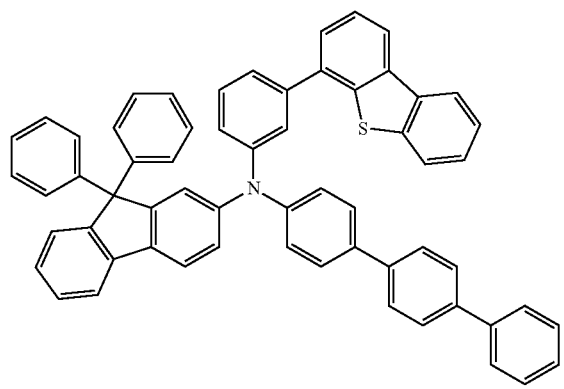
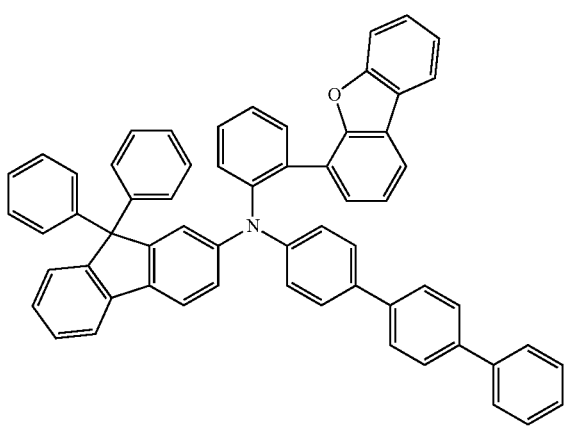
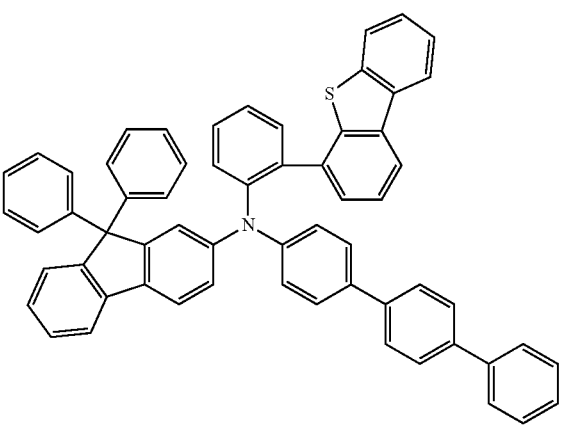
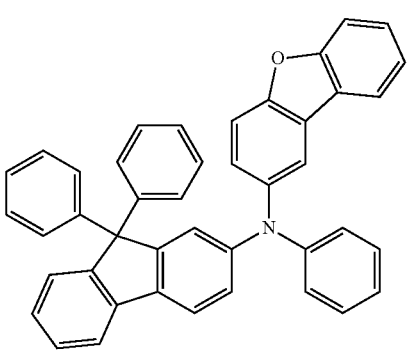
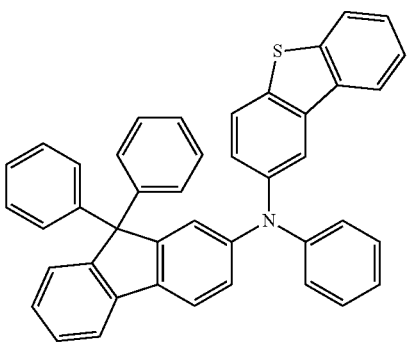
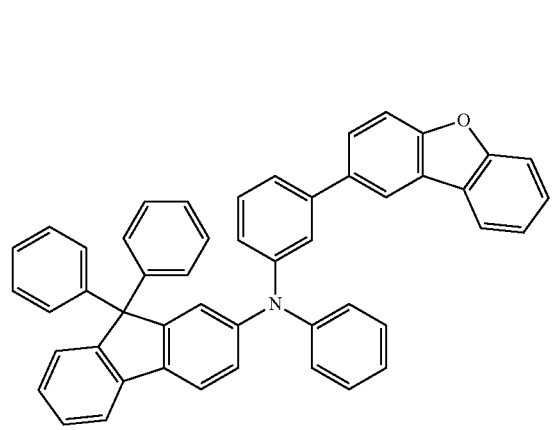

95
-continued
96
-continued
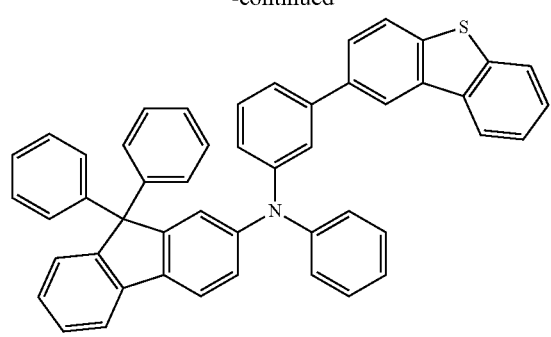
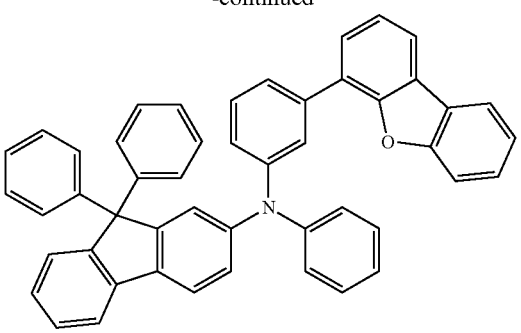
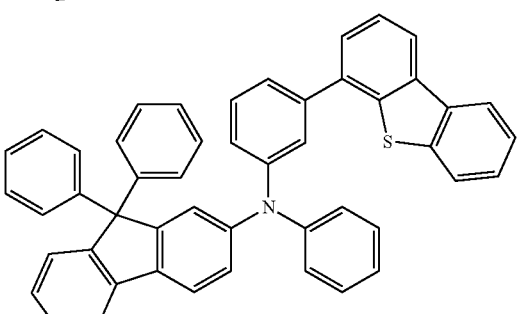
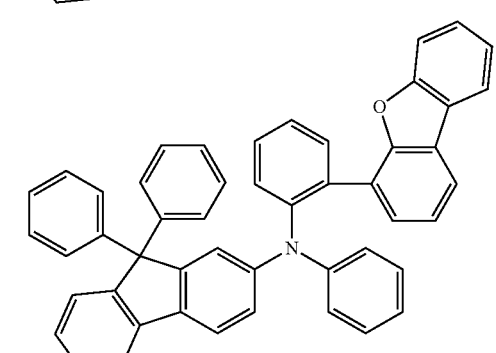
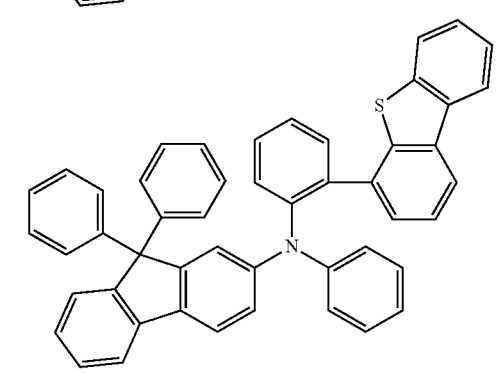
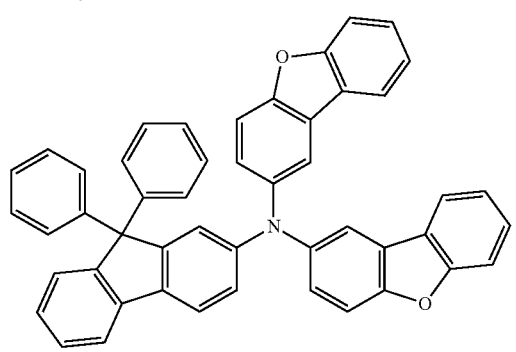

97
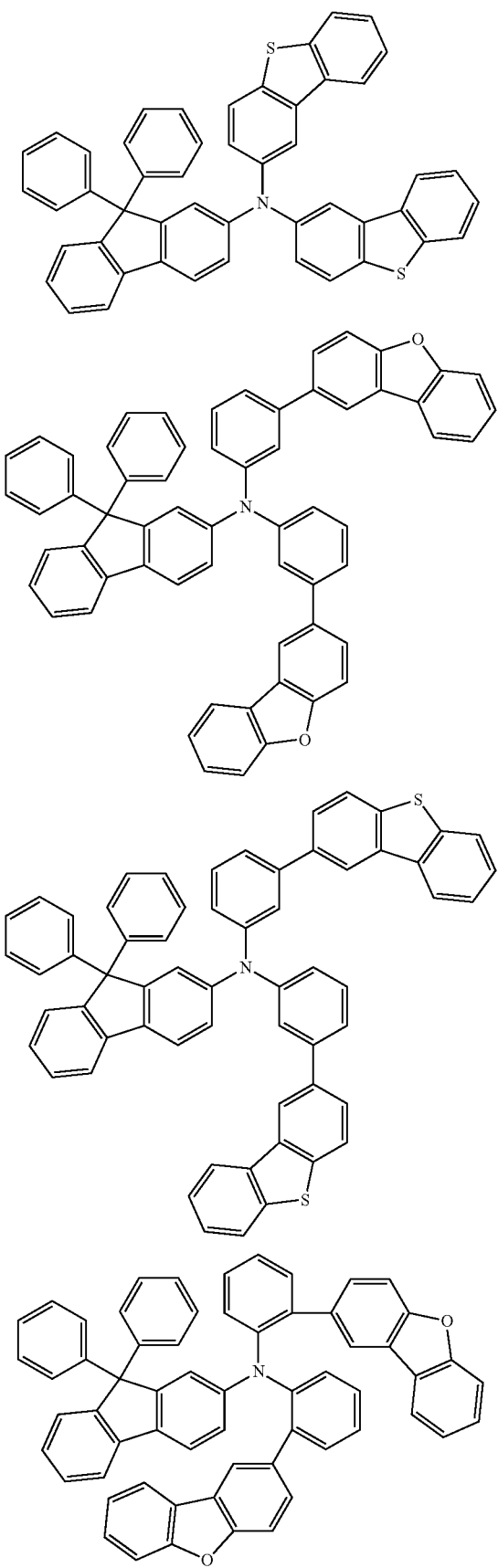
98
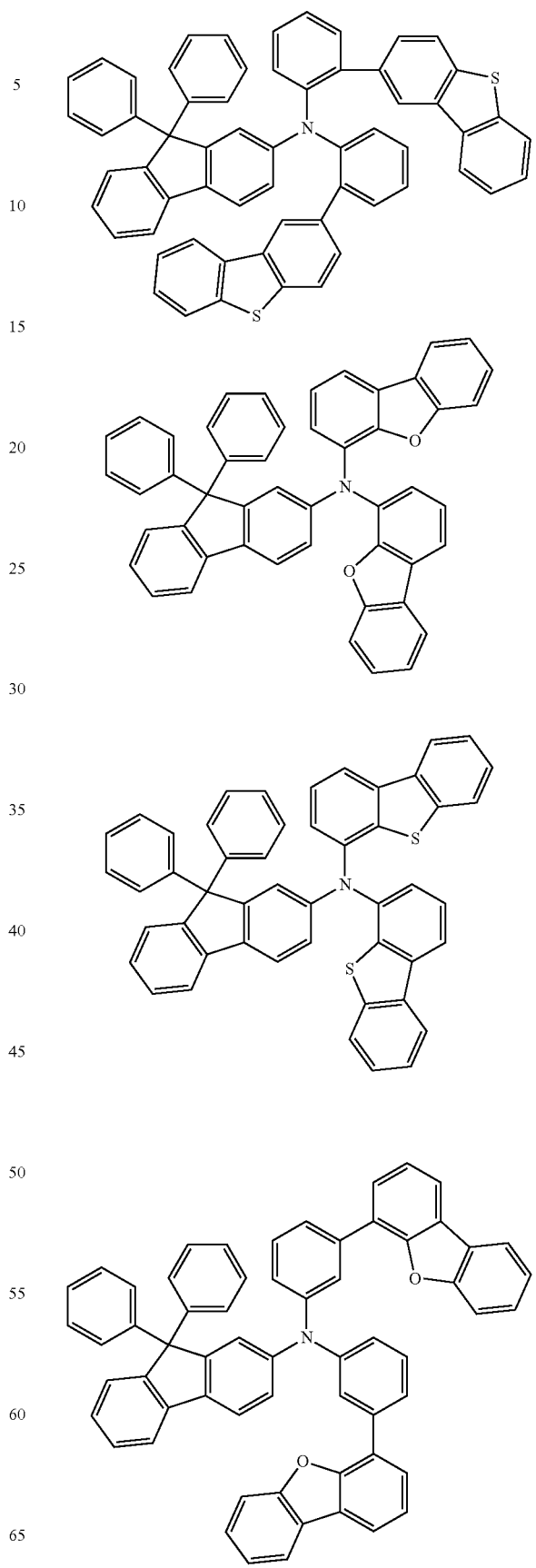

99
-continued
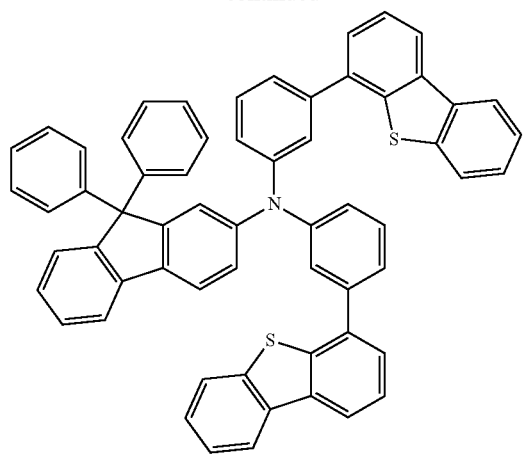
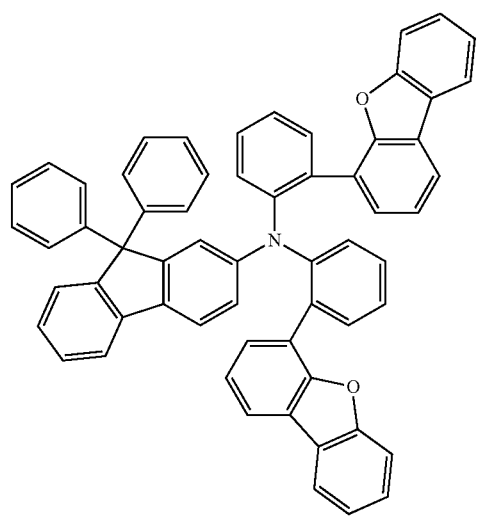
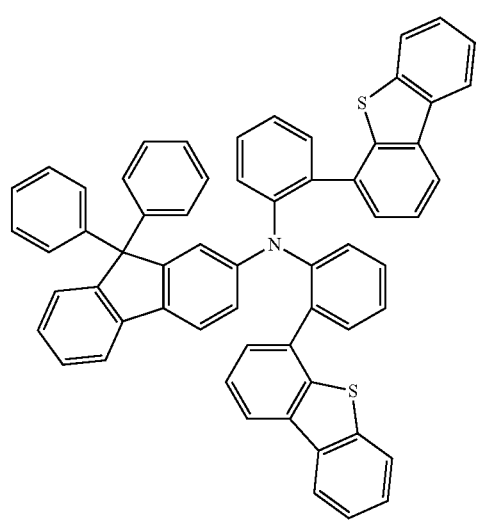
100
-continued
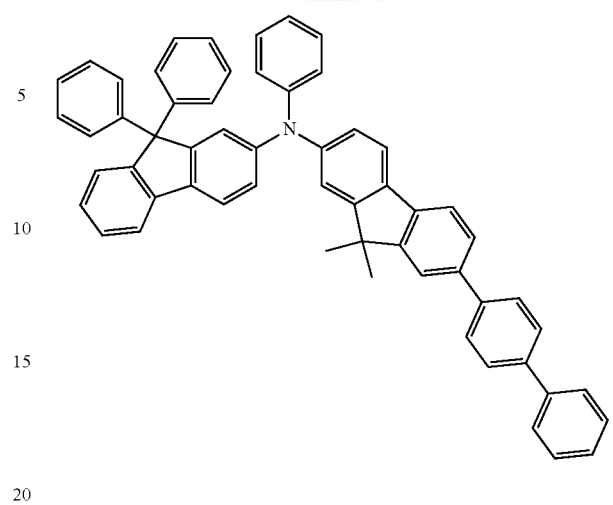
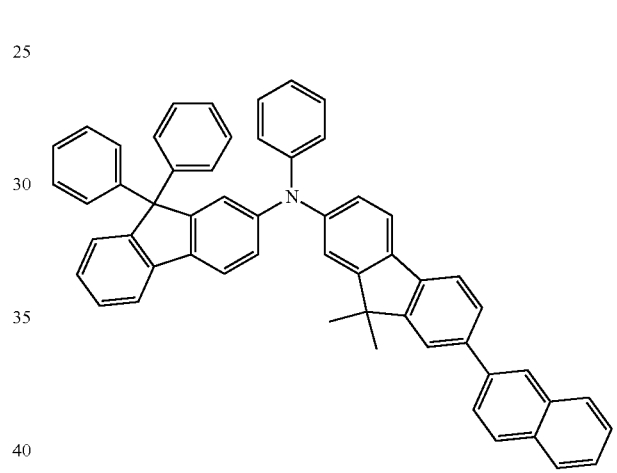
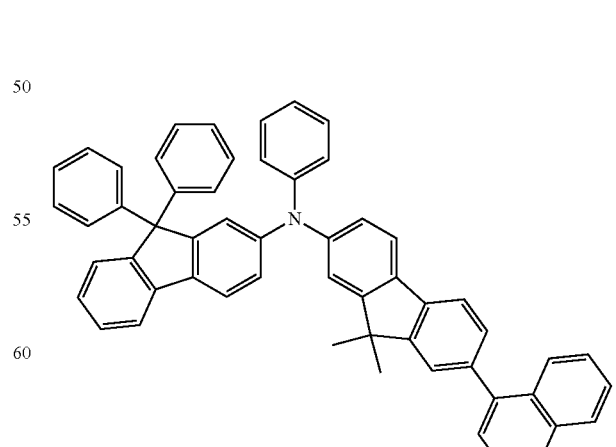

101
-continued
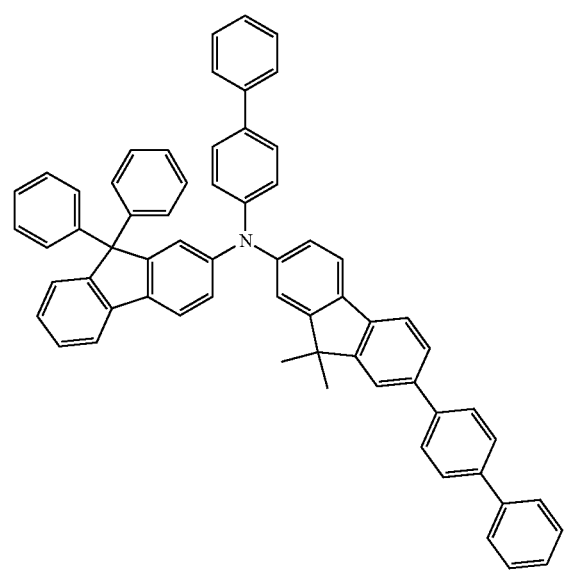
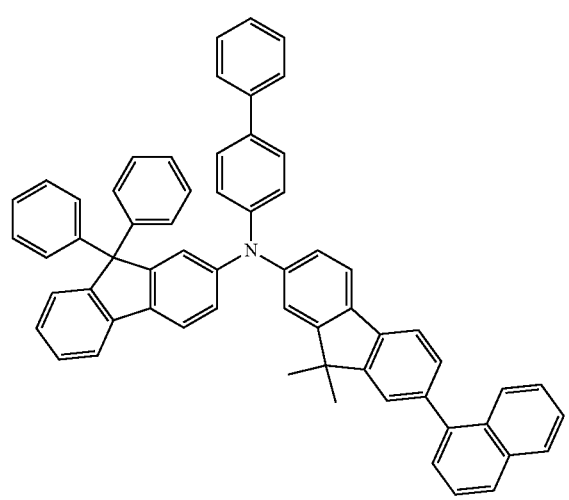
102
-continued
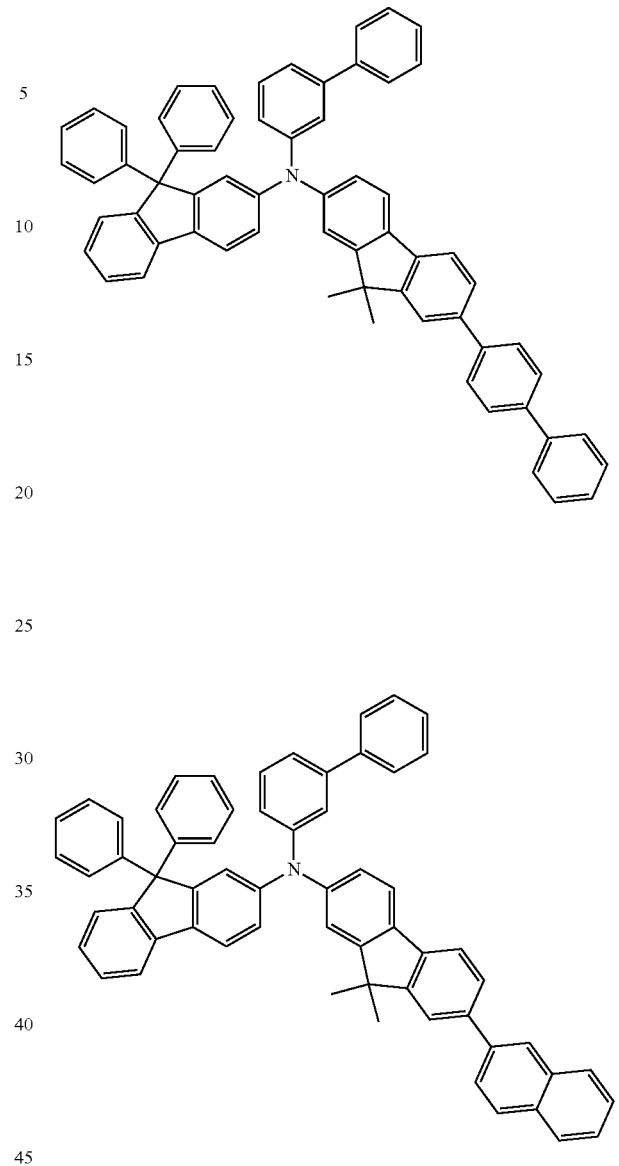

103
-continued
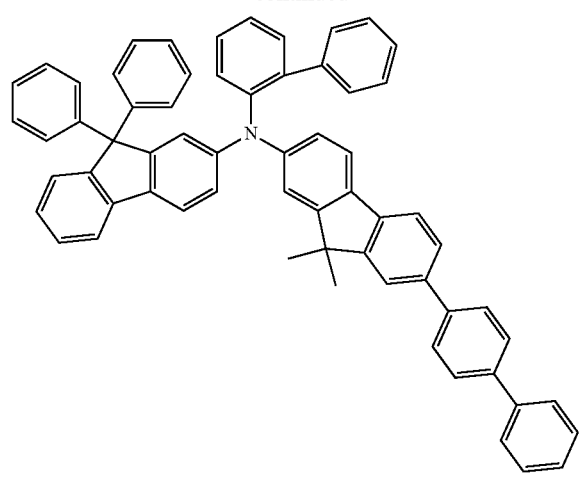
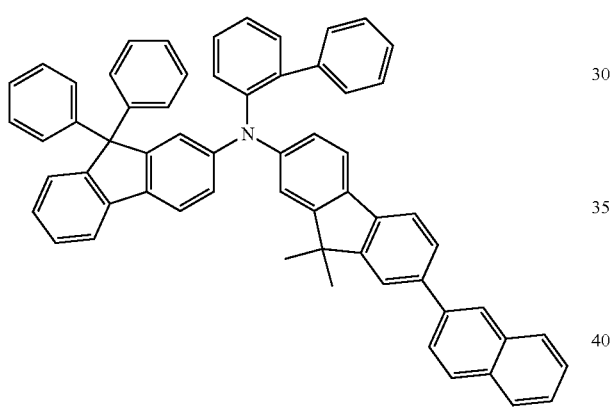
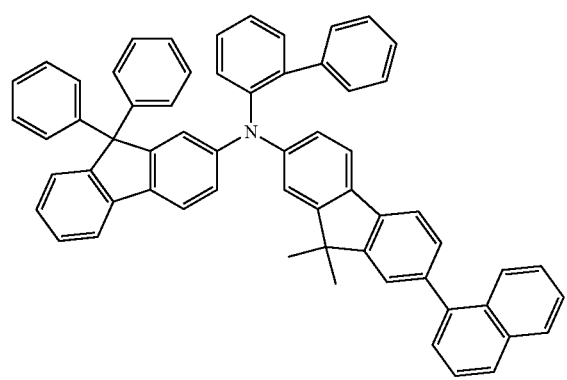
104
-continued
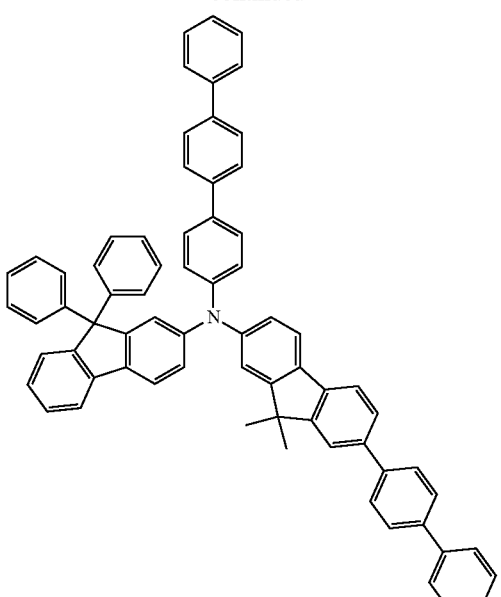
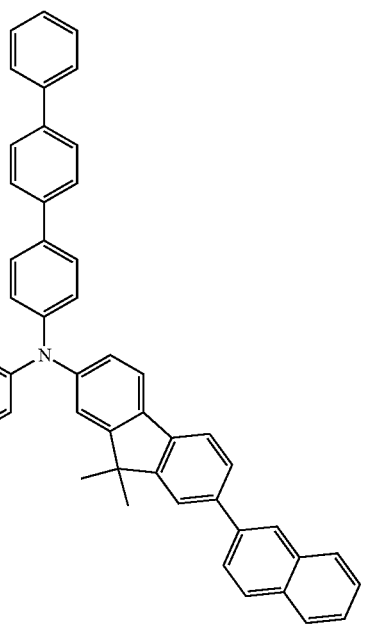

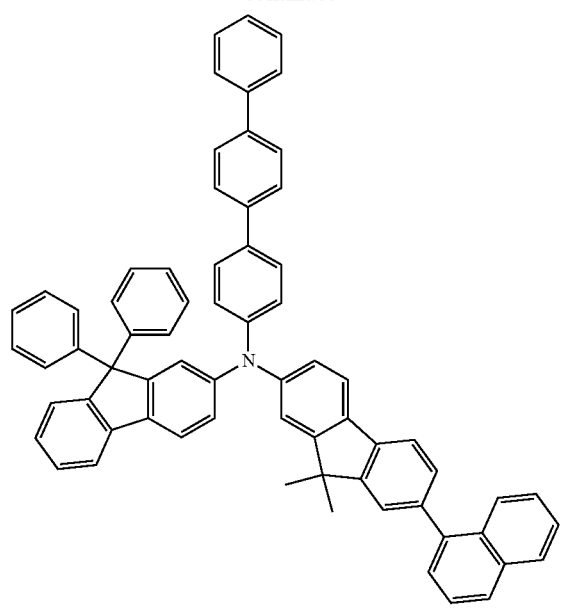
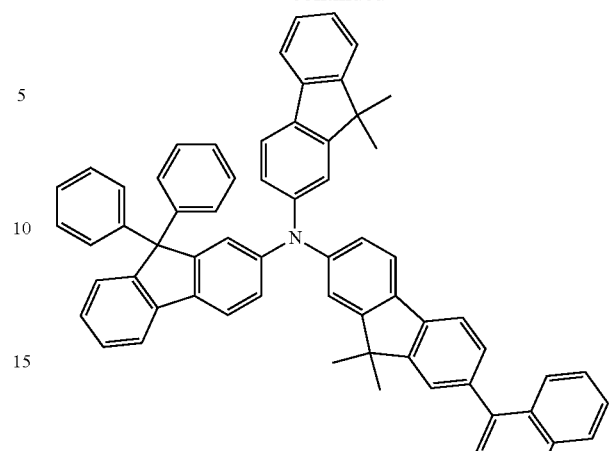
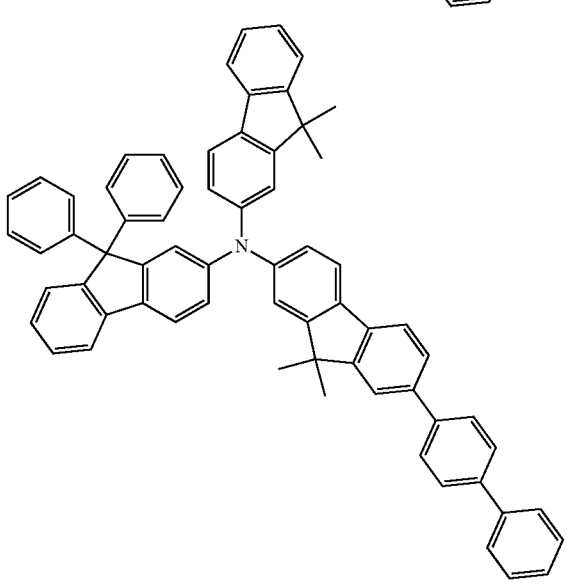
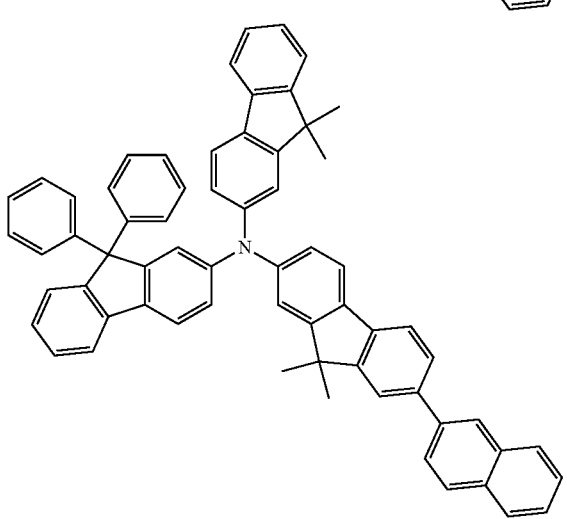
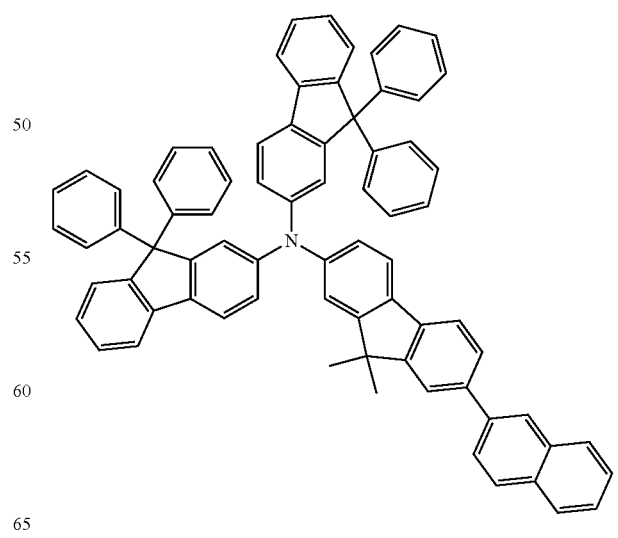

107
-continued
108
-continued
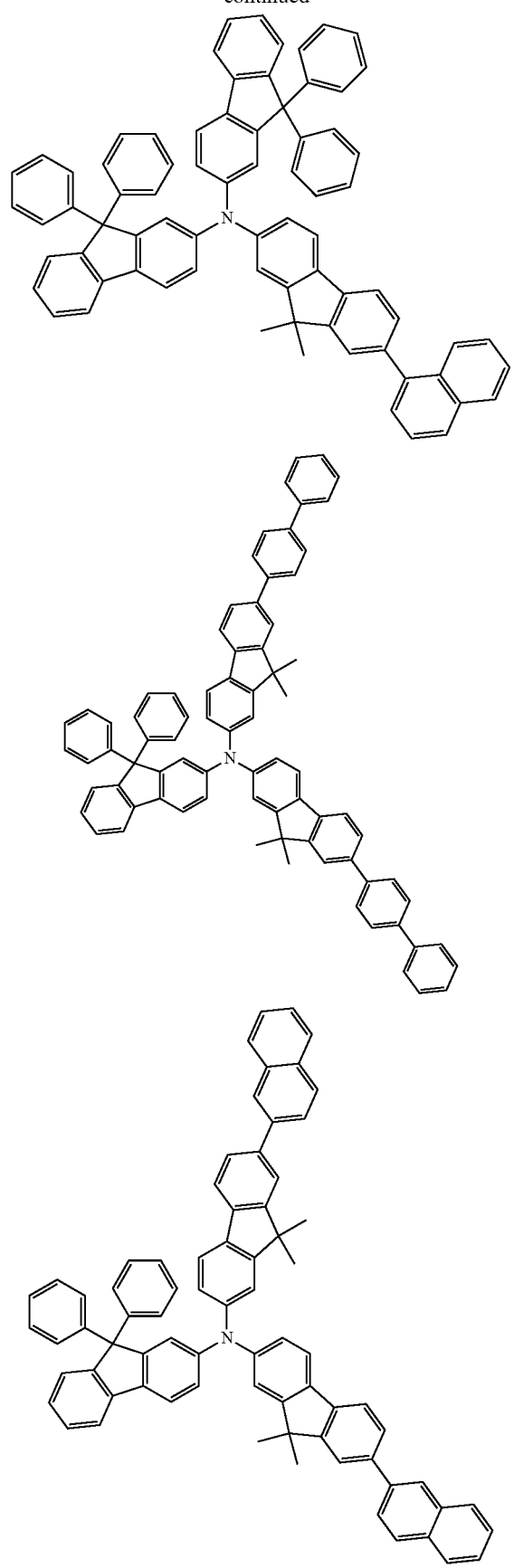
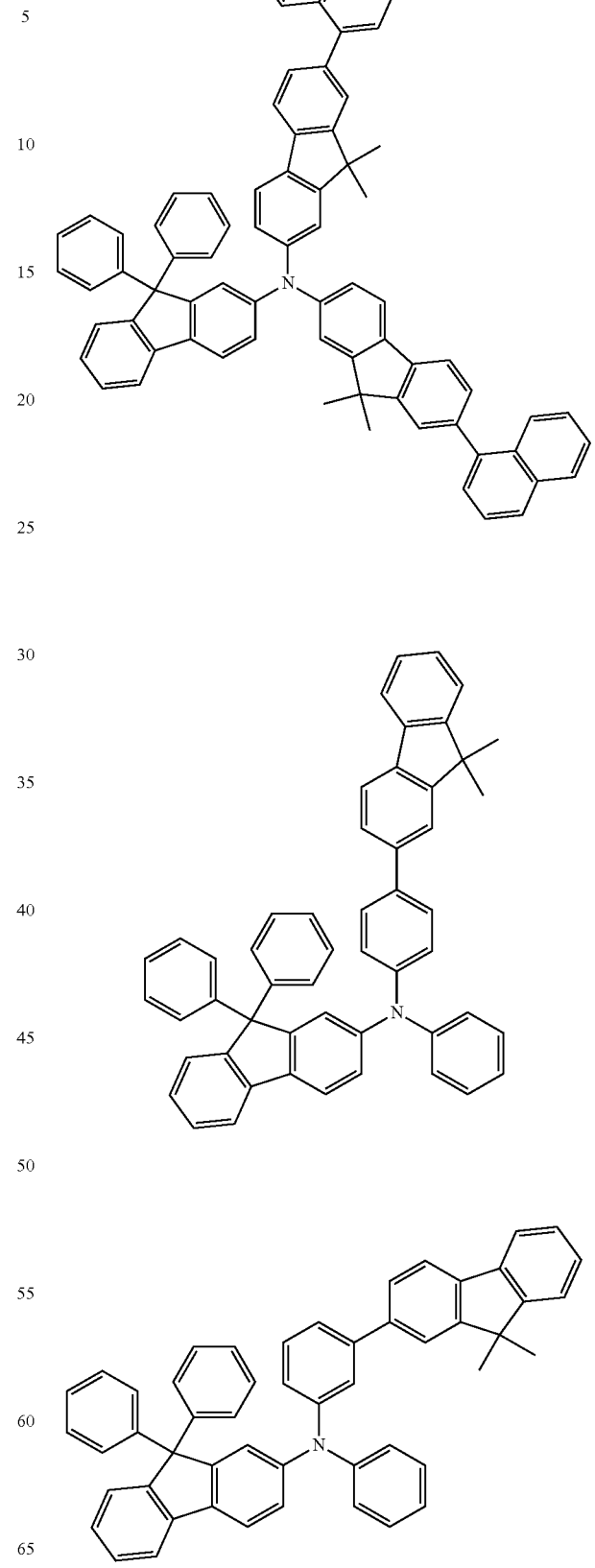

109
-continued
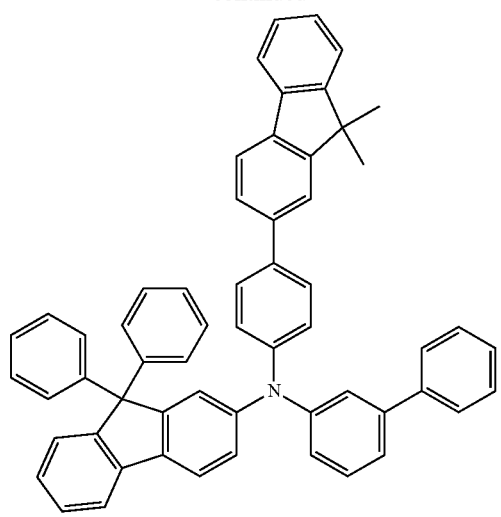
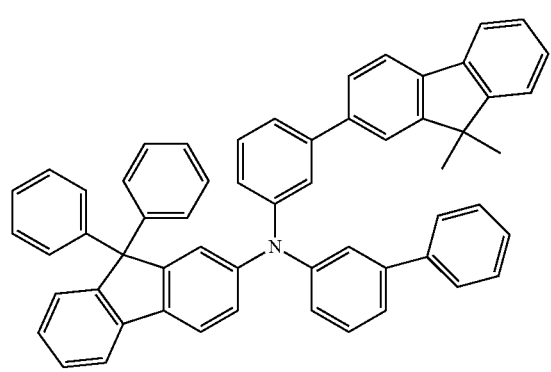
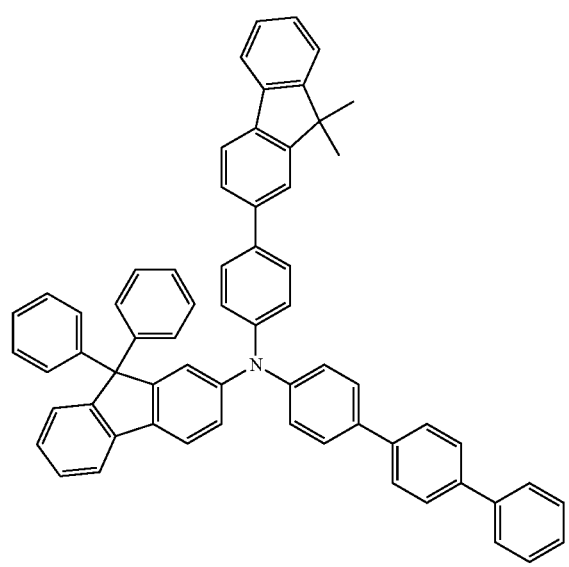
110
-continued
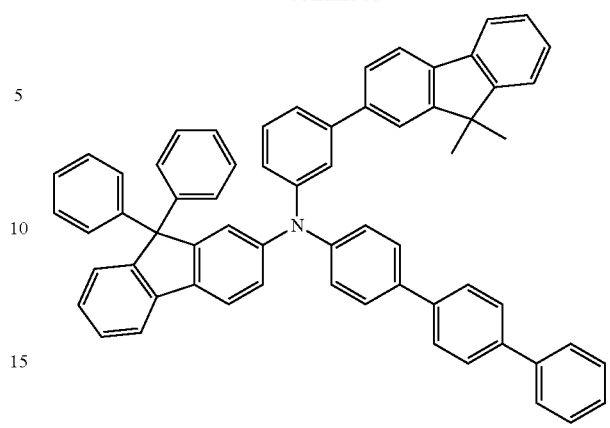
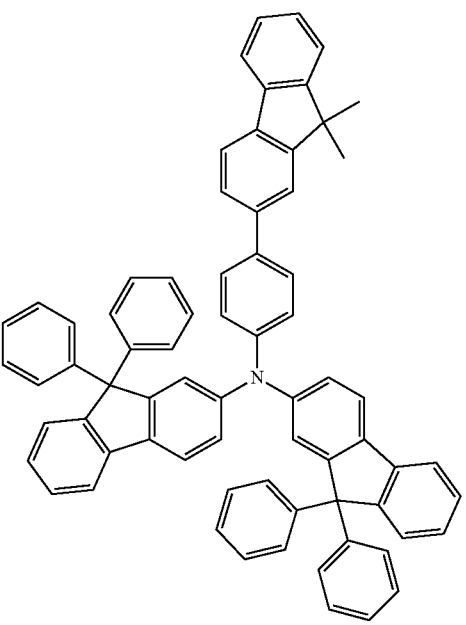
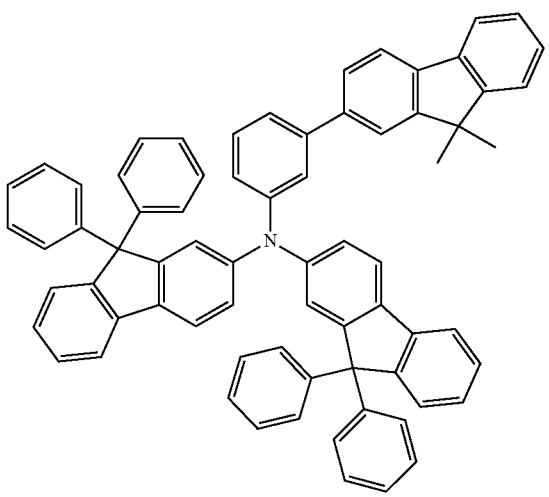

111
-continued
112
-continued
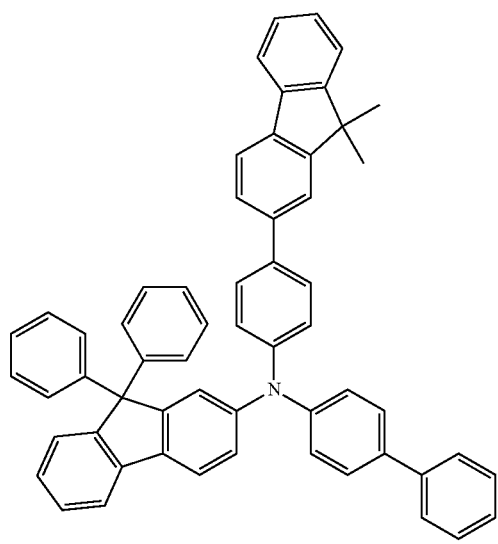
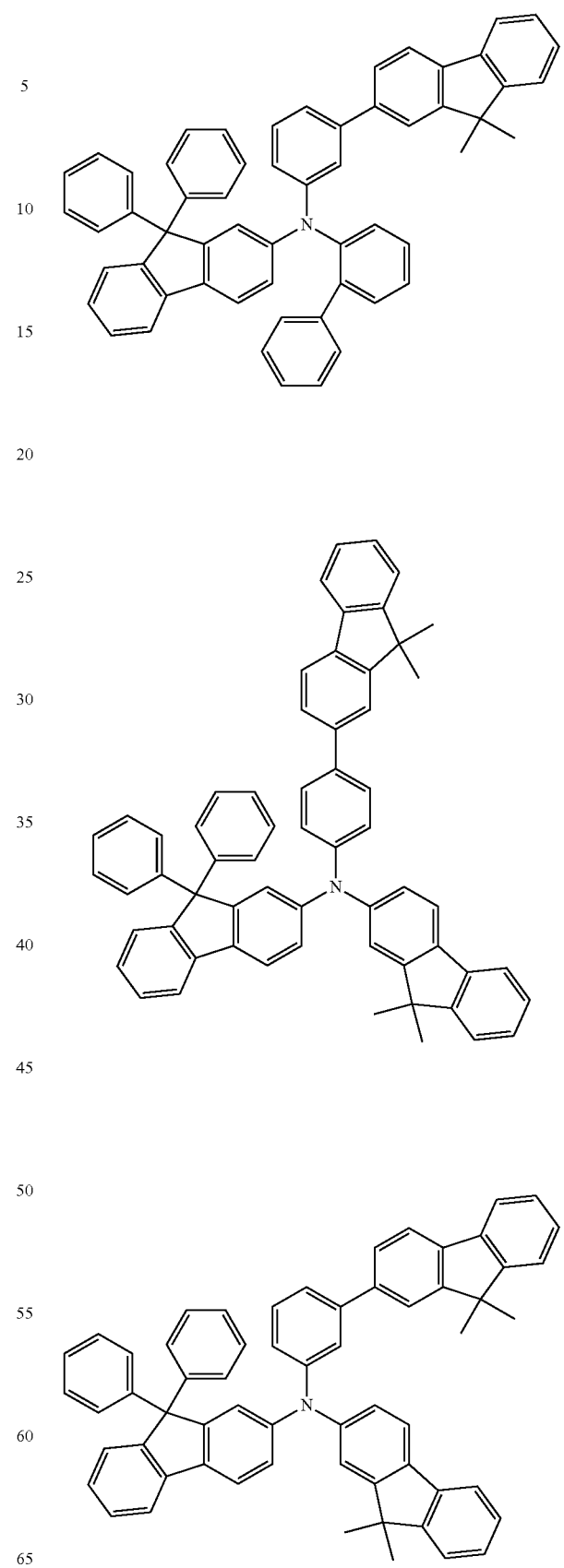

-continued

The aromatic amine derivative represented by formula (1) is useful as a material for an organic EL device, in particular, as a hole injecting layer material or a hole transporting layer material. The production method of the aromatic amine derivative of the invention is not particularly limited and one of ordinary skill in the art could easily produce it by utilizing or modifying known synthesis reactions while referring to the examples described below.

The structure of the organic EL device of the invention will be described below.

Examples of the typical device structure of the organic EL device of the invention include the following (1) to (13), although not particularly limited thereto. The device structure (8) is preferably used.
(1) anode/light emitting layer/cathode;
(2) anode/hole injecting layer/light emitting layer/cathode;
(3) anode/light emitting layer/electron injecting layer/cathode;
(4) anode/hole injecting layer/light emitting layer/electron injecting layer/cathode;
(5) anode/organic semiconductor layer/light emitting layer/cathode;
(6) anode/organic semiconductor layer/electron blocking layer/light emitting layer/cathode;
(7) anode/organic semiconductor layer/light emitting layer/adhesion improving layer/cathode;
(8) anode/hole injecting layer/hole transporting layer/light emitting layer/(electron transporting layer/) electron injecting layer/cathode;
(9) anode/insulating layer/light emitting layer/insulating layer/cathode;
(10) anode/inorganic semiconductor layer/insulating layer/light emitting layer/insulating layer/cathode;
(11) anode/organic semiconductor layer/insulating layer/light emitting layer/insulating layer/cathode;
(12) anode/insulating layer/hole injecting layer/hole transporting layer/light emitting layer/insulating layer/cathode; and
(13) anode/insulating layer/hole injecting layer/hole transporting layer/light emitting layer/(electron transporting layer/)electron injecting layer/cathode.

Since the aromatic amine derivative of the invention hardly crystallizes, it can be used in any of the above organic thin film layers. In view of driving at a lower voltage, the aromatic amine derivative is preferably used in a hole injecting layer or a hole transporting layer and more preferably in a hole transporting layer. The organic EL device employing the aromatic amine derivative of the invention is not only capable of driving at a low voltage but also has a high emission efficiency and a long lifetime.

The content of the aromatic amine derivative in an organic thin film layer, preferably in a hole injecting layer or a hole transporting layer is preferably 30 to 100 mol %, more preferably 50 to 100 mol %, still more preferably 80 to 100 mol %, and particularly preferably substantially 100 mol %, each based on the total components of the organic thin film layers.

Each layer of a preferred embodiment of an organic EL device wherein the aromatic amine derivative of the invention is used in a hole transporting layer is described below.

Substrate

The organic EL device is generally prepared on a light-transmissive substrate. The light-transmissive substrate is a substrate for supporting the organic EL device, which preferably has a light transmittance of 50% or higher to 400 to 700 nm visible lights and is preferably flat and smooth.

Examples of the light-transmissive substrate include glass plates and synthetic resin plates. Examples of the glass plate include plates of soda-lime glass, glass containing barium and strontium, lead glass, aluminosilicate glass, borosilicate glass, barium borosilicate glass, and quartz. Examples of the synthetic resin plate include plates of a polycarbonate resin, an acrylic resin, a polyethylene terephthalate resin, a polyether sulfide resin, and a polysulfone resin.

Anode

The anode has a function of injecting holes to a hole transporting layer or a light emitting layer and a material having a work function of 4 eV or more, preferably 4.5 eV or more is effective. Examples of the material for the anode include carbon, aluminum, vanadium, iron, cobalt, nickel, tungsten, silver, gold, platinum, palladium, alloys thereof, metal oxides, such as tin oxide and indium oxide, which are used as ITO substrate and NESA substrate, and organic conductive resins, such as polythiophene and polypyrrole.

The anode may be obtained by forming the above anode material into a thin film, for example, by a vapor deposition process or a sputtering process.

When the light emitted from the light emitting layer is taken through the anode, the transmittance of the anode to the emitted light is preferably higher than 10%. The sheet resistance of the anode is preferably several hundred Ω/□ or smaller. The thickness of the anode is generally 10 nm to 1 µm and preferably 10 to 200 nm, although varies depending upon the used material.

Cathode

The cathode is formed by an electrode material, such as a metal, an alloy, an electroconductive compound, or a mixture thereof, each having a small work function (less than 4 eV). Examples thereof include magnesium, calcium, tin, lead, titanium, yttrium, lithium, ruthenium, manganese, aluminum, lithium fluoride, and alloys thereof, although not particularly limited thereto. Examples of the alloy include magnesium/silver, magnesium/indium, lithium/aluminum, although not particularly limited thereto. The ratio of the alloying metals is suitably selected according to the temperature of evaporation source, atmosphere, and vacuum level. The anode and cathode may be made into two or more layered structure, if needed.

The cathode may be obtained by forming the above electrode material into a thin film, for example, by a vapor deposition process or a sputtering process.

When the light emitted from the light emitting layer is taken through the cathode, the transmittance of the cathode to the emitted light is preferably higher than 10%. The sheet resistance of the cathode is preferably several hundred Ω/□ or smaller. The thickness of the cathode is generally 10 nm to 1 µm and preferably 50 to 200 nm.

Insulating Layer

Since an electric field is applied to ultra-thin films, pixel defects due to leak and short circuit tend to easily occur. To prevent the defects, a layer made of an insulating thin film layer may be disposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. Mixtures and laminates of these compounds may be also used.

Light Emitting Layer

The light emitting layer has the following functions (1) to (3):

(1) injecting function: function of allowing holes from the anode or the hole injecting layer to be injected to the light emitting layer and allowing electrons from the cathode or the electron injecting layer to be injected to the light emitting layer, when an electric field is applied;

(2) transporting function: function of transporting injected charges (electrons and holes) by the force of the electric field; and (3) light emitting function: function of providing the field for recombination of electrons and holes to allow the emission of light.

The light emitting layer may be different in the hole injection ability and the electron injection ability, and also in the hole transporting ability and the electron transporting ability each being expressed by a hole mobility or an electron mobility, respectively. Preferably, the light emitting layer transports one kind of charges.

The host material and the doping material for use in the light emitting layer are not particularly limited. Examples thereof include a fused polycyclic aromatic compound and its derivative, such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethinyl)anthracene, and 1,4-bis(9'-ethinylanthracene)benzene; an organic metal complex such as tris(8-quinolinolato)aluminum or bis(2-methyl-8-quinolinolato)-4-(phenylphenolinato)aluminum; an arylamine derivative; a styrylamine derivative; a stilbene derivative; a coumarin derivative; a pyran derivative; an oxazone derivative; a benzothiazole derivative; a benzoxazole derivative; a benzimidazole derivative; a pyrazine derivative; a cinnamic ester derivative; a diketopyrrolopyrrole derivative; an acridone derivative; and a quinacridone derivative. Preferred are an arylamine derivative and a styrylamine derivative, with a styrylamine derivative being more preferred.

Hole Injecting Layer/Hole Transporting Layer

The hole injecting layer/hole transporting layer facilitates the injection of holes into a light emitting layer, transports holes into an emission region, and has a large hole mobility and an ionization energy generally as small as 5.7 eV or less. A material which transports holes to a light emitting layer at a smaller magnitude of electric field is preferably used for the hole injecting layer/hole transporting layer. The hole mobility of the material is preferably $10^{-4}$ cm$^2$/V·s or more when applying an electric field of $10^{-4}$ to $10^6$ V/cm.

As described above, the aromatic amine derivative of the invention is preferably used as a hole injecting layer material, particularly as a hole transporting layer material. The hole transporting layer may be formed from the aromatic amine derivative of the invention alone or in combination with another material which is not particularly limited as long as it has preferred properties mentioned above and can be selected from materials generally used as a hole transporting material in a photoconductive material and known hole transporting materials used in organic EL devices. In the present invention, a material which has a hole transporting ability and can be used in a hole transporting region is called a hole transporting material.

Examples of the material for a hole transporting layer other than the aromatic amine derivative of the invention include a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives thereof, and a polymeric material, such as polyvinyl carbazole, polysilane, and a conductive polymer, although not particularly limited thereto.

The material for a hole injecting layer is not particularly limited as long as it has preferred properties mentioned above and can be selected from materials generally used as a hole injecting material in a photoconductive material and known hole transporting materials used in organic EL devices. In the present invention, a material which has a hole injecting ability and can be used in a hole injecting region is called a hole injecting material. To enhance the electron injecting ability, an electron-accepting compound may be added to the electron injecting material.

In the organic EL device of the invention, a hexaazatriphenylene compound represented by formula (A) is preferably used as the hole injecting material.

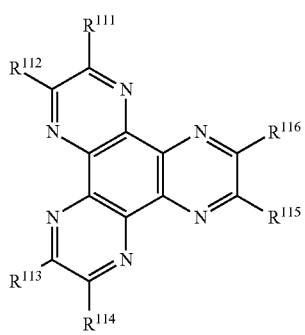

(A)

In formula (A), $R^{111}$ to $R^{116}$ independently represent a cyano group, —$CONH_2$, a carboxyl group, or —$COOR^{117}$ (wherein $R^{117}$ represents an alkyl group having 1 to 20 carbon atoms), or $R^{111}$ and $R^{112}$, $R^{113}$ and $R^{114}$, or $R^{115}$ and $R^{116}$ may be boded to each other to represent —CO—O—CO—.

In a preferred embodiment, $R^{111}$ to $R^{116}$ are the same and represent a cyano group, —$CONH_2$, a carboxyl group, or —$COOR^{117}$. In another preferred embodiment, $R^{111}$ and $R^{112}$, $R^{113}$ and $R^{114}$, and $R^{115}$ and $R^{116}$ are all bonded to each other to represent —CO—O—CO—.

Further examples of the hole transporting material usable in the organic EL device of the invention include an aromatic tertiary amine derivative and a phthalocyanine derivative.

Examples of the aromatic tertiary amine derivative include triphenylamine, tritolylamine, tolyldiphenylamine, N,N'-diphenyl-N,N'-(3-methylphenyl)-1,1'-biphenylyl-4,4'-diamine, N,N,N',N'-(4-methylphenyl)-1,1'-phenyl-4,4'-diamine, N,N,N',N'-(4-methylphenyl)-1,1'-biphenylyl-4,4'-diamine, N,N'-(methylphenyl)-N,N'-(4-n-butylphenyl)-phenanthrene-9,10-cliamine, N,N-bis(4-di-4-tolylaminophenyl)-4-phenyl-cyclohexane, and an oligomer or a polymer constituted by a unit derived from the above aromatic tertiary amines, although not particularly limited thereto.

Examples of the phthalocyanine (Pc) derivative include, but not limited to, a phthalocyanine derivative, such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc-O-GaPc, and a naphthalocyanine derivative.

In addition, the organic EL device of the invention preferably comprises a layer containing the aromatic tertiary amine derivative and/or the phthalocyanine derivative, for example, the hole transporting layer or the hole injecting layer, between a light emitting layer and an anode.

To enhance the electron injecting ability, an electron-accepting compound may be added to the electron injecting material.

Electron Injecting Layer/Electron Transporting Layer

The electron injecting layer/electron transporting layer facilitates the injection of electrons into a light emitting layer, transports electrons to an emission region, and has a large electron mobility. An adhesion improving layer is an electron injecting layer which includes a material having a particularly high adhesion to a cathode.

The emitted light is reflected by an electrode (cathode in this case). It has been known that the emitted light directly passing through an anode and the emitted light passing through the anode after reflected by the electrode interfere with each other. To effectively utilize this interference effect, the thickness of the electron transporting layer is appropriately selected from several nanometers to several micrometers. When the thickness is large, the electron mobility is preferably regulated to $10^{-5}$ $cm^2/Vs$ or more at an electric field of $10^4$ to $10^6$ V/cm in order to avoid the increase in voltage.

Examples of the material for use in the electron injecting layer include, but not limited to, fluorenone, anthraquinodimethane, diphenoquinone, thiopyraneclioxide, oxazole, oxadiazole, triazole, imidazole, perylenetetracarboxylic acid, fluorenylidenemethane, anthraquinoclimethane, anthrone, and derivatives thereof. To enhance the electron injecting ability, an electron-donating compound may be added to the electron injecting material.

Examples of other effective electron injecting material include a metal complex compound and a nitrogen-containing five-membered ring derivative.

Examples of the metal complex compound include, but not limited to, 8-hydroxyquinolinatolithium, tris(8-hydroxyquinolinato)aluminum, and bis(2-methyl-8-quinolinato)(1-naphtholato)aluminum.

The nitrogen-containing five-membered ring derivative is preferably a derivative of oxazole, thiazole, oxacliazole, thiadiazole, or triazole.

In the present invention, a benzimidazole derivative represented by any of formulae (1) to (3) is preferred as the nitrogen-containing five-membered ring derivative.

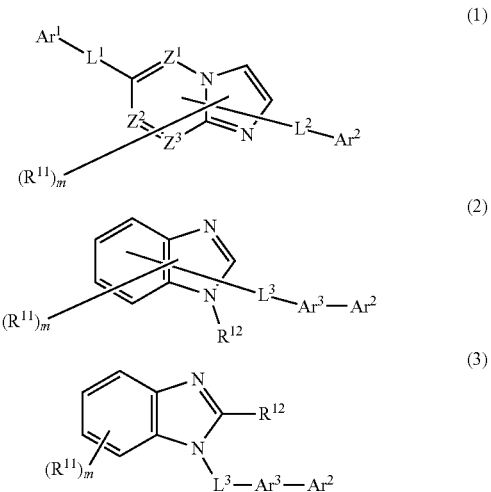

In formulae (1) to (3), $Z^1$, $Z^2$ and $Z^3$ independently represent a nitrogen atom or a carbon atom.

$R^{11}$ and $R^{12}$ independently represent a substituted or unsubstituted aryl group having 6 to 60 ring carbon atoms, a substituted or unsubstituted heteroaryl group having 3 to 60 ring carbon atoms, an alkyl group having 1 to 20 carbon atoms, a haloalkyl group having 1 to 20 carbon atoms, or an alkoxy group having 1 to 20 carbon atoms.

Subscript m is an integer of 0 to 5. When m is an integer of 2 or more, the groups $R^{11}$ may be the same or different. Two adjacent groups $R^{11}$ may be bonded to each other to form a substituted or unsubstituted aromatic hydrocarbon ring. Examples of the substituted or unsubstituted aromatic hydrocarbon ring include a benzene ring, a naphthalene ring, and an anthracene ring.

$Ar^1$ represents a substituted or unsubstituted aryl group having 6 to 60 ring carbon atoms or a substituted or unsubstituted heteroaryl group having 3 to 60 ring carbon atoms.

Ar² represents a hydrogen atom, an alkyl group having 1 to 20 carbon atoms, a haloalkyl group having 1 to 20 carbon atoms, an alkoxy group having 1 to 20 carbon atoms, a substituted or unsubstituted aryl group having 6 to 60 ring carbon atoms, or a substituted or unsubstituted heteroaryl group having 3 to 60 ring carbon atoms.

Ar³ represents a substituted or unsubstituted arylene group having 6 to 60 ring carbon atoms or a substituted or unsubstituted heteroarylene group having 3 to 60 ring carbon atoms.

$L^1$, $L^2$ and $L^3$ independently represent a single bond, a substituted or unsubstituted arylene group having 6 to 60 ring carbon atoms, a substituted or unsubstituted fused heterocyclic group having 9 to 60 ring atoms or a substituted or unsubstituted fluorenylene group.

In the organic EL device of the invention, the layer including the aromatic amine derivative of the invention may further include an emission material, a doping material, a hole injecting material or an electron injecting material.

The layer including the aromatic amine derivative of the invention may further include, if necessary, a material which is known as an emission material, a doping material, a hole injecting material, or an electron injecting material, and the aromatic amine derivative may be used as a doping material.

By forming two or more organic thin film layers in an organic EL device, the decrease in the luminance and the lifetime due to the quenching can be prevented. If necessary, an emission material, a doping material, a hole injecting material, and an electron injecting material may be used in combination. The emission luminance and the emission efficiency can be improved and the emission color can be changed by the use of a doping material.

The hole transporting layer of the organic EL device of the invention may be made into two-layered structure, i.e., a first hole transporting layer (anode side) and a second hole transporting layer (cathode side). The aromatic amine derivative of the invention may be used in any of the first hole transporting layer and the second hole transporting layer.

In view of improving the stability to temperature, humidity, and atmosphere, the surface of the organic EL device of the present invention may be provided with a protective layer or the entire device may be protected by silicone oil or a resin.

Each layer of the organic EL device of the invention may be formed by any of a dry film-forming method, such as vacuum deposition, sputtering, plasma, and ion plating, and a wet film-forming method, such as spin coating, clipping, and flow coating.

In a dry film-forming method, the material for each layer is dissolved or dispersed in an appropriate solvent, such as ethanol, chloroform, tetrahydrofuran, and dioxane, and the obtained solution or dispersion is formed into a thin film. The solution and dispersion may contain a resin or an additive to improve the film-forming property and prevent a pin hole in the layer. Examples of the resin include insulating resins, such as polystyrene, polycarbonate, polyarylate, polyester, polyamide, polyurethane, polysulfone, polymethyl methacrylate, polymethyl acrylate, cellulose, and copolymers thereof; photoconductive resins, such as poly-N-vinylcarbazole and polysilane; and conductive resins such as polythiophene and polypyrrole. Examples of the additive include an antioxidant, an ultraviolet absorber, and a plasticizer.

The thickness of each layer is not particularly limited and selected so as to obtain a good device performance. An excessively large thickness increases the applied voltage sufficient for obtaining a certain level of optical output, resulting in a poor efficiency. An excessively small thickness causes a pin hole, so a sufficient emission luminance cannot be obtained even when an electric field is applied. The thickness is preferably 5 nm to 10 μm and more preferably 10 nm to 0.2 μm.

EXAMPLES

The present invention will be described below in more detail with reference to the examples. However, it should be noted that the scope of the invention is not limited thereto.

Intermediate Synthesis 1-1 (Synthesis of Intermediate 1-1)

Under an argon atmosphere, into a mixture of 28.3 g (100.0 mmol) of 4-iodobromobenzene, 22.3 g (105.0 mmol) of dibenzofuran-4-boronic acid, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added, and the resultant mixture was stirred for 10 h while refluxing under heating.

After the reaction, the obtained mixture was cooled to room temperature and extracted with dichloromethane in a separatory funnel. The organic layer was dried over MgSO$_4$, and then filtered and condensed. The condensate was purified by silica gel column chromatography to obtain 26.2 g of a white solid, which was identified as the intermediate 1-1 by FD-MS analysis (Field Desorption Mass Spectrometry Analysis) (yield: 81%).

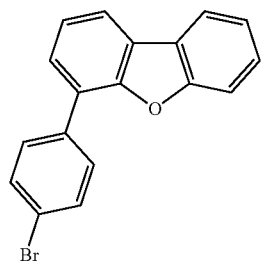

Intermediate 1-1

Intermediate Synthesis 1-2 (Synthesis of Intermediate 1-2)

Under an argon atmosphere, into a mixture of 24.0 g (112.0 mmol) of 4'-bromoacetanilide, 28.6 g (135.0 mmol) of dibenzofuran-4-boronic acid, and 2.6 g (2.24 mmol) of Pd[PPh$_3$]$_4$, 450 ml of toluene, 100 ml of dimethoxyethane, and 110 ml (220.0 mmol) of a 2 M aqueous solution of Na$_2$CO$_3$ were added, and the resultant mixture was stirred for 10 h while refluxing under heating.

After the reaction, the obtained mixture was cooled to room temperature, and the precipitated crystal was collected by filtration. The collected crystal was dissolved in tetrahydrofuran and filtered through celite/silica gel. The filtrate was condensed under reduced pressure. The obtained residue was washed with methanol/hexane and dried to obtain 18.0 g of a white solid, which was identified as the intermediate 1-2 by FD-MS analysis (yield: 53%)

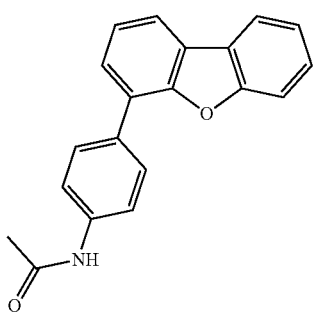

Intermediate 1-2

Intermediate Synthesis 1-3 (Synthesis of Intermediate 1-3)

Into 18.0 g (59.7 mmol) of the intermediate 1-2, 120 ml of xylene, 1200 ml of water, and 60 ml of ethanol were added, and the resultant mixture was stirred. After adding 20.0 g (360.0 mmol) of potassium hydroxide, the mixture was stirred for 10 h while refluxing under heating.

After the reaction, the obtained mixture was cooled to room temperature and extracted with toluene in a separatory funnel. The organic layer was dried over MgSO$_4$, and then filtered and condensed. The obtained residue was recrystallized from xylene. The crystal was collected by filtration and dried to obtain 14.7 g of a white solid, which was identified as the intermediate 1-3 by FD-MS analysis (yield: 95%).

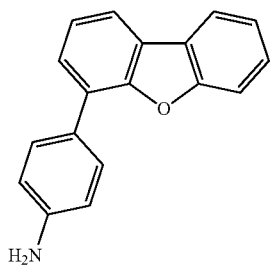

Intermediate 1-3

Intermediate Synthesis 1-4 (Synthesis of Intermediate 1-4)

Under a nitrogen atmosphere, 150 g (0.89 mol) of dibenzofuran was dissolved in 1000 ml of acetic acid under heating. After further adding 188 g (1.18 mol) of bromine dropwise, the resultant mixture was stirred at room temperature for 20 h.

The precipitated crystal was collected by filtration and washed successively with acetic acid and water. The recrystallization of the crude product from methanol was repeated several times to obtain 66.8 g of a white crystal, which was identified as the intermediate 1-4 by FD-MS analysis (yield: 30%).

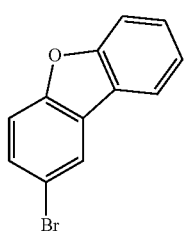

Intermediate 1-4

Intermediate Synthesis 1-5 (Synthesis of Intermediate 1-5)

Under an argon atmosphere, into 24.7 g (100.0 mmol) of the intermediate 1-4, 400 ml of dry tetrahydrofuran was added and the resultant mixture was cooled to −40° C. Further, 63 ml (100.0 mmol) of a 1.6 M hexane solution of n-butyllithium was gradually added. The reaction solution was stirred for one hour while heating to 0° C. Then, the reaction solution was cooled again to −78° C. and then a solution of 26.0 g (250.0 mmol) of trimethyl borate in 50 ml of dry tetrahydrofuran was added dropwise. After the dropwise addition, the reaction solution was stirred at room temperature for 5 h. After adding 200 ml of a 1 N hydrochloric acid, the solution was stirred for one hour and then the aqueous layer was removed. The organic layer was dried over MgSO$_4$, and the solvent was evaporated off under reduced pressure. The obtained solid was washed with toluene to obtain 15.2 g of a white crystal (yield: 72%).

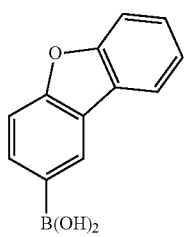

Intermediate 1-5

Intermediate Synthesis 1-6 (Synthesis of Intermediate 1-6)

Under an argon atmosphere, into a mixture of 28.3 g (100.0 mmol) of 4-iodobromobenzene, 22.3 g (105.0 mmol) of the intermediate 1-5, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added, and the resultant mixture was stirred for 10 h while refluxing under heating.

After the reaction, the obtained mixture was extracted with dichloromethane in a separatory funnel. The organic layer was dried over MgSO$_4$, and then filtered and condensed. The condensate was purified by silica gel column chromatography to obtain 24.2 g of a white solid, which was identified as the intermediate 1-6 by FD-MS analysis (yield: 75%).

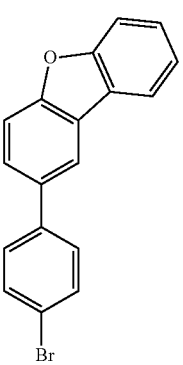

Intermediate 1-6

Intermediate Synthesis 1-7 (Synthesis of Intermediate 1-7)

In the same manner as in Intermediate Synthesis 1-2 except for using 28.6 g of the intermediate 1-5 in place of dibenzofuran-4-boronic acid, 19.1 g of a white solid was obtained, which was identified as the intermediate 1-7 by FD-MS analysis (yield: 56%).

Intermediate 1-7

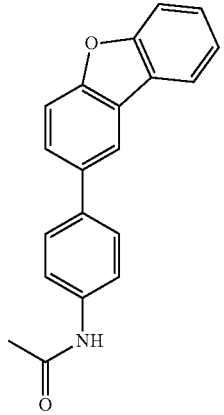

Intermediate Synthesis 1-8 (Synthesis of Intermediate 1-8)

In the same manner as in Intermediate Synthesis 1-3 except for using 18.0 g of the intermediate 1-7 in place of the intermediate 1-2, 14.5 g of a white solid was obtained, which was identified as the intermediate 1-8 by FD-MS analysis (yield: 93%).

Intermediate 1-8

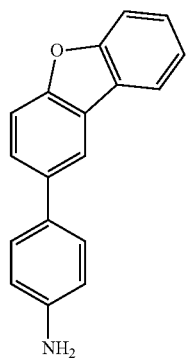

Intermediate Synthesis 1-9 (Synthesis of Intermediate 1-9)

Under an argon atmosphere, into a mixture of 28.3 g (100.0 mmol) of 4-iodobromobenzene, 23.9 g (105.0 mmol) of dibenzothiophene-4-boronic acid, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added, and the resultant mixture was stirred for 10 h while refluxing under heating.

After the reaction, the obtained mixture was cooled to room temperature, and extracted with dichloromethane in a separatory funnel. The organic layer was dried over MgSO$_4$, and then filtered and condensed. The condensate was purified by silica gel column chromatography to obtain 27.1 g of a white solid, which was identified as the intermediate 1-9 by FD-MS analysis (Field Desorption Mass Spectrometry Analysis) (yield: 80%).

Intermediate 1-9

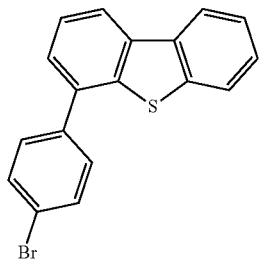

Intermediate Synthesis 1-10 (Synthesis of Intermediate 1-10)

Under an argon atmosphere, into a mixture of 24.0 g (112.0 mmol) of 4'-bromoacetanilide, 30.8 g (135.0 mmol) of dibenzothiophene-4-boronic acid, and 2.6 g (2.24 mmol) of Pd[PPh$_3$]$_4$, 450 ml of toluene, 100 ml of dimethoxyethane, and 110 ml (220.0 mmol) of a 2 M aqueous solution of Na$_2$CO$_3$ were added, and the resultant mixture was stirred for 10 h while refluxing under heating.

After the reaction, the obtained mixture was cooled to room temperature, and the precipitated crystal was collected by filtration. The collected crystal was dissolved in tetrahydrofuran and filtered through celite/silica gel. The filtrate was condensed under reduced pressure. The obtained residue was washed with methanol/hexane and dried to obtain 17.8 g of a white solid, which was identified as the intermediate 1-10 by FD-MS analysis (yield: 50%)

Intermediate 1-10

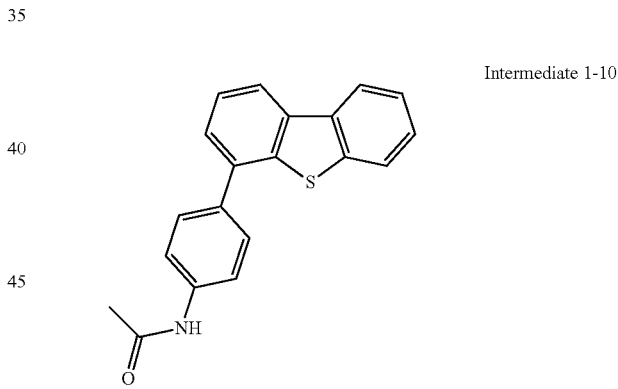

Intermediate Synthesis 1-11 (Synthesis of Intermediate 1-11)

Into 18.0 g (56.1 mmol) of the intermediate 1-10, 120 ml of xylene, 1200 ml of water, and 60 ml of ethanol were added, and the resultant mixture was stirred. After adding 20.0 g (360.0 mmol) of potassium hydroxide, the mixture was stirred for 10 h while refluxing under heating.

After the reaction, the obtained mixture was cooled to room temperature and extracted with toluene in a separatory funnel. The organic layer was dried over MgSO$_4$ and then filtered and condensed. The obtained residue was recrystallized from xylene. The crystal was collected by filtration and dried to obtain 14.7 g of a white solid, which was identified as the intermediate 1-11 by FD-MS analysis (yield: 95%).

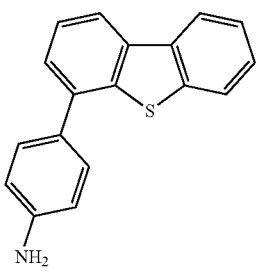

Intermediate 1-11

Intermediate Synthesis 1-12 (Synthesis of Intermediate 1-12)

In the same manner as in Intermediate Synthesis 1-5 except for using 26.3 g of 2-bromodibenzothiophene in place of the intermediate 1-4, 15.0 g of a white solid was obtained (yield: 66%).

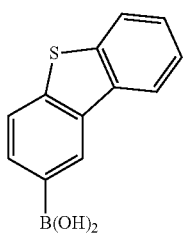

Intermediate 1-12

Intermediate Synthesis 1-13 (Synthesis of Intermediate 1-13)

In the same manner as in Intermediate Synthesis 1-6 except for using 23.9 g of the intermediate 1-12 in place of the intermediate 1-5, 25.4 g of a white solid was obtained, which was identified as the intermediate 1-13 by FD-MS analysis (yield: 75%).

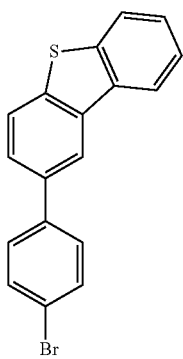

Intermediate 1-13

Intermediate Synthesis 1-14 (Synthesis of Intermediate 1-14)

In the same manner as in Intermediate Synthesis 1-2 except for using 30.8 g of the intermediate 1-12 in place of dibenzofuran-4-boronic acid, 18.1 g of a white solid was obtained, which was identified as the intermediate 1-14 by FD-MS analysis (yield: 51%).

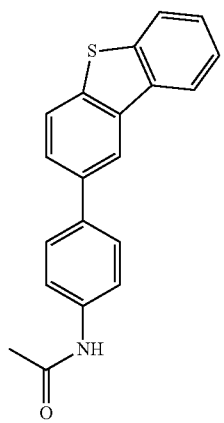

Intermediate 1-14

Intermediate Synthesis 1-15 (Synthesis of Intermediate 1-15)

In the same manner as in Intermediate Synthesis 1-3 except for using 18.0 g of the intermediate 1-14 in place of the intermediate 1-2, 13.9 g of a white solid was obtained, which was identified as the intermediate 1-15 by FD-MS analysis (yield: 90%).

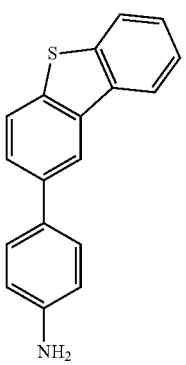

Intermediate 1-15

Intermediate Synthesis 2-1 (Synthesis of Intermediate 2-1)

Under an argon atmosphere, into a mixture of 19.9 g (50.0 mmol) of 2-bromo-9,9'-diphenylfluorene, 13.0 g (50.0 mmol) of the intermediate 1-3, and 9.6 g (100.0 mmol) of t-butoxysodium, 250 ml of dry toluene was added, and the resultant mixture was stirred. After adding 225 mg (1.0 mmol) of palladium acetate and 202 mg (1.0 mmol) of tri-t-butylphosphine, the mixture was allowed to react at 80° C. for 8 h.

After cooling, the reaction mixture was filtered through celite/silica gel. The filtrate was condensed under reduced pressure. The obtained residue was recrystallized from toluene and the crystal was collected by filtration and dried to obtain 23.0 g of a white solid, which was identified as the intermediate 2-1 by FD-MS analysis (yield: 80%).

Intermediate 2-1

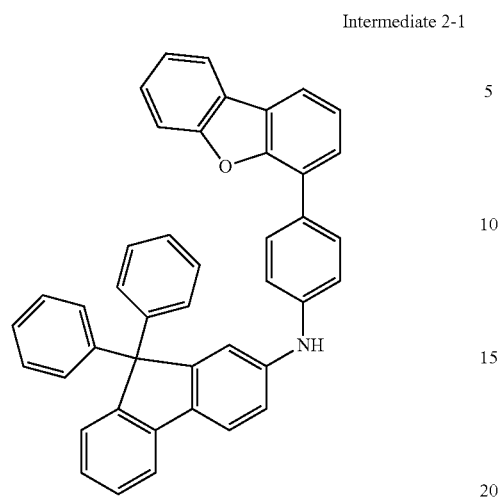

Intermediate 2-3

Intermediate Synthesis 2-2 (Synthesis of Intermediate 2-2)

In the same manner as in Intermediate Synthesis 2-1 except for using 13.0 g of the intermediate 1-8 in place of the intermediate 1-3, 23.2 g of a white solid was obtained, which was identified as the intermediate 2-2 by FD-MS analysis (yield: 81%).

Intermediate Synthesis 2-4 (Synthesis of Intermediate 2-4)

In the same manner as in Intermediate Synthesis 2-1 except for using 13.8 g of the intermediate 1-11 in place of the intermediate 1-3, 23.7 g of a white solid was obtained, which was identified as the intermediate 2-4 by FD-MS analysis (yield: 80%).

Intermediate 2-2

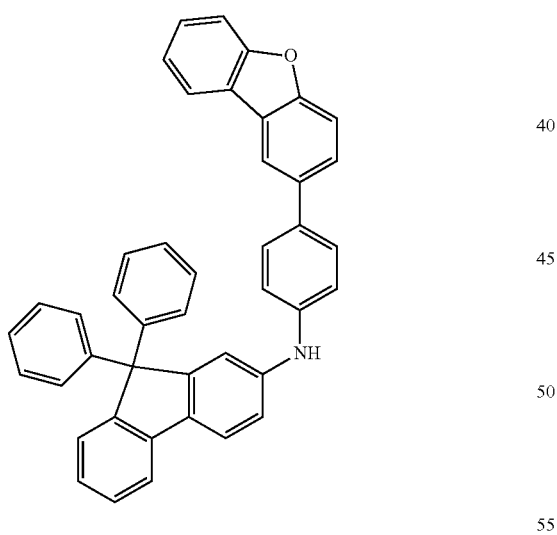

Intermediate 2-4

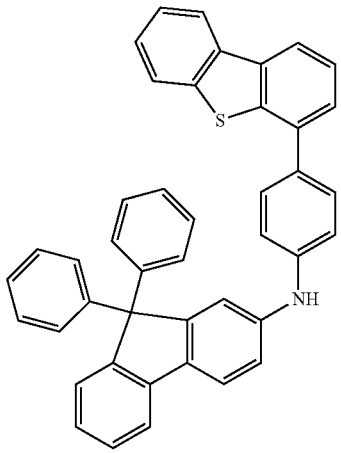

Intermediate Synthesis 2-3 (Synthesis of Intermediate 2-3)

In the same manner as in Intermediate Synthesis 2-1 except for using 10.5 g of 2-amino-9,9'-dimethylfluorene in place of the intermediate 1-3, 19.7 g of a white solid was obtained, which was identified as the intermediate 2-3 by FD-MS analysis (yield: 75%).

Intermediate Synthesis 2-5 (Synthesis of Intermediate 2-5)

In the same manner as in Intermediate Synthesis 2-1 except for using 13.8 g of the intermediate 1-15 in place of the intermediate 1-3, 22.2 g of a white solid was obtained, which was identified as the intermediate 2-5 by FD-MS analysis (yield: 75%).

Intermediate 2-5

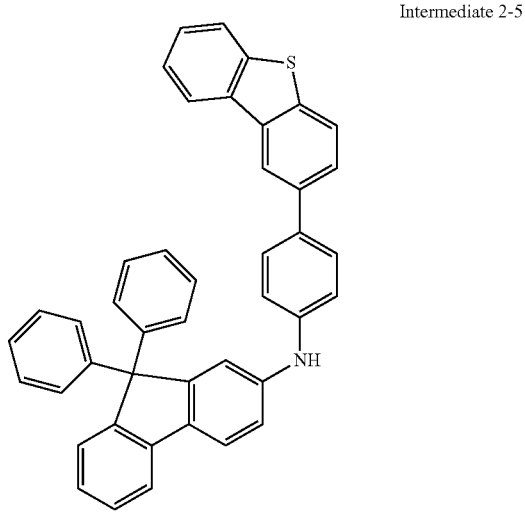 [SMILES: c1ccc(C2(c3ccccc3)c3ccccc3-c3ccc(Nc4ccc(-c5ccc6sc7ccccc7c6c5)cc4)cc32)cc1]

Synthesis Example 1 (Production of Aromatic Amine Derivative H1)

Under an argon atmosphere, into a mixture of 3.2 g (10.0 mmol) of the intermediate 1-1, 5.8 g (10.0 mmol) of the intermediate 2-1, 0.14 g (0.15 mmol) of $Pd_2(dba)_3$, 0.087 g (0.3 mmol) of $P(tBu)_3HBF_4$, and 1.9 g (20.0 mmol) of t-butoxysodium, 50 ml of dry xylene was added, and the resultant mixture was refluxed for 8 h under heating.

After the reaction, the reaction liquid was cooled to 50° C. and filtered through celite/silica gel. The filtrate was condensed and the obtained condensate was purified by silica gel column chromatography to obtain a white solid. The crude product was recrystallized from toluene to obtain 3.7 g of a white crystal, which was identified as the aromatic amine derivative H1 by FD-MS analysis (yield: 45%).

H1

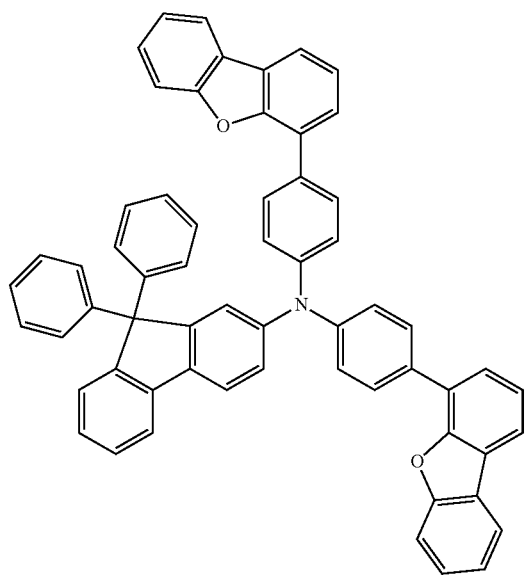

Synthesis Example 2 (Production of Aromatic Amine Derivative H2)

In the same manner as in Synthesis Example 1 except for using 3.2 g of the intermediate 1-6 in place of the intermediate 1-1 and using 5.8 g of the intermediate 2-2 in place of the intermediate 2-1, 5.2 g of a white crystal was obtained, which was identified as the aromatic amine derivative H2 by FD-MS analysis (yield: 63%).

H2

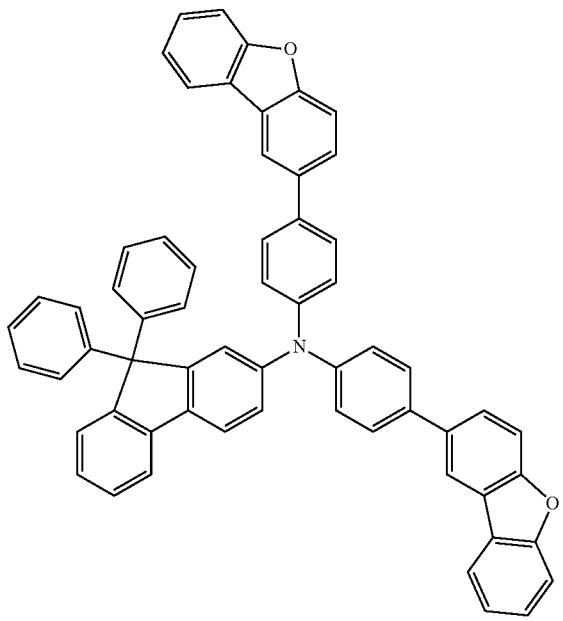

Synthesis Example 3 (Production of Aromatic Amine Derivative H3)

In the same manner as in Synthesis Example 1 except for using 3.2 g of the intermediate 1-6 in place of the intermediate 1-1, 4.5 g of a white crystal was obtained, which was identified as the aromatic amine derivative H3 by FD-MS analysis (yield: 55%).

H3

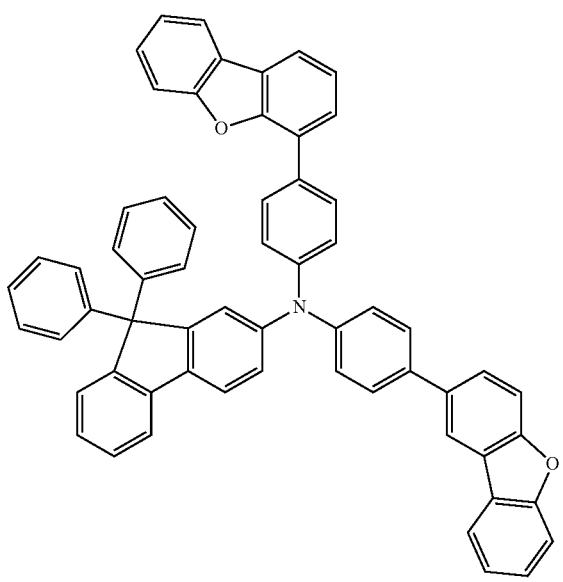

Synthesis Example 4 (Production of Aromatic Amine Derivative H4)

In the same manner as in Synthesis Example 1 except for using 2.3 g of 4-bromobiphenyl in place of the intermediate 1-1, 3.6 g of a white crystal was obtained, which was identified as the aromatic amine derivative H4 by FD-MS analysis (yield: 50%).

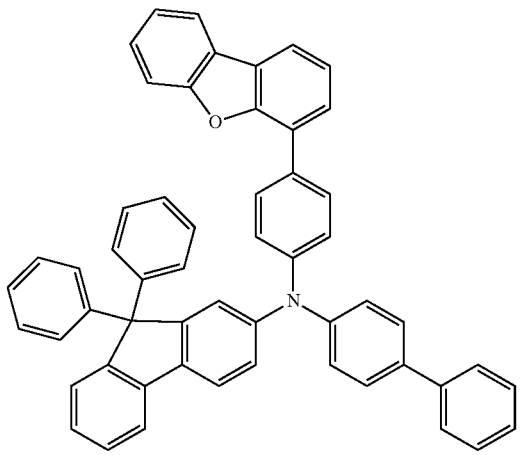

Synthesis Example 5 (Production of Aromatic Amine Derivative H5)

Under an argon atmosphere, into a mixture of 2.3 g (10.0 mmol) of 2-bromobiphenyl, 5.3 g (10.0 mmol) of the intermediate 2-3, 0.14 g (0.15 mmol) of $Pd_2(dba)_3$, 0.087 g (0.3 mmol) of $P(tBu)_3HBF_4$, and 1.9 g (20.0 mmol) of t-butoxysodium, 50 ml of dry xylene was added, and the resultant mixture was refluxed for 8 h under heating.

After the reaction, the reaction liquid was cooled to 50° C. and filtered through celite/silica gel. The filtrate was condensed and the obtained condensate was purified by silica gel column chromatography to obtain a white solid. The crude product was recrystallized from toluene to obtain 3.1 g of a white crystal, which was identified as the aromatic amine derivative H5 by FD-MS analysis (yield: 45%).

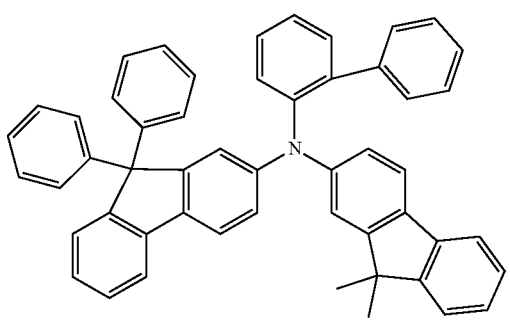

Synthesis Example 6 (Production of Aromatic Amine Derivative H6)

In the same manner as in Synthesis Example 5 except for using 2.3 g of 4-bromobiphenyl in place of 2-bromobiphenyl, 2.7 g of a white crystal was obtained, which was identified as the aromatic amine derivative H6 by FD-MS analysis (yield: 40%).

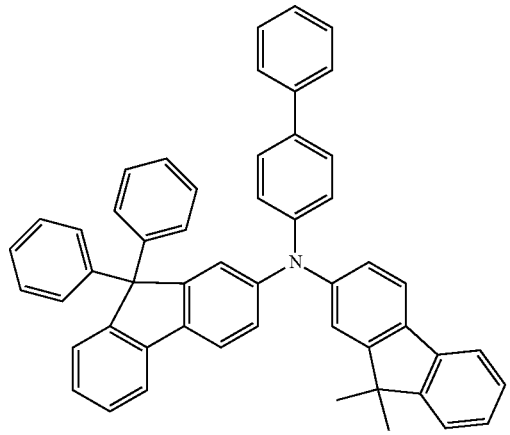

Synthesis Example 7 (Production of Aromatic Amine Derivative H7)

In the same manner as in Synthesis Example 1 except for using 3.4 g of the intermediate 1-9 in place of the intermediate 1-1 and using 5.9 g of the intermediate 2-4 in place of the intermediate 2-1, 4.7 g of a white crystal was obtained, which was identified as the aromatic amine derivative H7 by FD-MS analysis (yield: 55%).

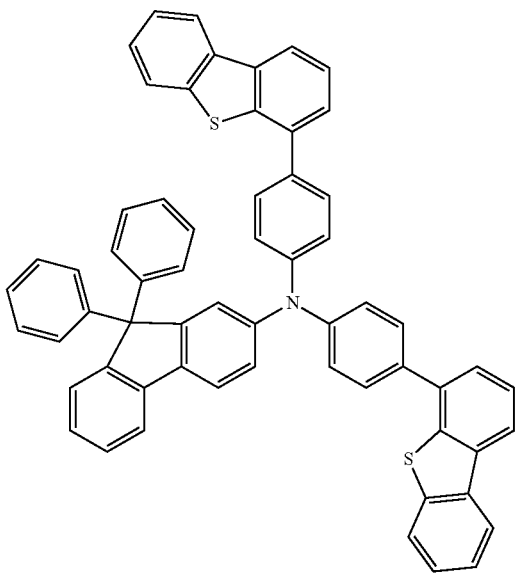

Synthesis Example 8 (Production of Aromatic Amine Derivative H8)

In the same manner as in Synthesis Example 1 except for using 3.4 g of the intermediate 1-13 in place of the intermediate 1-1 and using 5.9 g of the intermediate 2-5 in place of the intermediate 2-1, 5.1 g of a white crystal was obtained, which was identified as the aromatic amine derivative H8 by FD-MS analysis (yield: 55%).

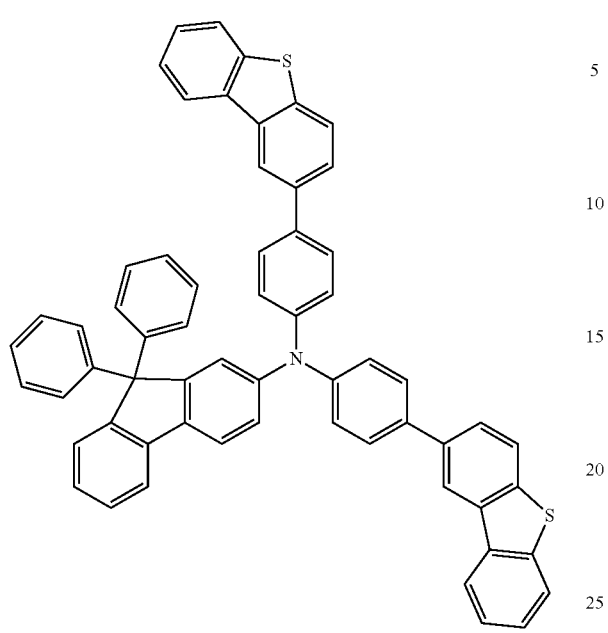

Example 1-1

Production of Organic EL Device

A glass substrate with an ITO transparent electrode line having a size of 25 mm×75 mm×1.1 mm (manufactured by GEOMATEC Co., Ltd.) was ultrasonically cleaned in isopropyl alcohol for 5 min and then UV (ultraviolet)/ozone cleaned for 30 min.

The cleaned glass substrate with the transparent electrode line was mounted on the substrate holder of a vacuum deposition apparatus. First, the following electron-accepting compound A was vapor-deposited onto the surface on the side where the transparent electrode line was formed so as to cover the transparent electrode, thereby forming a film A having a thickness of 5 nm.

On the film A, the following aromatic amine derivative X1 as a first hole transporting material was vapor-deposited to form a first hole transporting layer having a thickness of 160 nm. Successively after the formation of the first hole transporting layer, the aromatic amine derivative H1 as a second hole transporting material was vapor-deposited to form a second hole transporting layer having a thickness of 10 nm.

On the hole transporting layer, the host compound BH and the dopant compound BD were vapor co-deposited into a film having a thickness of 25 nm, to form a light emitting layer. The concentration of the dopant compound BD was 4% by mass.

On the light emitting layer, the compound ET1 was vapor-deposited in a thickness of 20 nm and then the compound ET2 and Li were vapor co-deposited each in a thickness of 10 nm and 25 nm, thereby forming an electron transporting/injecting layer. The concentration of Li was 4% by mass.

Then, metallic Al was deposited in a thickness of 80 nm to form a cathode, thereby producing an organic EL device.

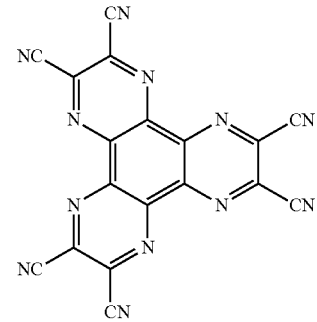

(A)

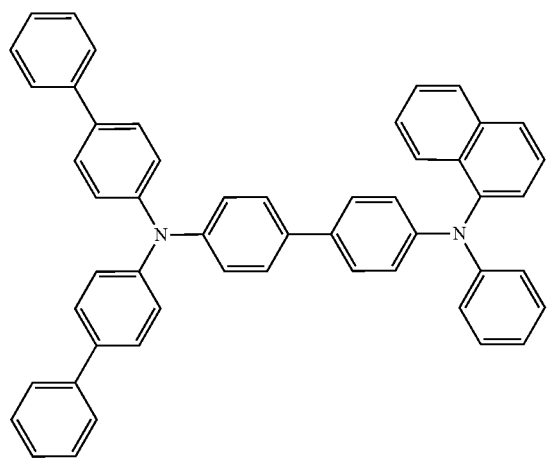

(X1)

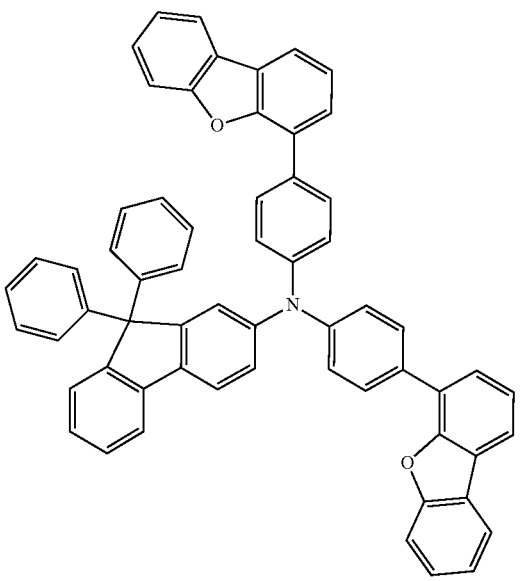

(H1)

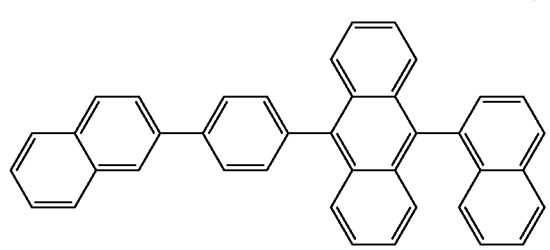

(BH)

(BD)
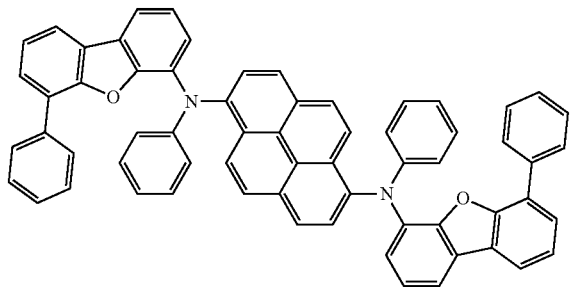
(ET1)
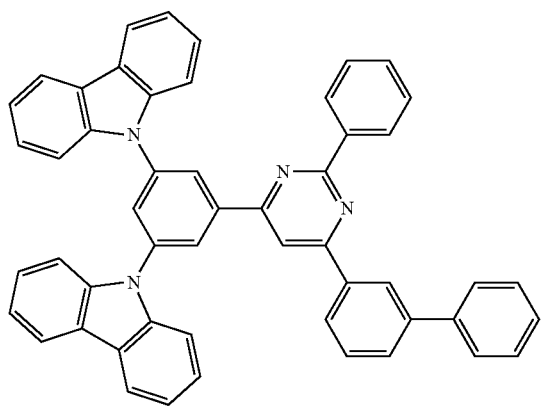
(ET2)
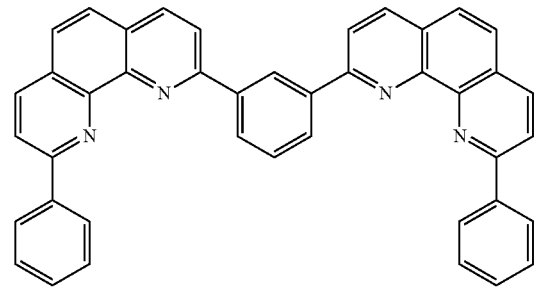
Examples 1-2 to 1-6
Each organic EL device of Examples 1-2 to 1-6 was produced in the same manner as in Example 1-1 except for using each aromatic amine derivative listed in Table 1 as the second hole transporting material.
(H2)
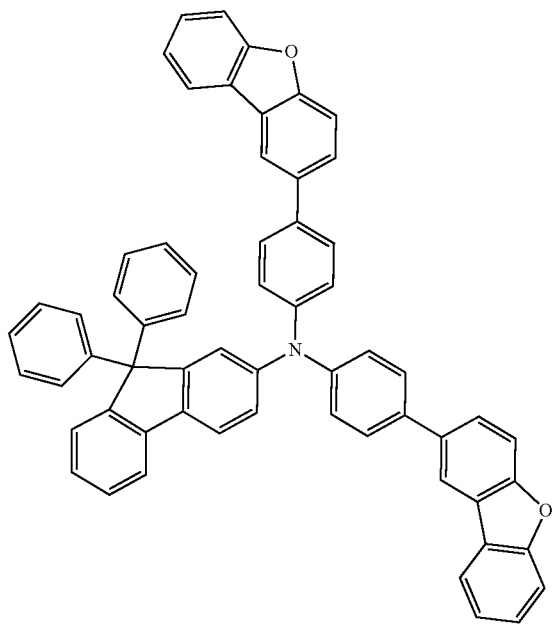
(H3)
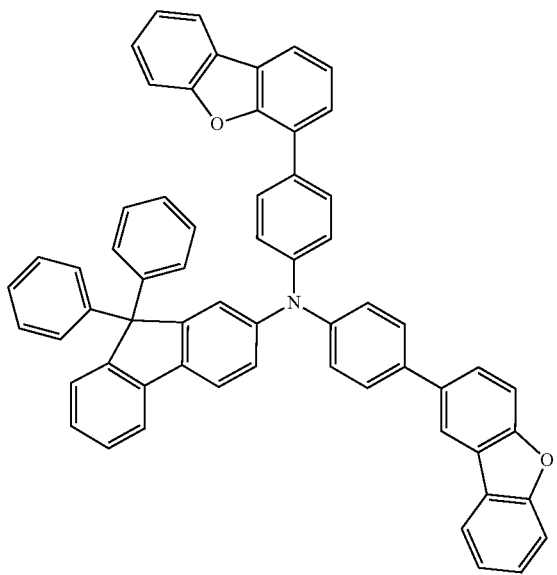

(H4)
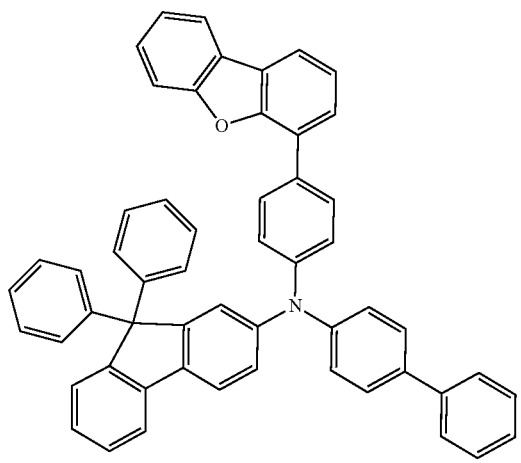
(H8)
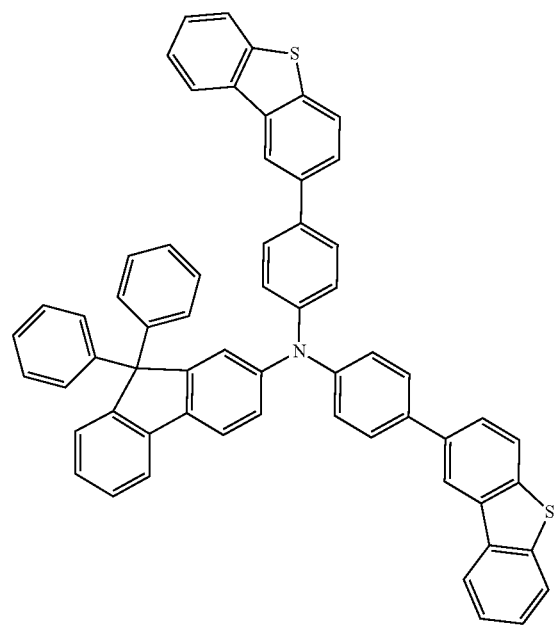
(H7)
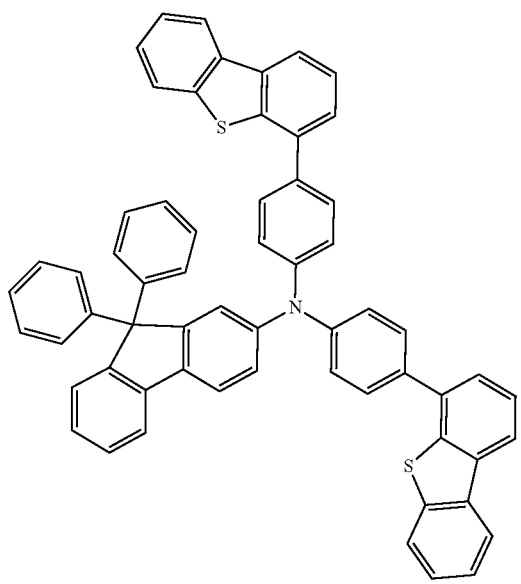
Comparative Examples 1-1 and 1-2
Each organic EL device of Comparative Examples 1-1 and 1-2 was produced in the same manner as in Example 1-1 except for using each aromatic amine derivative listed in Table 1 as the second hole transporting material.
Comparative compound 1
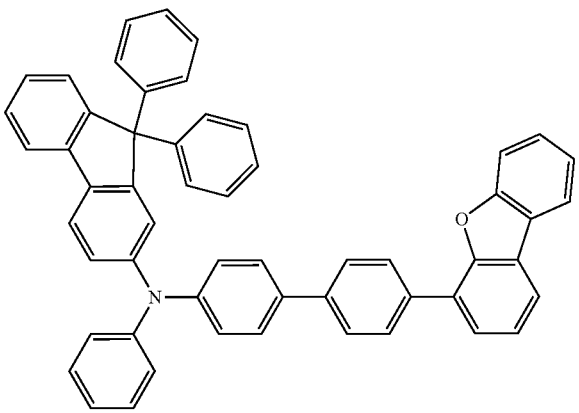

-continued

Comparative compound 2

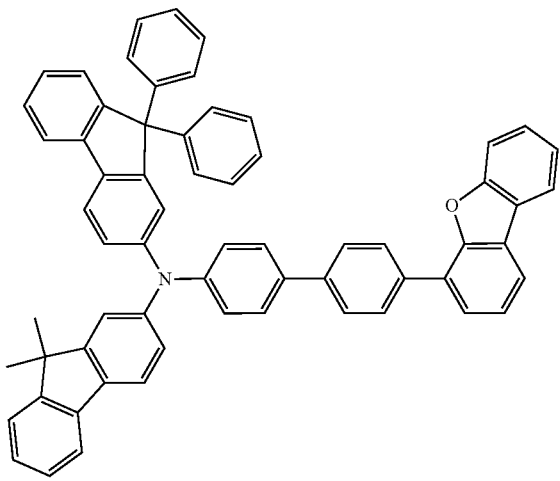

Evaluation of Emission Performance of Organic EL Device

Each organic EL device thus produced was measured for the luminance (L) and the current density by allowing the device to emit light under a direct current drive. Using the measured results, the current efficiency (L/J) and the driving voltage (V) at a current density of 10 mA/cm² were determined. In addition, the organic EL device was measured for the lifetime at a current density of 50 mA/cm². The 80% lifetime is the time taken until the luminance was reduced to 80% of the initial luminance when driving the device at constant current. The results are shown in Table 1.

TABLE 1

| | | Measured Results | | |
|---|---|---|---|---|
| First, hole transporting material | Second hole transporting material | Emission efficiency (cd/A) @ 10 mA/cm² | Driving voltage (V) @ 10 mA/cm² | 80% Lifetime (h) |
| Examples | | | | |
| 1-1 | X1 | H1 | 6.5 | 4.2 | 230 |
| 1-2 | X1 | H2 | 6.9 | 4.2 | 190 |
| 1-3 | X1 | H3 | 7.2 | 4.2 | 220 |
| 1-4 | X1 | H4 | 6.2 | 4.0 | 170 |
| 1-5 | X1 | H7 | 6.4 | 4.1 | 210 |
| 1-6 | X1 | H8 | 7.0 | 4.1 | 180 |
| Comparative Examples | | | | |
| 1-1 | X1 | comparative compound 1 | 5.5 | 4.2 | 120 |
| 1-2 | X1 | comparative compound 2 | 5.2 | 4.0 | 100 |

The results of Table 1 show that an organic EL device having a high efficiency even when driving it at a low voltage and having a long lifetime is obtained by using the aromatic amine derivative of the invention.

Example 2-1

Production of Organic EL Device

A glass substrate with an ITO transparent electrode line having a size of 25 mm×75 mm×1.1 mm (manufactured by GEOMATEC Co., Ltd.) was ultrasonically cleaned in isopropyl alcohol for 5 min and then UV (ultraviolet)/ozone cleaned for 30 min.

The cleaned glass substrate with the transparent electrode line was mounted on the substrate holder of a vacuum deposition apparatus. First, the following electron-accepting compound A was vapor-deposited onto the surface on the side where the transparent electrode line was formed so as to cover the transparent electrode, thereby forming a film A having a thickness of 5 nm.

On the film A, the following aromatic amine derivative H5 as a first hole transporting material was vapor-deposited to form a first hole transporting layer having a thickness of 160 nm. Successively after the formation of the first hole transporting layer, the aromatic amine derivative Y1 as a second hole transporting material was vapor-deposited to form a second hole transporting layer having a thickness of 10 nm.

On the hole transporting layer, the host compound BH and the dopant compound BD were vapor co-deposited into a film having a thickness of 25 nm, to form a light emitting layer. The concentration of the dopant compound BD was 4% by mass.

On the light emitting layer, the compound ET1 was vapor-deposited in a thickness of 20 nm and then the compound ET2 and Li were vapor co-deposited each in a thickness of 10 nm and 25 nm, thereby forming an electron transporting/injecting layer. The concentration of Li was 4% by mass.

Then, metallic Al was deposited in a thickness of 80 nm to form a cathode, thereby producing an organic EL device.

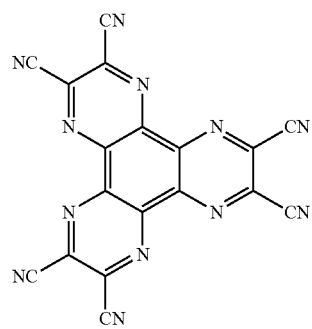

(A)

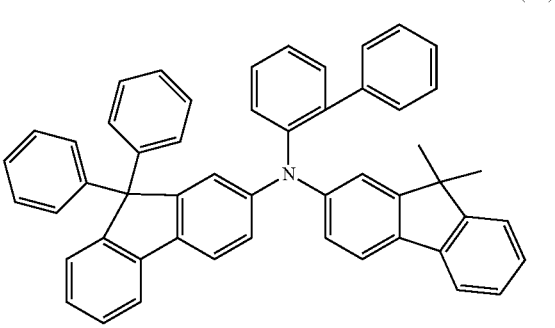

(H5)

-continued (Y1)
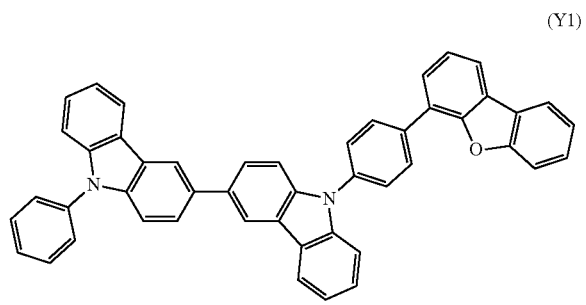

(BH)
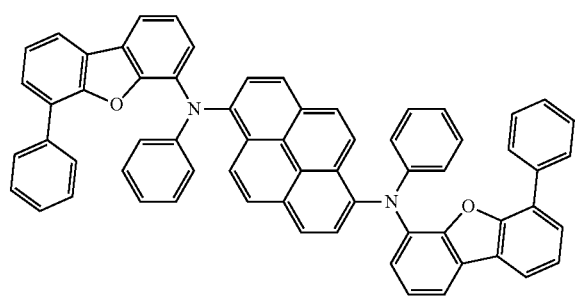

(BD)

(ET1)
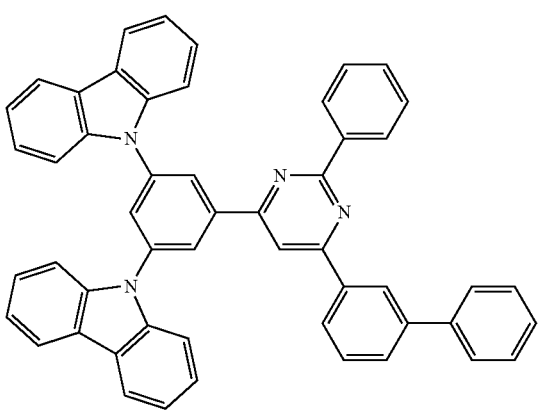

(ET2)
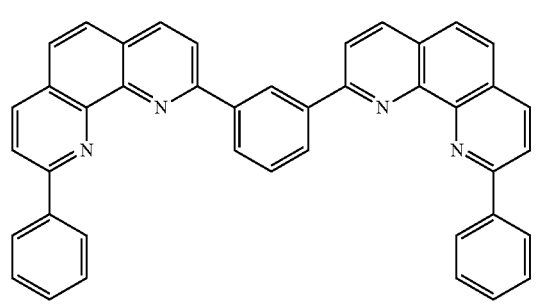

Examples 2-2 to 2-4

Each organic EL device of Examples 2-2 to 2-4 was produced in the same manner as in Example 2-1 except for using the aromatic amine derivatives listed in Table 2 as the first hole transporting material and the second hole transporting material.

(H6)
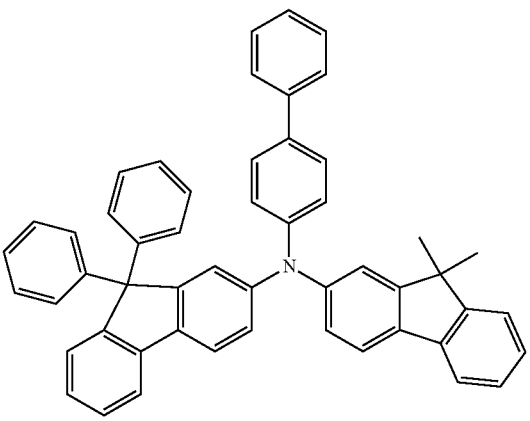

(Y2)
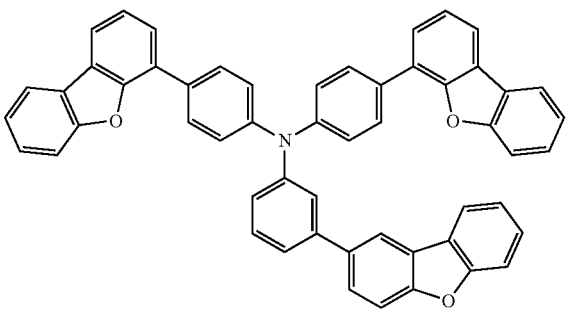

Comparative Examples 2-1 and 2-2

Each organic EL device of Comparative Examples 2-1 and 2-2 was produced in the same manner as in Examples 2-1 and 2-2, respectively, except for using NPD as the first hole transporting material.

(NPD)
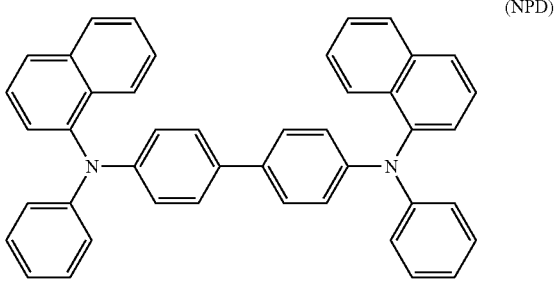 [SMILES: c1ccc(N(c2ccc(-c3ccc(N(c4ccccc4)c4cccc5ccccc45)cc3)cc2)c2cccc3ccccc23)cc1]

Evaluation of Emission Performance of Organic EL Device

Each organic EL device thus produced was measured for the luminance (L) and the current density by allowing the device to emit light under a direct current drive. Using the measured results, the current efficiency (L/J) and the driving voltage (V) at a current density of 10 mA/cm² were determined. In addition, the organic EL device was measured for the lifetime at a current density of 50 mA/cm². The 80% lifetime is the time taken until the luminance was reduced to 80% of the initial luminance when driving the device at constant current. The results are shown in Table 2.

TABLE 2

| | | | Measured Results | | |
|---|---|---|---|---|---|
| | First, hole transporting material | Second hole transporting material | Emission efficiency (cd/A) @ 10 mA/cm² | Driving voltage (V) @ 10 mA/cm² | 80% Lifetime (h) |
| Examples | | | | | |
| 2-1 | H5 | Y1 | 8.3 | 4.0 | 150 |
| 2-2 | H5 | Y2 | 8.5 | 4.0 | 230 |
| 2-3 | H6 | Y1 | 8.1 | 4.0 | 130 |
| 2-4 | H6 | Y2 | 8.4 | 4.0 | 180 |
| Comparative Examples | | | | | |
| 2-1 | NPD | Y1 | 7.2 | 4.2 | 110 |
| 2-2 | NPD | Y2 | 6.2 | 4.2 | 130 |

The results of Table 2 show that an organic EL device having a high efficiency even when driving it at a low voltage and having a long lifetime is obtained by using the aromatic amine derivative of the invention.

What is claimed is:
1. An organic electroluminescence device, comprising, in the order listed:
an anode;
a first hole transporting layer;
a second hole transporting layer;
a light emitting layer; and
a cathode;
wherein at least one of the first hole transporting layer and second hole transporting layer comprises an aromatic amine derivative represented by formula (1):

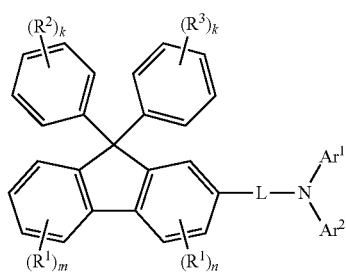

(1)

wherein in formula (1):
R¹ each independently represents a hydrogen atom, an alkyl group having 1 to 20 carbon atoms, or a phenyl group;
R² and R³ each independently represent a hydrogen atom or an alkyl group having 1 to 20 carbon atoms;
k represents an integer of 1 to 5;
m represents an integer of 1 to 4;
n represents an integer of 1 to 3;
when groups R¹ exist, the groups R¹ may be the same or different, when groups R² exist, the groups R² may be the same or different; and when groups R³ exist; the groups R³ may be the same or different;
L represents a single bond or a divalent group represented by formula (16):

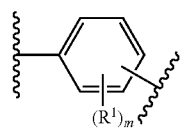

(16)

wherein in formula (16):
R¹ represents a hydrogen atom, an alkyl group having 1 to 5 carbon atoms, or a phenyl group;
m represents an integer of 1 to 4; and
when groups R¹ exist, the groups R¹ may be the same or different;
Ar¹ represents a group represented by formula (30):

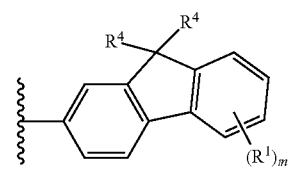

(30)

wherein in formula (30):
R¹ represents a hydrogen atom, an alkyl group having 1 to 5 carbon atoms, or a phenyl group;
m represents an integer of 1 to 4;
when groups R¹ exist, the groups R¹ may be the same or different; and
two R⁴ may be the same or different and each independently represents a methyl group or a phenyl group;
Ar² represents a group represented by formula (7):

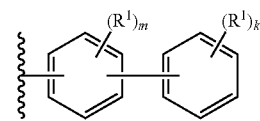

(7)

wherein in formula (7):
R¹ represents a hydrogen atom, an alkyl group having 1 to 5 carbon atoms, or a phenyl group;
k represents an integer of 1 to 5;
m represents an integer of 1 to 4; and
when groups R¹ exist, the groups R¹ may be the same or different.

2. The organic electroluminescence device according to claim 1, wherein two R⁴ represent methyl groups.
3. The organic electroluminescence device according to claim 1, wherein one of two R⁴ represents a methyl group and the other represents a phenyl group.
4. The organic electroluminescence device according to claim 1, wherein two R⁴ represent phenyl groups.
5. The organic electroluminescence device according to claim 1, wherein Ar² represents a group represented by formula (7-1) or (7-2):

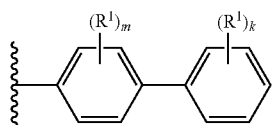

wherein $R^1$, k and m are as defined in formulae (7).

6. The organic electroluminescence device according to claim 1, wherein $R^1$ in formula (1) each independently represents a hydrogen atom, a methyl group, an ethyl group, a n-propyl group, an isopropyl group, a n-butyl group, an isobutyl group, a s-butyl group, a t-butyl group or a phenyl group.

7. The organic electroluminescence device according to claim 1, wherein $R^1$ in formula (30) represents a hydrogen atom or a phenyl group.

8. The organic electroluminescence device according to claim 1, wherein $R^1$ in formula (7) represents a hydrogen atom, a methyl group, a t-butyl group, or a phenyl group.

9. The organic electroluminescence device according to claim 1, wherein $R^1$, $R^2$ and $R^3$ in formula (1) represent hydrogen atoms.

10. The organic electroluminescence device according to claim 1, wherein $R^1$ in formula (16) represents a hydrogen atoms.

11. The organic electroluminescence device according to claim 1, wherein $R^1$ in formula (30) represents a hydrogen atom.

12. The organic electroluminescence device according to claim 1, wherein $R^1$ in formula (7) represents a hydrogen atom.

13. The organic electroluminescence device according to claim 1, wherein $R^1$, $R^2$ and $R^3$ in formula (1), $R^1$ in formula (16), $R^1$ in formula (30), and $R^1$ in formula (7) represent hydrogen atoms.

14. The organic electroluminescence device according to claim 1, wherein the aromatic amine derivative is any one of the following compounds:

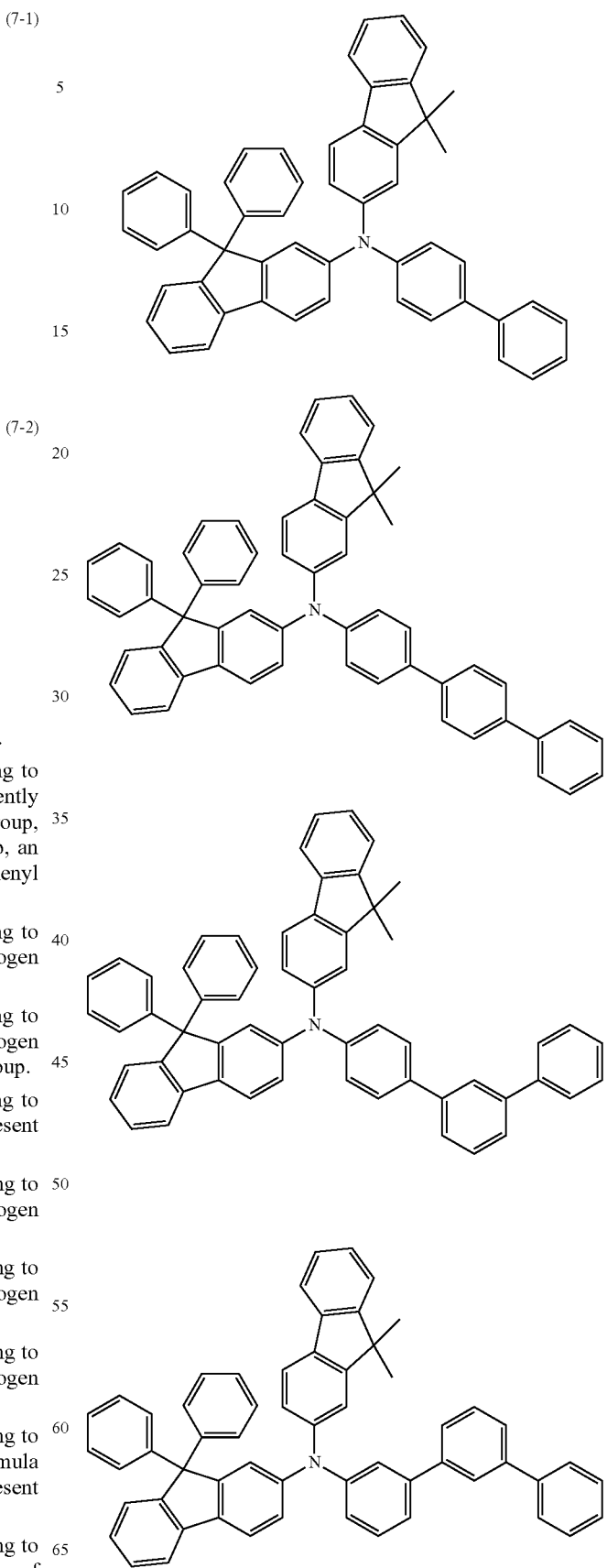

147
-continued
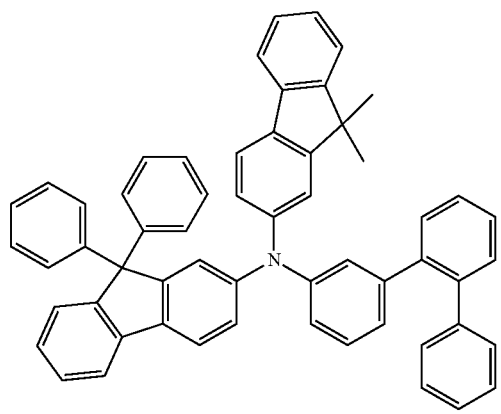
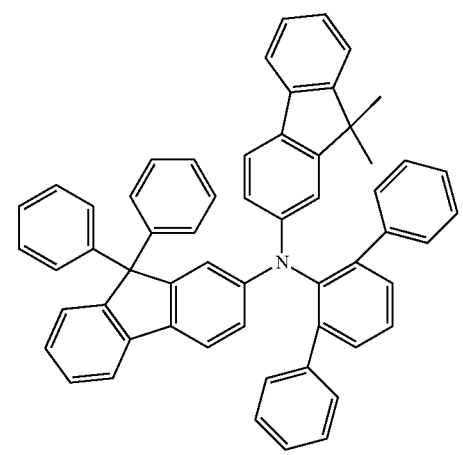
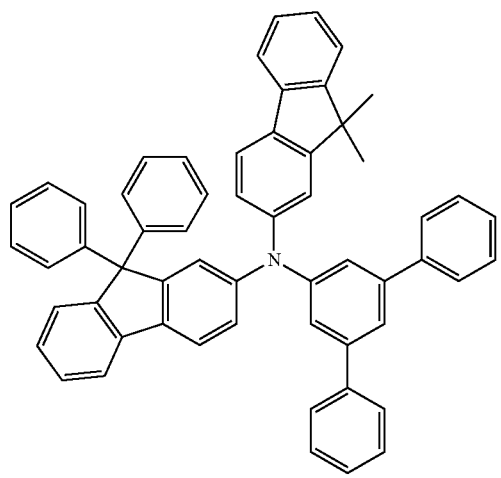
148
-continued
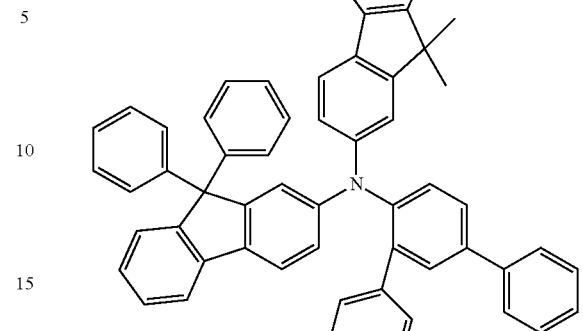
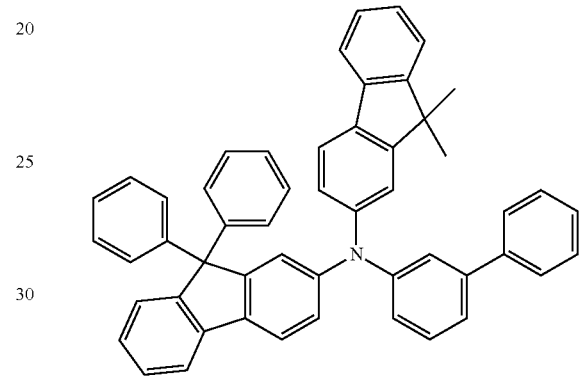
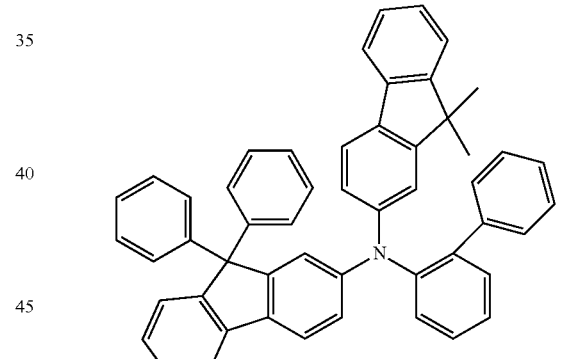
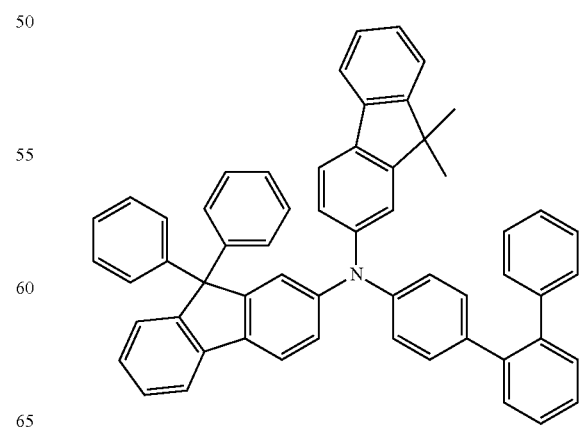

149
-continued
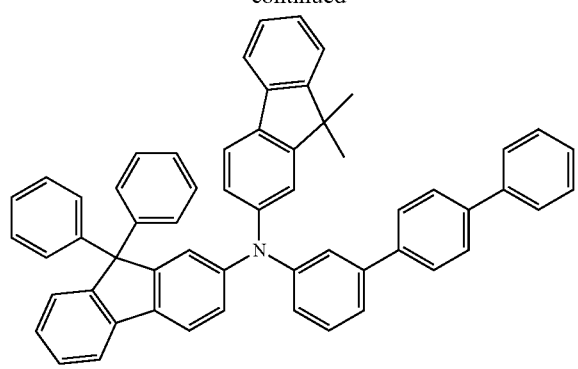
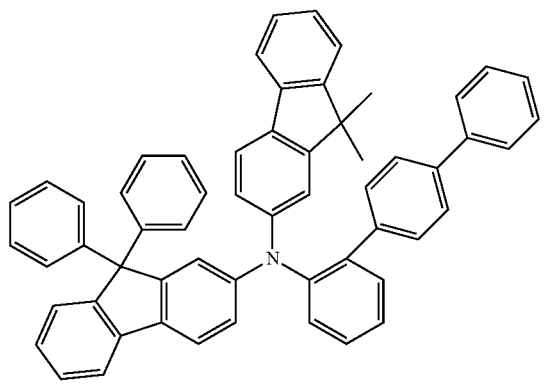
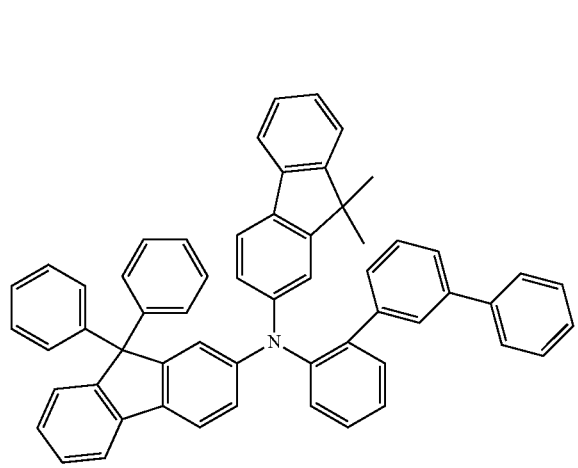
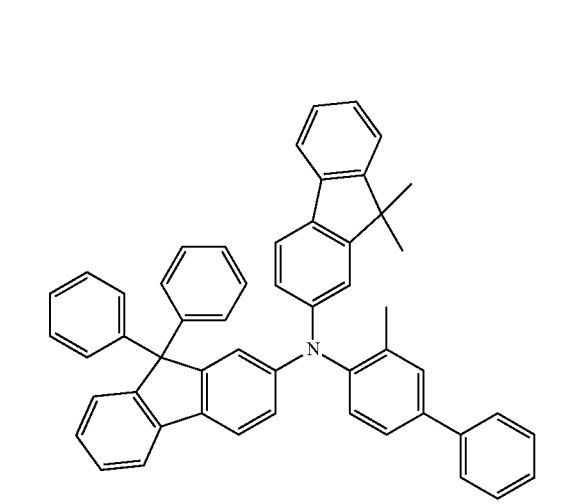
150
-continued
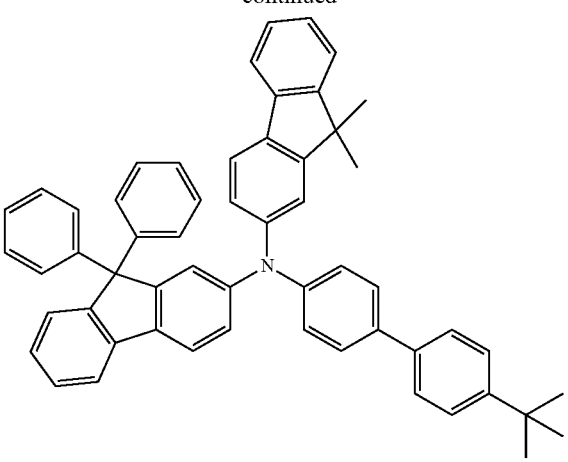
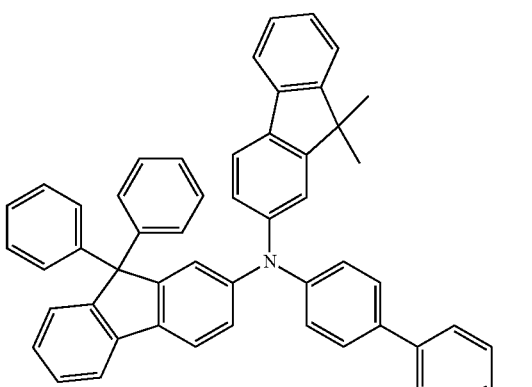
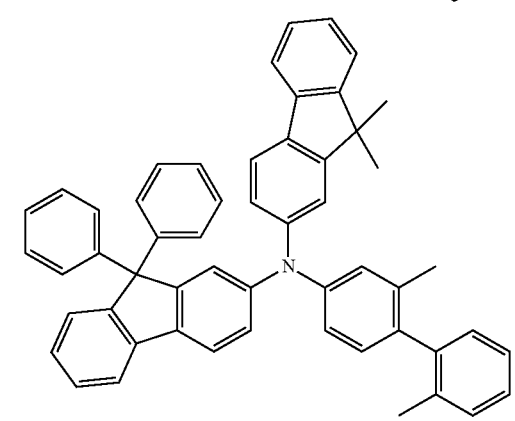
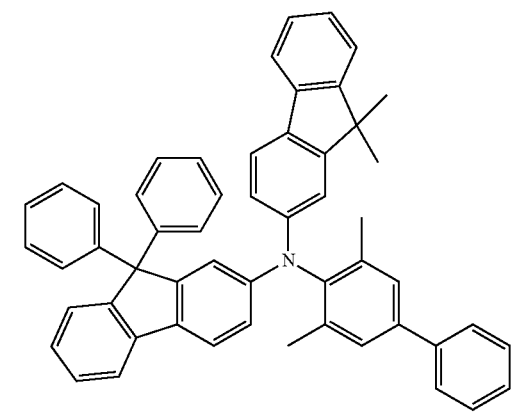

151
-continued
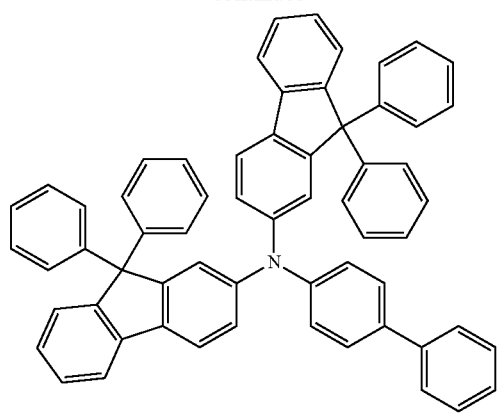
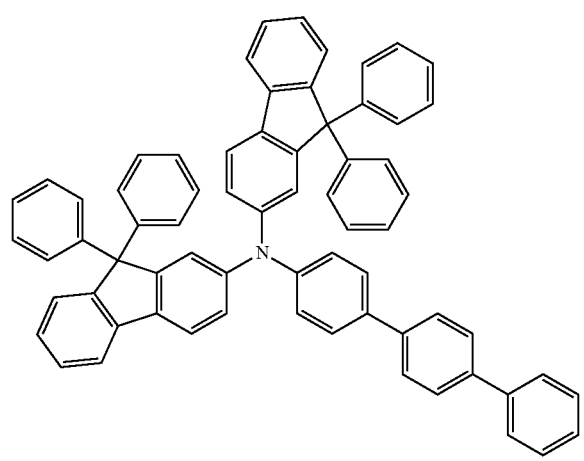
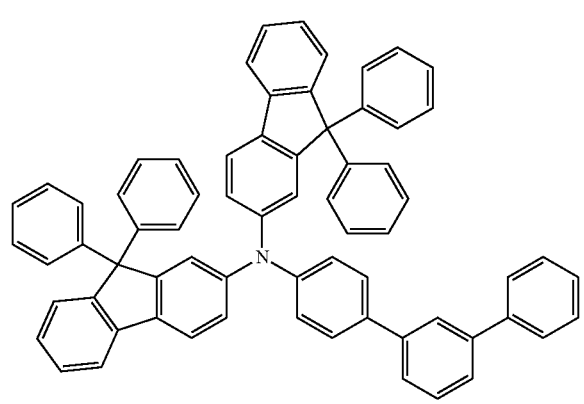
152
-continued
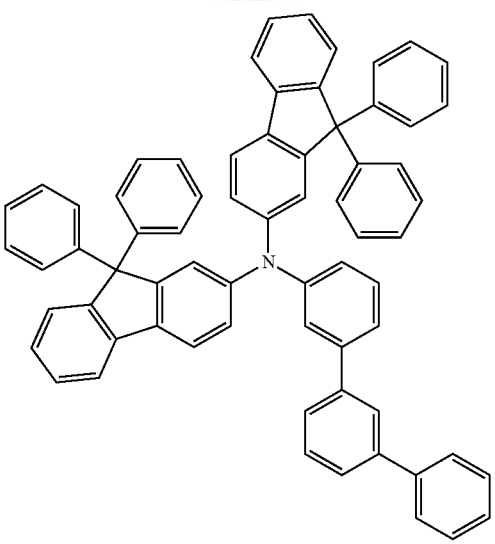
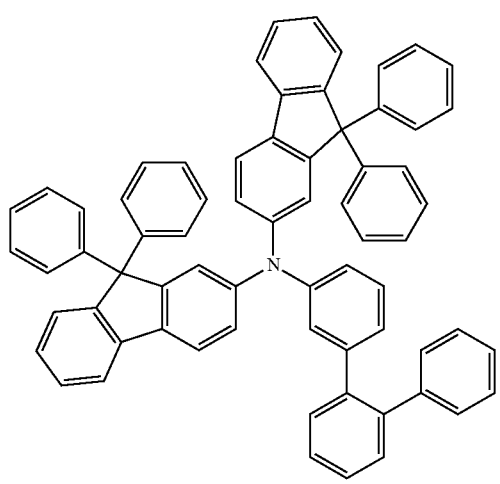
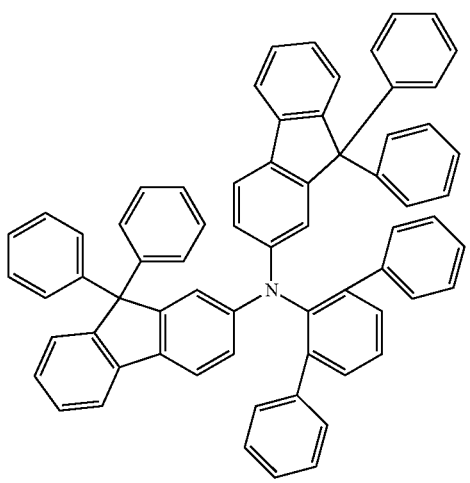

153
-continued
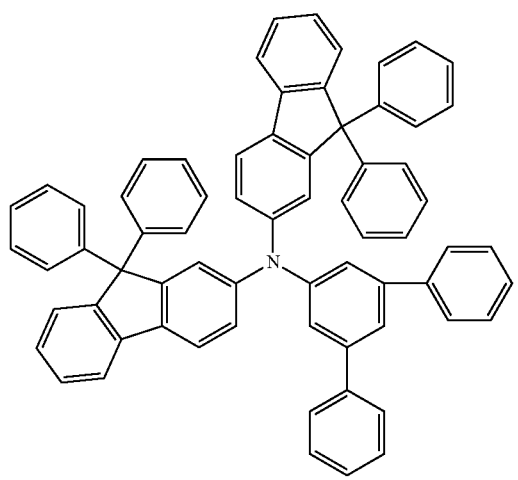
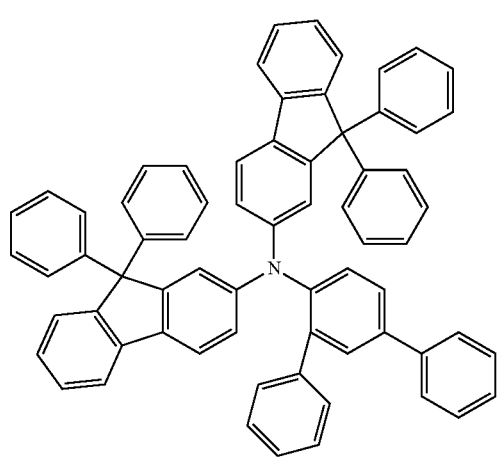
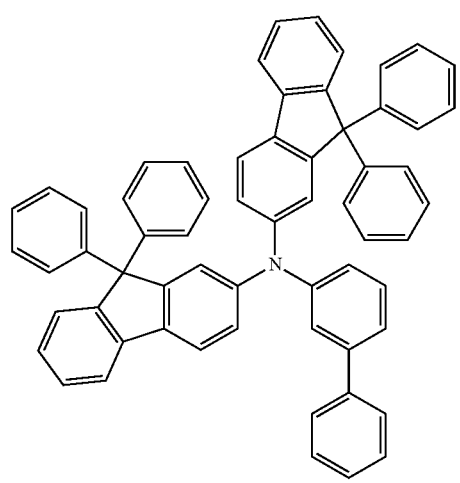
154
-continued
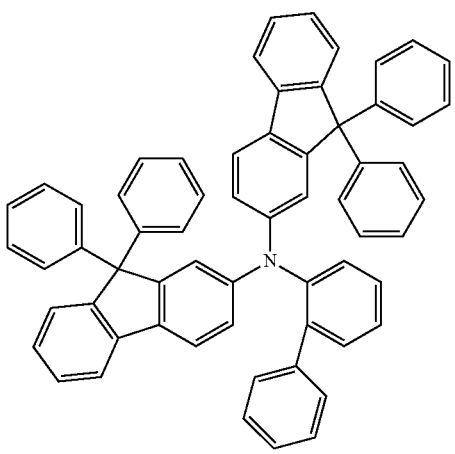
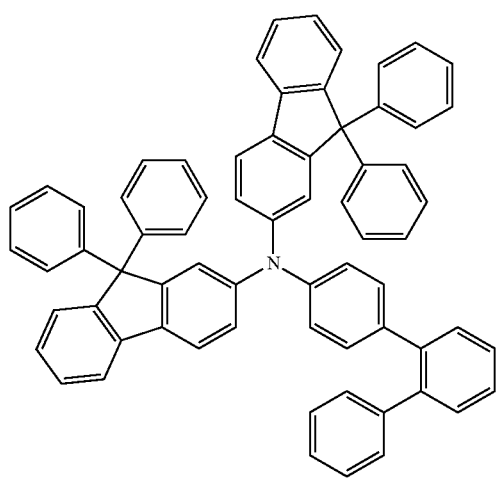
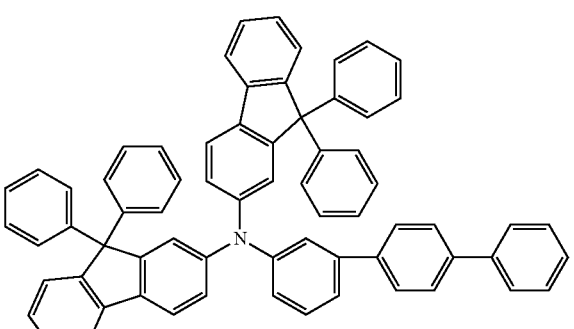

155
-continued
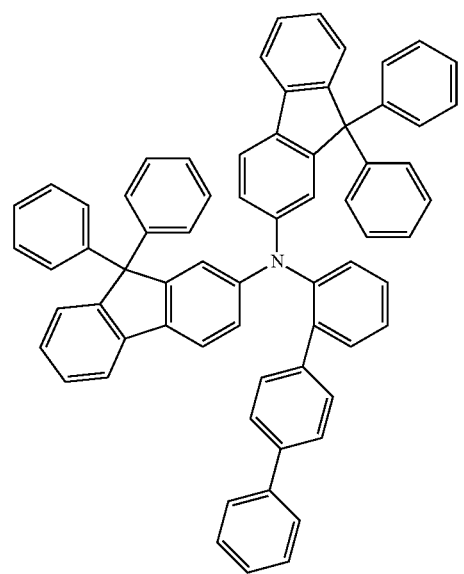
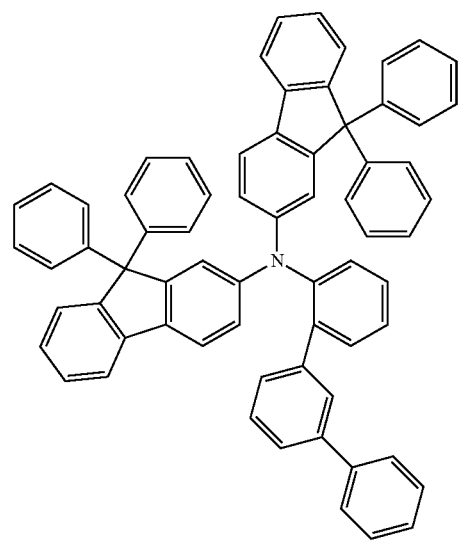
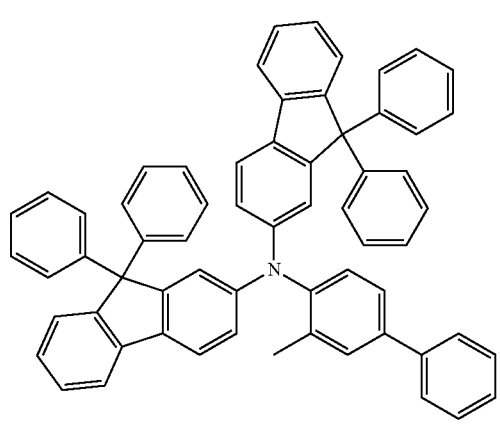
156
-continued
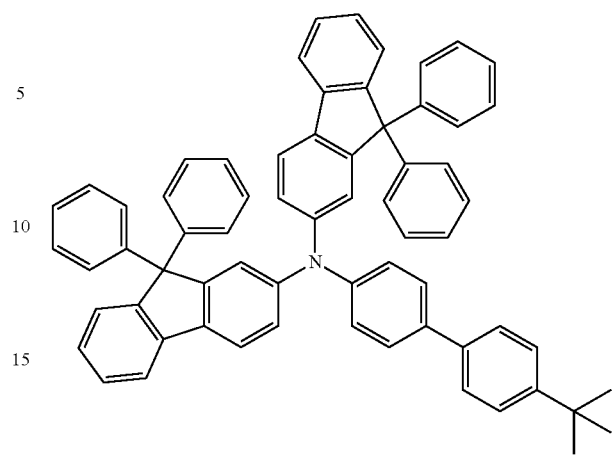
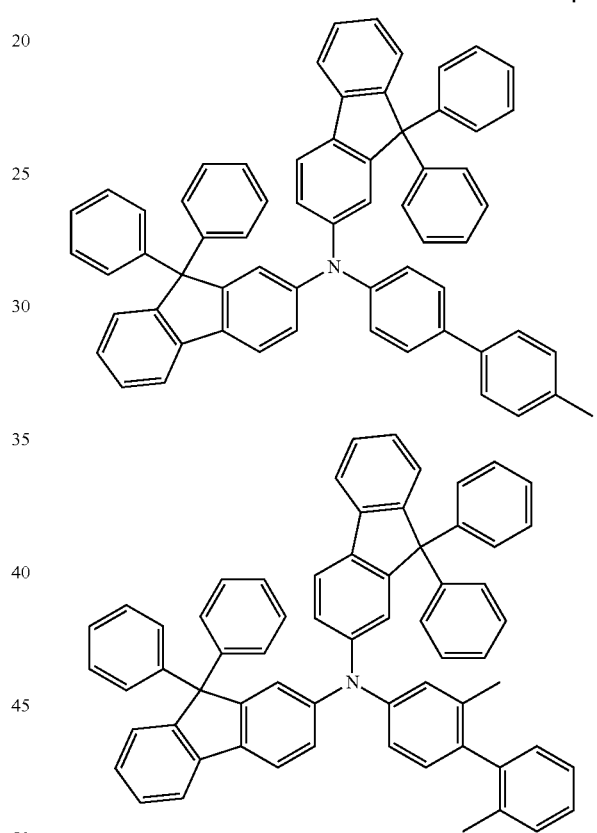
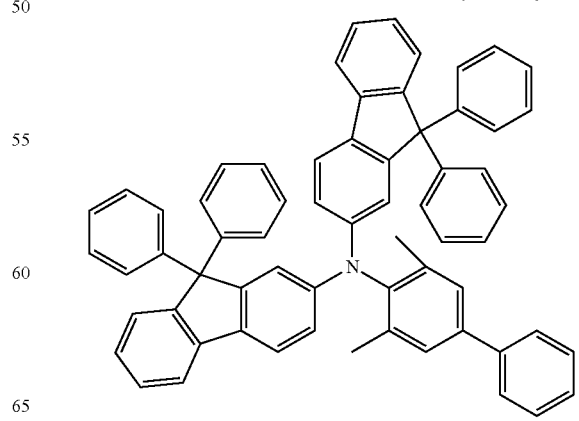

-continued
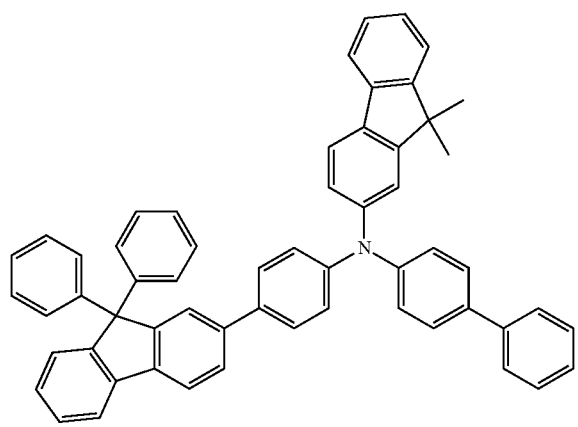
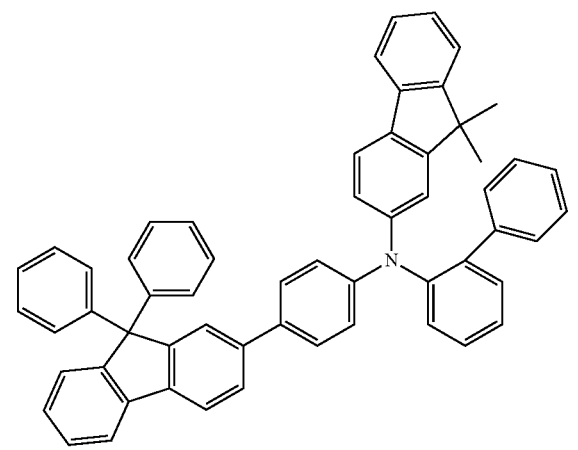
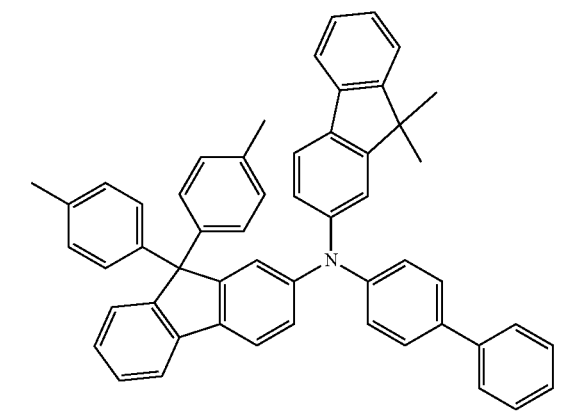
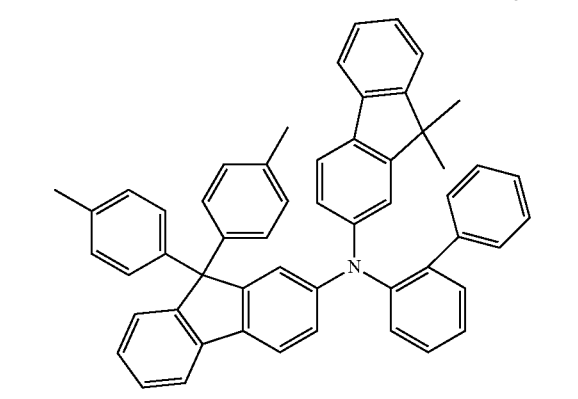
-continued
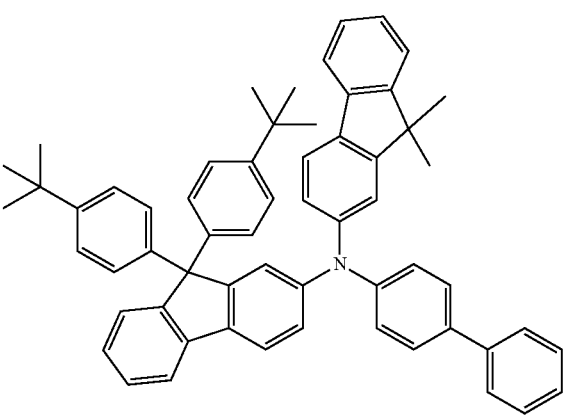
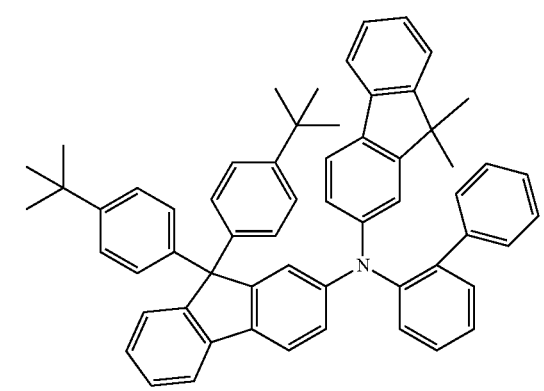
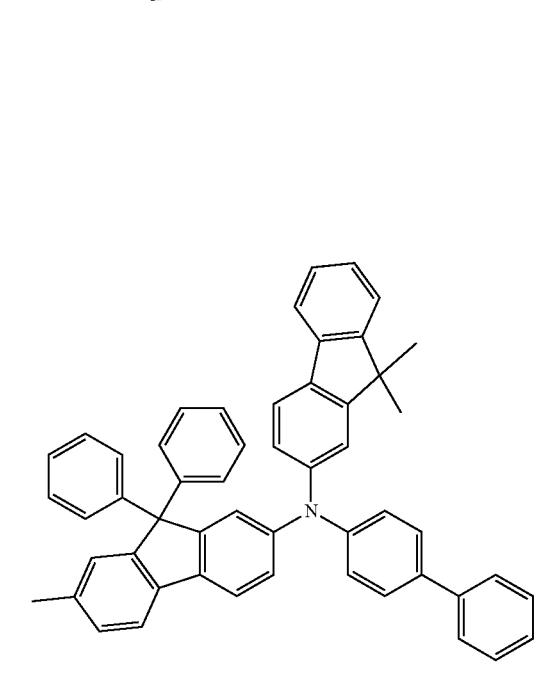

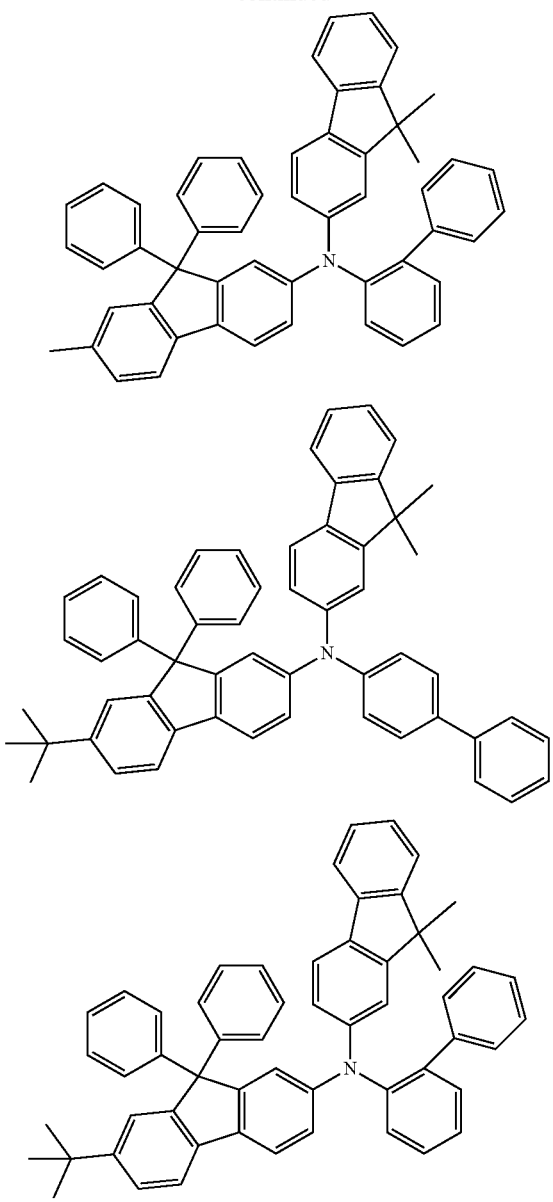

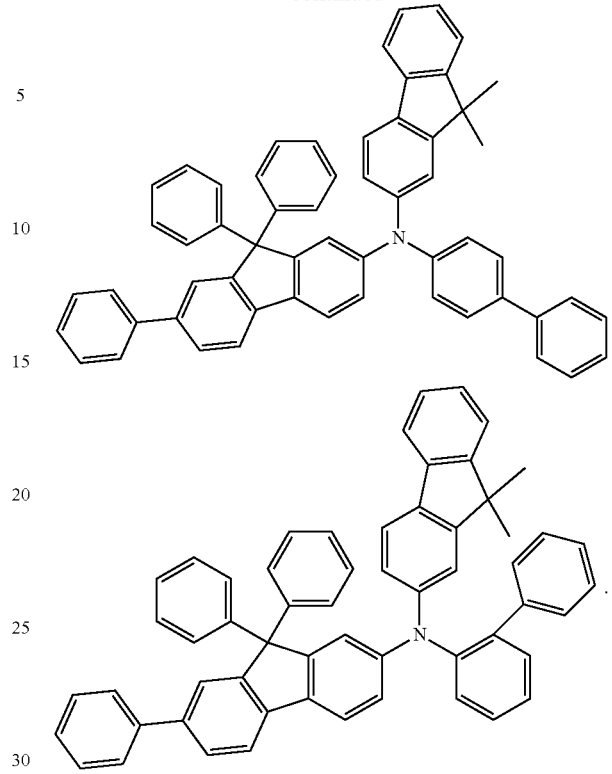

15. The organic electroluminescence device according to claim 1, wherein the first hole transporting layer comprises the aromatic amine derivative.

16. The organic electroluminescence device according to claim 1, wherein $R^2$ and $R^3$ in formula (1) each independently represents a hydrogen atom, a methyl group, an ethyl group, a n-propyl group, an isopropyl group, a n-butyl group, an isobutyl group, a s-butyl group, or a t-butyl group.

17. The organic electroluminescence device according to claim 1, wherein $R^1$ in formula (1) each independently represents a hydrogen atom or a phenyl group.

18. The organic electroluminescence device according to claim 1, wherein in $(R^1)m$ of formula (1):
$R^1$ represents a phenyl group and m represents 1; and
wherein in $(R^1)n$ of formula (1):
$R^1$ represents a hydrogen atom and n represents 3.

* * * * *